US007081344B2

(12) United States Patent
Kapeller-Libermann et al.

(10) Patent No.: US 7,081,344 B2
(45) Date of Patent: Jul. 25, 2006

(54) METHODS FOR SCREENING COMPOUNDS THAT BIND HUMAN COE-2

(75) Inventors: Rosana Kapeller-Libermann, Chestnut Hill, MA (US); Inmaculada Silos-Santiago, Cambridge, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 479 days.

(21) Appl. No.: 10/001,227

(22) Filed: Nov. 30, 2001

(65) Prior Publication Data
US 2003/0166900 A1 Sep. 4, 2003

Related U.S. Application Data

(60) Provisional application No. 60/250,929, filed on Nov. 30, 2000.

(51) Int. Cl.
G01N 33/53 (2006.01)
G01N 33/567 (2006.01)
C12N 9/64 (2006.01)

(52) U.S. Cl. .................. 435/7.1; 435/7.21; 435/226; 436/501; 530/350; 536/23.2

(58) Field of Classification Search .............. 435/7.1, 435/7.21, 226; 436/501; 530/350; 536/23.2
See application file for complete search history.

(56) References Cited

FOREIGN PATENT DOCUMENTS

| WO | WO 97/23633 A1 | 7/1997 |
|---|---|---|
| WO | WO 98/45435 A2 | 10/1998 |
| WO | WO 99/42593 A1 | 8/1999 |
| WO | WO 01/46443 A2 | 6/2001 |
| WO | WO 01/94629 A2 | 12/2001 |
| WO | WO 02/12467 * | 2/2002 |
| WO | WO 02/12467 A2 | 2/2002 |
| WO | WO 02/29103 A2 | 4/2002 |

OTHER PUBLICATIONS

Casey, K.L. (1999). Forebrain mechanisms of nociception and pain: analysis through imaging. Proc. Natl. Acad. Sci. USA 96:7668-7674.*
Julius et al. (2001). Molecular Mechanisms of nociception. Nature 413:203-210.*
Mantyh et al. (2002). Molecular mechanisms of cancer paon. Nature Reviews 2:201-209.*
Satoh et al., (1998). The mammalian carboxylesterases: from molecules to functions. Annual Review of Pharmacology and Toxicology 38:257-288.*
Wadia et al. (2003). Modulation of cellular function by TAT mediated transduction of full length proteins. Current Protein and Peptide Science. 4:97-104.*
Ghosh, Shobha, et al., "Molecular Cloning and Expression of Rat Hepatic Neutral Cholesteryl Ester Hydrolase", *Biochimica et Biophysica Acta*, vol. 1259, (Dec. 7, 1995), pp. 305-312.
Hwang, Cheng-Shine, et al., "Molecular Cloning and Sequencing of Thioesterase B cDNA and Stimulation of Expression of the Thioesterase B Gene Associated with Hormonal Induction of Peroxisome Prolilferation", *The Journal of Biological Chemistry*, vol. 268, No. 19, (Jul. 5, 1993), pp. 14278-14284.
Medda, S., et al., "The Carboxylesterase Family Exhibits C-Terminal Sequence Diversity Reflecting the Presence or Absence of Endoplasmic-Reticulum-Retention Sequences", *The European Journal of Biochemistry*, vol. 206, (Jun. 15, 1992), pp. 801-806.
Robbi, Mariette, et al., "Nucleotide Sequence of cDNA Coding for Rat Liver pI 6.1 Esterase (ES-10), a Carboxylesterase Located in the Lumen of the Endoplasmic Reticulum", *Biochemistry Journal*, vol. 269, (Jul. 15, 1990), pp. 451-458.
Satoh, Tetsuo, et al., "Molecular Aspects of Carboxylesterase Isoforms in Comparison With Other Esterases", *Toxicology Letters*, (Dec. 1995), 82/83, pp. 439-445.
Yamada, T., et al., "Localization of an Isoform of Carboxylesterase in Rat Brain Differs From That in Human Brain", *Brain Research*, vol. 674, (Mar. 13, 1995), pp. 175-179.
Hwang, C.S., et al., "Fatty Acyl-CoA Hydrolase Precursor, Medium Chain (Thioesterase B)," May 1, 2005 (sequence) GenPept [online] Bethesda, MD, USA: National Center for Biotechnology Information [retrieved on Mar. 2, 2005]. Retrieved from the Internet:. Swiss Prot Accession No. Q04791.
Hillier, L., et al., "zx42h02.r1 Soares_Total_Fetus_Nb2HF8_9w Homo Sapiens cDNA Clone IMAGE: 789171 5' Similar to TR:G1931 G1931 Carboxylesterase Precursor ;, mRNA Sequence" Jun. 4, 1997 (sequence) GenBank [online] Bethesda, MD, USA: National Center for Biotechnology Information [retrieved on Mar. 2, 2005]. Retrieved from the Internet: GenBank Accession No. AA450272.

(Continued)

Primary Examiner—Lorraine Spector
Assistant Examiner—Jon M Lockard
(74) Attorney, Agent, or Firm—Millennium Pharmaceuticals Inc.

(57) ABSTRACT

The invention provides isolated nucleic acid molecules, designated COE-2 nucleic acid molecules, which encode novel carboxylesterase family members. The invention also provides antisense nucleic acid molecules, recombinant expression vectors containing COE-2 nucleic acid molecules, host cells into which the expression vectors have been introduced, and nonhuman transgenic animals in which a COE-2 gene has been introduced or disrupted. The invention still further provides isolated COE-2 proteins, fusion proteins, antigenic peptides and anti-COE-2 antibodies. Diagnostic and therapeutic methods utilizing compositions of the invention are also provided.

8 Claims, 21 Drawing Sheets

OTHER PUBLICATIONS

Robbi, M., et al., "Liver Carboxylesterase 10 Precursor (Carboxyesterase ES-10) (PI 6.1 Esterase) (ES-HVEL)," Oct. 25, 2004 (sequence) GenPept [online] Bethesda, MD, USA: National Center for Biotechnology Information [retrieved on Mar. 2, 2005]. Retrieved from the Internet:. Swiss Prot Accession No. P16303.

Stausberg, Robert, "xu54ell.x1 NCI_CGAP_Ut1 *Homo Sapiens* cDNA Clone IMAGE:2805548 3' Similar to SW:ES10-RAT P16303 Liver Carbroxylesterase 10 Precursor ;, mRNA Sequence," Mar. 3, 2000 (sequence) GenBank [online] Bethesda, MD, USA: National Center for Biotechnology Information [retrieved on Mar. 2, 2005]. Retrieved from the Internet:. GenBank Accession No. AW512144.

McNeil, Paul L., et al., "A Method for Incorporating Macromolecules into Adherent Cells," *The Cell Journal of Cell Biology*, vol. 98, pp. 1556-1564 (Apr. 1984).

Deutsch, Mordechai, et al., "Analysis of Enzyme Kinetics in Individual Living Cells Utilizing Fluorescence Intensity and Polarization Measurements," *Cytometry*, vol. 39 pp. 36-44 (Jan. 2000).

McNeil, Paul L., "Direct Introduction of Molecules into Cells," *Current Protocols in Cell Biology*, Unit 20.1, Supplement 18, pp. 20.1.1-20.1.7 (2003).

* cited by examiner

FIG. 2A

Protein Family / Domain Matches, HMMer version 2

Searching for complete domains in PFAM
hmmpfam - search a single seq against HMM database
HMMER 2.1.1 (Dec 1998)
Copyright (C) 1992-1998 Washington University School of Medicine
HMMER is freely distributed under the GNU General Public License (GPL).

- - - - - - - - - - - - - - - - - - - - - - - - - - - - - - - - - - - -
HMM file:                /prod/ddm/seqanal/PFAM/pfam6.4/Pfam
Sequence file:           /prod/ddm/wspace/orfanal/oa-script.6214.seq
- - - - - - - - - - - - - - - - - - - - - - - - - - - - - - - - - - - -
Query:  Fbh18903FL Scores for sequence family classification (score includes all domains):
Model       Description                                   Score    E-value   N
---------   -----------                                   -----    -------   -
COesterase  Carboxylesterase                              558.6    4.1e-164  1

Parsed for domains:
Model       Domain   seq-f  seq-t    hmm-f  hmm-t           score   E-value
---------   ------   -----  -----    -----  -----           -----   -------
COesterase    1/1       25    569 ..      1    612 []       558.6   4.1e-164

Alignments of top-scoring domains:
COesterase: domain 1 of 1, from 25 to 569: score 558.6, E = 4.1e-164
          *->mvlllflllllliavlaaakaspedpllVatnnVlcGkvrGvnek
             +l+ +L 1 l ++ +l+a+++    ++ V t++   G++ G++
  18903  25 RWILCWSLTLCLMAQTALGALHT---KRPQVVTKY---GTLQGKQMH 65 tdngeqsvysFlGIPYAePPVGnLRFkaPqPYkepWsdvldAtkyppsCl
          +       ++ +FlG+P+  PP+G LRF +P+P +epW++++dAt+YPP Cl
  18903  66 VGKT--PIQVFLGVPFSRPPLGILRFAPPEP-PEPWKGIRDATYYPPGCL 112

FIG. 2B

```
              Qdddfgfslsdlkvalkmlsgwnklvg....lklsEDCLYLNVytPknt
              Q + +g+            l +++ ++ + + l +sEDCLYLNVy P+ +
18903   113   Q-ESWGQ--------LASMYVSTREfykwlRFSEDCLYLNVYAPARA   150 kpnsklPVmVwIhGGGFmFGsghslplslYdgeslaregmVIvVsiNYRL
              ++ +lPVmVw +GG+F +G++         s+Y g+ la++++V++V ++ RL
18903   151   PGDPQLPVMVWFPGGAFIVGAA-----SSYEGSDLAAREKVLVFLQHRL   195

GplGFLstgddklpgsGNyGLlDqrlALkWVqdNIaaFGGDPnsVTifGe
              G++GFLst+d+++     GN+GLlDQ +AL+WVq+NIaaFGGDP++VT+fG+
18903   196   GIFGFLSTDDSHAR--GNWGLLDQMAALRWVQENIAAFGGDPGNVTLFGQ   243

SAGaaSVslll1snggDNppsskgLFhRAIsqSGsalspwaiqsesnarg
              SAGa+S+s l++s      p++  gLFhRAIsqSG+al     +i+s+   +
18903   244   SAGAMSISGLMMS-----PLA-SGLFHRAISQSGTALFRLFITSNP--LK   285 rakelarllGCnetssselldCLRsksaeeLleatrsfllfeyvpflplf
              ak++a l+GCn++s      l+ CLR  s    ++++ ++ + +f  +
18903   286   VAKKVAHLAGCNHNSTQILVNCLRALSGTKVMRVSNK-MRFLQLNFQRDP   334 l....aFgPvvDGdDapeafipedPeelikeGkfadvPyliGvtkdEGgy
              ++ + +PvvDG+          +ip+dP+ l+ +Gk + vPyl Gv++ E+ +
18903   335   EeiiwSMSPVVDGV-----VIPDDPLVLLTQGKVSSVPYLLGVNNLEFNW   379 faamllnasskgedelkketnpdvwlellkyllfyasealnikdMddlad
              ++++ +++  + + + ket ++ l+   ll+ ++ +
18903   380   LLPYIMKFPLNR-QAMRKETITK-MLWSTRTLLN-ITKEQ-------VP   418 kvlekYpgdvddfsvesrkpnlqdmltDllFkcptrvaadlhakhggsPv
              v e+Y++ v   ++ +  ++ + d++ D +F+++  +  ++ ++++g Pv
18903   419   LVVEEYLDNVNEHDWKMLRNRMDIVQDATFVIA-TLQTAHYHRDAGLPV   467
```

FIG. 2C

```
                YaYvfdhpasfgigQflakrvdpefggavHgdEiffvFgnpllkeqlyka
                Y+Y+f h+a+    +   v+p+++ga+HgdE+++f+fFg p+ ++ l
18903   468     YLYEFEHHAR------GIIVKPRTDGADHGDEMYFLFGGPFATG-LS--   507 teeeekssktmmnywanFAktGnPnngtsnglvvWpkytseeqkYslli
                  e+++s  +mm+ywanFA+tGnP n++  +l+ Wp y+++e    +l+
18903   508     MGKEKALS-LQMMKYWANFARTGNP-NDG--NLPCWPRYNKDEK--YLQL    551 lltitaqklkardprkvlcnfw<-*
                +tt  +klk+++      ++fw
18903   552     DFTTRVGMKLKEKK-----MAFW    569
```

//
Searching for complete domains in SMART

FIG. 3A

```
GAP of: FrGcgManager_76_IOA81nWg_ check: 5132 from: 1 to: 1983

Fbh18903FL - Import - vector trimmed to: FrGcgManager_76_JOA3WXZ1_ check: 1319 from: 1 to: 2456 z34105 in Patent Nucleotide

Symbol comparison table: /ddm_local/gcg/gcg_9.1/
1/gcgcore/data/rundata/nwsgapdna.cmp
CompCheck: 8760

Gap Weight:      12      Average Match: 10.000
      Length Weight:       4      Average Mismatch: 0.000

Quality:   13796            Length:   2746
              Ratio:   6.957              Gaps:     14
  Percent Similarity:  92.617    Percent Identity: 92.617

Match display thresholds for the alignment(s):
                | = IDENTITY
                : = 5
                . = 1

FrGcgManager_76_IOA81nWg_ x FrGcgManager_76_JOA3WXZ1
 . .
                                         .
                                         .
                                         .
         .         .         .         .         .
COE-2   1 ........................................CCT 3

Z34105 101 CATTTCGCCTTGCTGACGGCGTCGAGCCCTGGCCAGACATGTCCACAGGG 150

4 TTAGCCAATTCGGCCGAGGCCTCCCGCCCCAGTA.CTTGCTGGCAGGGAT 52
           || ||     | ||| | |    || ||| | | ||    || ||
       151 TTCTCCTTCGGGTCCGGGACTCTGGGCTCCACCACCGTGGCCGCCGGCGG 200

53 TAAGAGCAGA.TAAAAGTGTGCTCACACACTGTAGACACGGCTACCATGC 101
           | |||| |      || ||| |   | ||| ||| | |
       201 GACCAGCACAGGCGGCGTTTTCTCCTTCGGAACGGGAACGTCTAGCAACC 250

102 CATC.......CACAGTGTTGCCATCCACAGTGTTGCCATCACTCCTGC. 143
           | ||       ||||||| | |   |  |  ||||| ||
       251 CTTCTGTGGGGCTCAATTTTGGAAATCTTGGAAGTACTTCAACTCCAGCA 300

144 .CCACAGCAGGAGCT...GGCTGGAGCATGAGGTGGATTCTGTG...CTGGA 188
            | |||| | |   ||    |||    ||  ||  ||| ||       |
       301 ACTACATCTGCTCCTTCAAGTGGTTTTGGAACCGGGCTCTTTGGATCTAA 350
```

FIG. 3B

```
189 GCCTCACCCT...CTGCCTGATGGCGCAGACGGCCTTGGGTGCCTTGCAC 235
    ||| | ||    |  ||   || | ||         ||||||||||||
351 ACCTGCCACTGGGTTCACTCTAGGAGGA.ACAAATACAGGTGCCTTGCAC 399

236 ACCAAGAGGCCTCAAGTGGTCACCAAATATGGAACCCTGCAAGGAAAACA 285
    ||||||||||||||||||||||||||||||||||||||||||||||||||
400 ACCAAGAGGCCTCAAGTGGTCACCAAATATGGAACCCTGCAAGGAAAACA 449

286 GATGCATGTGGGGAAGACACCCATCCAAGTCTTTTTAGGAGTCCCCTTCT 335
    ||||||||||||||||||||||||||||||||||||||||||||||||||
450 GATGCATGTGGGGAAGACACCCATCCAAGTCTTTTTAGGAGTCCCCTTCT 499

336 CCAGACCTCCTCTAGGTATCCTCAGGTTTGCACCTCCAGAACCCCGGAG 385
    |||||||||||||||||||||||||||||||||||||||||||||||||
500 CCAGACCTCCTCTAGGTATCCTCAGGTTTGCACCTCCAGAACCCCGGAG 549

386 CCCTGGAAAGGAATCAGAGATGCTACCACCTACCCGCCTG.......... 425
    ||||||||||||||||||||||||||||||||||||||||
550 CCCTGGAAAGGAATCAGAGATGCTACCACCTACCCGCCTGGATGGAGTCT 599
                        .
                        .
426 ..........GGTGCCTGCAGGAGTCCTGGGGCCAGCTGGCCTCGATGTA 465
              ||||||||||||||||||||||||||||||||||||||||
700 TGGGGCTACAGGTGCCTGCAGGAGTCCTGGGGCCAGCTGGCCTCGATGTA 749

466 CGTCAGCACGCGGGAACGGTACAAGTGGCTGCGCTTCAGCGAGGACTGTC 515
    ||||||||||||||||||||||||||||||||||||||||||||||||||
750 CGTCAGCACGCGGGAACGGTACAAGTGGCTGCGCTTCAGCGAGGACTGTC 799

516 TGTACCTGAACGTGTACGCGCCGGCGCGCGCGCCCGGGGATCCCCAGCTG 565
    ||||||||||||||||||||||||||||||||||||||||||||||||||
800 TGTACCTGAACGTGTACGCGCCGGCGCGCGCGCCCGGGGATCCCCAGCTG 849

566 CCAGTGATGGTCTGGTTCCCGGGAGGCGCCTTCATCGTGGGCGCTGCTTC 615
    ||||||||||||||||||||||||||||||||||||||||||||||||||
850 CCAGTGATGGTCTGGTTCCCGGGAGGCGCCTTCATCGTGGGCGCTGCTTC 899

616 TTCGTACGAGGGCTCTGACTTGGCCGCCCGCGAGAAAGTGGTGCTGGTGT 665
    ||||||||||||||||||||||||||||||||||||||||||||||||||
900 TTCGTACGAGGGCTCTGACTTGGCCGCCCGCGAGAAAGTGGTGCTGGTGT 949

666 TTCTGCAGCACAGGCTCGGCATCTTCGGCTTCCTGAGCACGGACGACAGC 715
    ||||||||||||||||||||||||||||||||||||||||||||||||||
950 TTCTGCAGCACAGGCTCGGCATCTTCGGCTTCCTGAGCACGGACGACAGC 999

716 CACGCGCGCGGGAACTGGGGGCTGCTGGACCAGATGGCGGCTCTGCGCTG 765
```

FIG. 3C

```
 766 GGTGCAGGAGAACATCGCAGCCTTCGGGGGAGACCCAGGAAATGTGACCC  815
     ||||||||||||||||||||||||||||||||||||||||||||||||||
1050 GGTGCAGGAGAACATCGCAGCCTTCGGGGGAGACCCAGGAAATGTGACCC 1099

816 TGTTCGGCCAGTCGGCGGGGGCCATGAGCATCTCAGGACTGATGATGTCA  865
     ||||||||||||||||||||||||||||||||||||||||||||||||||
1100 TGTTCGGCCAGTCGGCGGGGGCCATGAGCATCTCAGGACTGATGATGTCA 1149

866 CCCCTAGCCTCGGGTCTCTTCCATCGGGCCATTTCCCAGAGTGGCACCGC  915
     ||||||||||||||||||||||||||||||||||||||||||||||||||
1150 CCCCTAGCCTCGGGTCTCTTCCATCGGGCCATTTCCCAGAGTGGCACCGC 1199

916 GTTATTCAGACTTTTCATCACTAGTAACCCACTGAAAGTGGCCAAGAAGG  965
     ||||||||||||||||||||||||||||||||||||||||||||||||||
1200 GTTATTCAGACTTTTCATCACTAGTAACCCACTGAAAGTGGCCAAGAAGG 1249

966 TTGCCCACCTGGCTGGATGCAACCACAACAGCACACAGATCCTGGTAAAC 1015
     ||||||||||||||||||||||||||||||||||||||||||||||||||
1250 TTGCCCACCTGGCTGGATGCAACCACAACAGCACACAGATCCTGGTAAAC 1299

1016 TGCCTGAGGGCACTATCAGGGACCAAGGTGATGCGTGTGTCCAACAAGAT 1065
     ||||||||||||||||||||||||||||||||||||||||||||||||||
1300 TGCCTGAGGGCACTATCAGGGACCAAGGTGATGCGTGTGTCCAACAAGAT 1349

1066 GAGATTCCTCCAACTGAACTTCCAGAGAGACCCGGAAGAGATTATCTGGT 1115
     ||||||||||||·|||||||||||||||||||||||||||||||||||||
1350 GAGATTCCTCCAACTGAACTTCCAGAGAGACCCGGAAGAGATTATCTGGT 1399

1116 CCATGAGCCCTGTGGTGGATGGTGTGGTGATCCCAGATGACCCTTTGGTG 1165
     ||||||||||||||||||||||||||||||||||||||||||||||||||
1400 CCATGAGCCCTGTGGTGGATGGTGTGGTGATCCCAGATGACCCTTTGGTG 1449

1166 CTCCTGACCCAGGGGAAGGTTTCATCTGTGCCCTACCTTCTAGGTGTCAA 1215
     ||||||||||||||||||||||||||||||||||||||||||||||||||
1450 CTCCTGACCCAGGGGAAGGTTTCATCTGTGCCCTACCTTCTAGGTGTCAA 1499

1216 CAACCTGGAATTCAATTGGCTCTTGCCTTATATCATGAAGTTCCCGCTAA 1265
     |||||||||||||||||||||||||||||
1500 CAACCTGGAATTCAATTGGCTCTTGCCTTAT.................. 1530

1316 CGCACCCTGTTGAATATCACCAAGGAGCAGGTACCACTTGTGGTGGAGGA 1365
                 ||||||||||||||||||||||||||||||||||||||
1531 ...........AATATCACCAAGGAGCAGGTACCACTTGTGGTCGAGGA 1568

1366 GTACCTGGACAATGTCAATGAGCATGACTGGAAGATGCTACGAAACCGTA 1415
```

FIG. 3D

```
1416 TGATGGACATAGTTCAAGATGCCACTTTCGTGTATGCCACACTGCAGACT 1465
     ||||||||||||||||||||||||||||||||||||||||||||||||||
1619 TGATGGACATAGTTCAAGATGCCACTTTCGTGTATGCCACACTGCAGACT 1668

1466 GCTCACTACCACCGAGATGCCGGCCTCCCTGTCTACCTGTATGAATTTGA 1515
     |||||||||||||||
1669 GCTCACTACCACCGA................................... 1683
                             .
                             .

1666 CAACTTTGCCCGCACAGGAAACCCCAATGATGGGAATCTGCCCTGCTGGC 1715
                          |||||||||||||||||||||||||||||||
1684 ..................GAAACCCCAATGATGGGAATCTGCCCTGCTGGC 1716

1716 CACGCTACAACAAGGATGAAAAGTACCTGCAGCTGGATTTTACCACAAGA 1765
     ||||||||||||||||||||||||||||||||||||||||||||||||||
1717 CACGCTACAACAAGGATGAAAAGTACCTGCAGCTGGATTTTACCACAAGA 1766

1766 GTGGGCATGAAGCTCAAGGAGAAGAAGATGGCTTTTTGGATGAGTCTGTA 1815
     ||||||||||||||||||||||||||||||||||||||||||||||||||
1767 GTGGGCATGAAGCTCAAGGAGAAGAAGATGGCTTTTTGGATGAGTCTGTA 1816

1816 CCAGTCTCAAAGACCTGAGAAGCAGAGGCAATTCTAAGGGTGGCTATGCA 1865
     ||||||||||||||||||||||||||||||||||||||||||||||||||
1817 CCAGTCTCAAAGACCTGAGAAGCAGAGGCAATTCTAAGGGTGGCTATGCA 1866

1866 GGAAGGAGCCAAAGAGGGGTTTGCCCCCACCATCCAGGCCCTGGGGAGAC 1915
     ||||||||||||||||||||||||||||||||||||||||||||||||||
1867 GGAAGGAGCCAAAGAGGGGTTTGCCCCCACCATCCAGGCCCTGGGGAGAC 1916

1916 TAGCCATGGACATACCTGGGGACAAGAGTTCTACCCAAGGGCGAATTCGT 1965
     ||||||||||||||||||||||||||||||||||    |    |   ||
1917 TAGCCATGGACATACCTGGGGACAAGAGTTCTACCCA...CCCCA...GT 1960

1966 TTAAACCTGCAGGA.CTAG............................... 1983
     ||| | ||||||||| ||
1961 TTAGAACTGCAGGAGCTCCCTGCTGCCTCCAGGCCAAAGCTAGAGCTTTT 2010
                             .
                             .
```

FIG. 4A

ALIGN calculates a global alignment of two sequences
version 2.0uplease cite: Myers and Miller, CABIOS (1989)
                                     COE-2   584 aa vs.
                                     PRO873  545 aa scoring matrix: BLOSUM50, gap penalties: -12/-2
62.4% identity;  Global alignment score: 2271

```
                                                                        10
COE-2    M----------------------------------------------PST------VLPSTVLPSLLPTAG
          :                                             ::.     : ::  :.  .   .
pro873   MSTGFSFGSGTLGSTTVAAGGTSTGGVFSFGTGTSSNPSVGLNFGNLGSTSTPATTSAPS
              10        20        30        40        50        60

20        30        40        50        60        70
COE-2    AGWSMRWILCWSLTLCLMAQTALGALHTKRPQVVTKYGTLQGKQMHVGKTPIQVFLGVPF
          :::  .  :  . :::::::::::::::::::::::::::::::::::::::::::::
pro873   SGFGTGLFGSKPATGFTLGGTNTGALHTKRPQVVTKYGTLQGKQMHVGKTPIQVFLGVPF
              70        80        90       100       110       120

80        90       100       110
COE-2    SRPPLGILRFAPPEPPEPWKGIRDATTYPPG-----------------------------
         ::::::::::::::::::::::::::::::
pro873   SRPPLGILRFAPPEPPEPWKGIRDATTYPPGWSLALSPGWSAVARSRLTATSASRVQASL
             130       140       150       160       170       180

120       130       140       150
COE-2    -----------CLQESWGQLASMYVSTRERYKWLRFSEDCLYLNVYAPARAPGDPQLPVM
                    ::::::::::::::::::::::::::::::::::::::::::::::::
pro873   LPQPLSVWGYTRCLQESWGQLASMYVSTRERYKWLRFSEDCLYLNVYAPARAPGDPQLPVM
             190       200       210       220       230       240
```

FIG. 4B

```
         160         170         180         190         200         210
COE-2    VWFPGGAFIVGAASSYEGSDLAAREKVVLVFLQHRLGIFGFLSTDDSHARGNWGLLDQMA
         ::::::::::::::::::::::::::::::::::::::::::::::::::::::::::::
pro873   VWFPGGAFIVGAASSYEGSDLAAREKVVLVFLQHRLGIFGFLSTDDSHARGNWGLLDQMA
         220         230         240         250         260         270

220         230         240         250         260         270
COE-2    ALRWVQENLAAFGGDPGNVTLFGQSAGAMSISGLMMSPLASGLFHRAISQSGTALFRLFI
         ::::::::::::::::::::::::::::::::::::::::::::::::::::::::::::
pro873   ALRWVQENLAAFGGDPGNVTLFGQSAGAMSISGLMMSPLASGLFHRAISQSGTALFRLFI
         280         290         300         310         320         330

280         290         300         310         320         330
COE-2    TSNPLKVAKKVAHLAGCNHNSTQILVNCLRALSGTKVMRVSNKMRFLQLNFQRDPEEIIW
         ::::::::::::::::::::::::::::::::::::::::::::::::::::::::::::
pro873   TSNPLKVAKKVAHLAGCNHNSTQILVNCLRALSGTKVMRVSNKMRFLQLNFQRDPEEIIW
         340         350         360         370         380         390

340         350         360         370         380         390
COE-2    SMSPVVDGVVIPDDPLVLLTQGKVSSVPYLLGVNNLEFNWLLPYIMKFPLNRQAMRKETI
         :::::::::::::::::::::::::::::::::::::::::::::::
pro873   SMSPVVDGVVIPDDPLVLLTQGKVSSVPYLLGVNNLEFNWLLPY---------------
         400         410         420         430         440         450

400         410         420         430         440         450
COE-2    TKMLWSTRTLLNITKEQVPLVVEEYLDNVNEHDWKMLRNRMDIVQDATFVYATLQTAHY
                ::::::::::::::::::::::::::::::::::::::::::::::::::
pro873   ------NITKEQVPLVVEEYLDNVNEHDWKMLRNRMDIVQDATFVYATLQTAHY
         460         470         480         490         500         510
```

FIG. 4C

```
        460         470         480         490         500         510
COE-2   HRDAGLPVYLYEFEHHARGIIVKPRTDGADHGDEMYFLFGGPFATGLSMGKEKALSLQMM
        ::::   :.:              ::          :.:.:
pro873  HRET--PMM----------GIC--P----AGHA---------------------------
                 520

520         530         540         550         560         570
COE-2   KYWANFARTGNPNDGNLPCWPRYNKDEKYLQLDFTTRVGMKLKEKKMAFWMSLYQSQRPE
                                                :::.  :.:
pro873  ------------------------------TTRM-----KSTCSWIL-----P-
                                          530                540

580
COE-2   KQRQF
        :.
pro873  -QEWA
```

FIG. 7A-4

| Lung/COPD | Tonsil/normal | Lymph node/ normal | Thymus/ normal | Epithelial Cells (Prostate) | Endothelial Cells (Aortic) | Skeletal Muscle | Fibroblasts (Dermal) | Skin/Normal | Adipose/ Normal |
|---|---|---|---|---|---|---|---|---|---|
| 29.44 | 31.13 | 31.40 | 32.80 | 30.70 | 35.27 | 31.06 | 33.10 | 31.16 | 32.43 |
| 17.10 | 17.19 | 17.91 | 20.03 | 20.13 | 20.16 | 18.26 | 18.18 | 20.29 | 17.96 |
| 12.34 | 13.94 | 13.49 | 12.78 | 10.57 | 15.11 | 12.81 | 14.92 | 10.87 | 14.47 |
| 0.19 | 0.06 | 0.09 | 0.14 | 0.66 | 0.03 | 0.14 | 0.03 | 0.54 | 0.04 |

FIG. 7A-5

| Osteoblasts (Primary) | Osteoblasts (Undiff) | Osteoblasts (Diff) | Osteoclasts | Aorta SMC (Early) | Aorta SMC (Late) | HUVEC | HMVEC |
|---|---|---|---|---|---|---|---|
| 34.84 | 33.19 | 33.23 | 32.47 | 32.50 | 32.72 | 32.17 | 32.74 |
| 20.44 | 18.50 | 17.83 | 17.25 | 19.53 | 18.77 | 19.27 | 18.74 |
| 14.40 | 14.69 | 15.40 | 15.22 | 12.97 | 13.96 | 12.91 | 14.00 |
| 0.05 | 0.04 | 0.02 | 0.03 | 0.13 | 0.06 | 0.13 | 0.06 |

FIG. 7B

| Tissue | 18903 MEAN | β2M803 MEAN | δ Ct | Expression |
|---|---|---|---|---|
| Fetal heart/normal | 31.89 | 19.68 | 12.21 | 0.21 |
| Aorta/normal | 36.11 | 22.53 | 13.58 | 0.00 |
| Heart normal | 31.54 | 17.89 | 13.65 | 0.08 |
| Heart/CHF | 31.50 | 19.45 | 12.05 | 0.24 |
| Vein/normal | 36.01 | 18.99 | 17.02 | 0.00 |
| SMC (Aortic) | 31.76 | 18.74 | 13.02 | 0.12 |
| Spinal cord/normal | 33.06 | 21.40 | 11.66 | 0.31 |
| Brain cortex/normal | 29.68 | 20.58 | 9.10 | 1.83 |
| Brain hypothalamus/normal | 29.45 | 19.24 | 10.21 | 0.85 |
| Glial cells (Astrocytes) | 33.94 | 21.09 | 12.86 | 0.13 |
| Brain/Glioblastoma | 30.39 | 17.43 | 12.97 | 0.13 |
| Breast/normal | 30.10 | 18.60 | 11.50 | 0.35 |
| Breast tumor/IDC | 30.75 | 17.66 | 13.09 | 0.11 |
| Ovary/normal | 31.73 | 19.95 | 11.79 | 0.28 |
| Ovary/tumor | 33.59 | 18.91 | 14.68 | 0.04 |
| Pancreas | 30.88 | 17.33 | 13.55 | 0.08 |
| Prostate/normal | 31.16 | 18.34 | 12.83 | 0.14 |
| Prostate/tumor | 29.03 | 17.57 | 11.46 | 0.35 |
| Colon/normal | 32.03 | 17.78 | 14.26 | 0.05 |
| Colon/tumor | 30.80 | 18.15 | 12.66 | 0.16 |
| Colon/IBD | 32.37 | 17.72 | 14.65 | 0.04 |
| Kidney/normal | 30.98 | 20.03 | 10.95 | 0.51 |
| Liver/normal | 31.82 | 19.08 | 12.75 | 0.15 |
| Liver/fibrosis | 30.10 | 18.82 | 11.29 | 0.40 |
| Fetal Liver/normal | 33.55 | 21.39 | 12.16 | 0.22 |
| Lung/normal | 30.54 | 17.31 | 13.23 | 0.10 |
| Lung/tumor | 30.30 | 17.77 | 12.53 | 0.17 |
| Lung/COPD | 29.44 | 17.10 | 12.34 | 0.19 |
| Tonsil/normal | 31.13 | 17.19 | 13.94 | 0.06 |
| Lymph node/normal | 31.40 | 17.91 | 13.49 | 0.09 |
| Thymus/normal | 32.80 | 20.03 | 12.78 | 0.14 |
| Epithelial Cells (prostate) | 30.70 | 20.13 | 10.57 | 0.66 |
| Endothelial Cells (aortic) | 35.27 | 20.16 | 15.11 | 0.03 |
| Skeletal Muscle/normal | 31.06 | 18.26 | 12.81 | 0.14 |
| Fibroblasts (Dermal) | 33.10 | 18.18 | 14.92 | 0.03 |
| Skin/normal | 31.16 | 20.29 | 10.87 | 0.54 |
| Adipose/normal | 32.43 | 17.96 | 14.47 | 0.04 |
| Osteoblasts (primary) | 34.84 | 20.44 | 14.40 | 0.05 |
| Osteoblasts (Undiff) | 33.19 | 18.50 | 14.69 | 0.04 |
| Osteoblasts (Diff) | 33.23 | 17.83 | 15.40 | 0.02 |
| Osteoblasts | 32.47 | 17.25 | 15.22 | 0.03 |
| Aorta SMC (Early) | 32.50 | 19.53 | 12.97 | 0.13 |
| Aorta SMC (Late) | 32.72 | 18.77 | 13.96 | 0.06 |
| HUVEC | 32.17 | 19.27 | 12.91 | 0.13 |
| HMVEC | 32.74 | 18.74 | 14.00 | 0.06 |
|  | 40.00 | 40.00 | 0.00 |  |

SEQUENCE LISTING

<160> NUMBER OF SEQ ID NOS: 7

<210> SEQ ID NO 1
<211> LENGTH: 1983
<212> TYPE: DNA
<213> ORGANISM: Homo sapiens
<220> FEATURE:
<221> NAME/KEY: CDS
<222> LOCATION: (98)...(1849)

<400> SEQUENCE: 1

```
cctttagcca attcggccga ggcctcccgc cccagtactt gctggcaggg attaagagca        60
gataaaagtg tgctcacaca ctgtagacac ggctacc atg cca tcc aca gtg ttg       115
                                        Met Pro Ser Thr Val Leu
                                          1               5 cca tcc aca gtg ttg cca tca ctc ctg ccc aca gca gga gct ggc tgg        163
Pro Ser Thr Val Leu Pro Ser Leu Leu Pro Thr Ala Gly Ala Gly Trp
             10                  15                  20 agc atg agg tgg att ctg tgc tgg agc ctc acc ctc tgc ctg atg gcg        211
Ser Met Arg Trp Ile Leu Cys Trp Ser Leu Thr Leu Cys Leu Met Ala
         25                  30                  35 cag acg gcc ttg ggt gcc ttg cac acc aag agg cct caa gtg gtc acc        259
Gln Thr Ala Leu Gly Ala Leu His Thr Lys Arg Pro Gln Val Val Thr
 40                  45                  50 aaa tat gga acc ctg caa gga aaa cag atg cat gtg ggg aag aca ccc        307
Lys Tyr Gly Thr Leu Gln Gly Lys Gln Met His Val Gly Lys Thr Pro
 55                  60                  65                  70 atc caa gtc ttt tta gga gtc ccc ttc tcc aga cct cct cta ggt atc        355
Ile Gln Val Phe Leu Gly Val Pro Phe Ser Arg Pro Pro Leu Gly Ile
                 75                  80                  85 ctc agg ttt gca cct cca gaa ccc ccg gag ccc tgg aaa gga atc aga        403
Leu Arg Phe Ala Pro Pro Glu Pro Pro Glu Pro Trp Lys Gly Ile Arg
             90                  95                 100 gat gct acc acc tac ccg cct ggg tgc ctg cag gag tcc tgg ggc cag        451
Asp Ala Thr Thr Tyr Pro Pro Gly Cys Leu Gln Glu Ser Trp Gly Gln
        105                 110                 115 ctg gcc tcg atg tac gtc agc acg cgg gaa cgg tac aag tgg ctg cgc        499
Leu Ala Ser Met Tyr Val Ser Thr Arg Glu Arg Tyr Lys Trp Leu Arg
    120                 125                 130 ttc agc gag gac tgt ctg tac ctg aac gtg tac gcg ccg gcg cgc gcg        547
Phe Ser Glu Asp Cys Leu Tyr Leu Asn Val Tyr Ala Pro Ala Arg Ala
135                 140                 145                 150 ccc ggg gat ccc cag ctg cca gtg atg gtc tgg ttc ccg gga ggc gcc        595
Pro Gly Asp Pro Gln Leu Pro Val Met Val Trp Phe Pro Gly Gly Ala
                155                 160                 165 ttc atc gtg ggc gct gct tct cg tac gag ggc tct gac ttg gcc gcc        643
Phe Ile Val Gly Ala Ala Ser Ser Tyr Glu Gly Ser Asp Leu Ala Ala
            170                 175                 180 cgc gag aaa gtg gtg ctg gtg ttt ctg cag cac agg ctc ggc atc ttc        691
Arg Glu Lys Val Val Leu Val Phe Leu Gln His Arg Leu Gly Ile Phe
        185                 190                 195 ggc ttc ctg agc acg gac gac agc cac gcg cgc ggg aac tgg ggg ctg        739
Gly Phe Leu Ser Thr Asp Asp Ser His Ala Arg Gly Asn Trp Gly Leu
    200                 205                 210 ctg gac cag atg gcg gct ctg cgc tgg gtg cag gag aac atc gca gcc        787
Leu Asp Gln Met Ala Ala Leu Arg Trp Val Gln Glu Asn Ile Ala Ala
215                 220                 225                 230 ttc ggg gga gac cca gga aat gtg acc ctg ttc ggc cag tcg gcg ggg        835
Phe Gly Gly Asp Pro Gly Asn Val Thr Leu Phe Gly Gln Ser Ala Gly
```

-continued

```
                235                 240                 245
gcc atg agc atc tca gga ctg atg atg tca ccc cta gcc tcg ggt ctc         883
Ala Met Ser Ile Ser Gly Leu Met Met Ser Pro Leu Ala Ser Gly Leu
            250                 255                 260 ttc cat cgg gcc att tcc cag agt ggc acc gcg tta ttc aga ctt ttc         931
Phe His Arg Ala Ile Ser Gln Ser Gly Thr Ala Leu Phe Arg Leu Phe
            265                 270                 275 atc act agt aac cca ctg aaa gtg gcc aag aag gtt gcc cac ctg gct         979
Ile Thr Ser Asn Pro Leu Lys Val Ala Lys Lys Val Ala His Leu Ala
        280                 285                 290 gga tgc aac cac aac agc aca cag atc ctg gta aac tgc ctg agg gca       1027
Gly Cys Asn His Asn Ser Thr Gln Ile Leu Val Asn Cys Leu Arg Ala
295                 300                 305                 310 cta tca ggg acc aag gtg atg cgt gtg tcc aac aag atg aga ttc ctc       1075
Leu Ser Gly Thr Lys Val Met Arg Val Ser Asn Lys Met Arg Phe Leu
            315                 320                 325 caa ctg aac ttc cag aga gac ccg gaa gag att atc tgg tcc atg agc       1123
Gln Leu Asn Phe Gln Arg Asp Pro Glu Glu Ile Ile Trp Ser Met Ser
            330                 335                 340 cct gtg gtg gat ggt gtg gtg atc cca gat gac cct ttg gtg ctc ctg       1171
Pro Val Val Asp Gly Val Val Ile Pro Asp Asp Pro Leu Val Leu Leu
            345                 350                 355 acc cag ggg aag gtt tca tct gtg ccc tac ctt cta ggt gtc aac aac       1219
Thr Gln Gly Lys Val Ser Ser Val Pro Tyr Leu Leu Gly Val Asn Asn
        360                 365                 370 ctg gaa ttc aat tgg ctc ttg cct tat atc atg aag ttc ccg cta aac       1267
Leu Glu Phe Asn Trp Leu Leu Pro Tyr Ile Met Lys Phe Pro Leu Asn
375                 380                 385                 390 cgg cag gcg atg aga aag gaa acc atc act aag atg ctc tgg agt acc       1315
Arg Gln Ala Met Arg Lys Glu Thr Ile Thr Lys Met Leu Trp Ser Thr
            395                 400                 405 cgc acc ctg ttg aat atc acc aag gag cag gta cca ctt gtg gtg gag       1363
Arg Thr Leu Leu Asn Ile Thr Lys Glu Gln Val Pro Leu Val Val Glu
            410                 415                 420 gag tac ctg gac aat gtc aat gag cat gac tgg aag atg cta cga aac       1411
Glu Tyr Leu Asp Asn Val Asn Glu His Asp Trp Lys Met Leu Arg Asn
            425                 430                 435 cgt atg atg gac ata gtt caa gat gcc act ttc gtg tat gcc aca ctg       1459
Arg Met Met Asp Ile Val Gln Asp Ala Thr Phe Val Tyr Ala Thr Leu
        440                 445                 450 cag act gct cac tac cac cga gat gcc ggc ctc cct gtc tac ctg tat       1507
Gln Thr Ala His Tyr His Arg Asp Ala Gly Leu Pro Val Tyr Leu Tyr
455                 460                 465                 470 gaa ttt gag cac cac gct cgt gga ata atc gtc aaa ccc cgc act gat       1555
Glu Phe Glu His His Ala Arg Gly Ile Ile Val Lys Pro Arg Thr Asp
            475                 480                 485 ggg gca gac cat ggg gat gag atg tac ttc ctc ttt ggg ggc ccc ttc       1603
Gly Ala Asp His Gly Asp Glu Met Tyr Phe Leu Phe Gly Gly Pro Phe
            490                 495                 500 gcc aca ggc ctt tcc atg ggt aag gag aag gca ctt agc ctc cag atg       1651
Ala Thr Gly Leu Ser Met Gly Lys Glu Lys Ala Leu Ser Leu Gln Met
            505                 510                 515 atg aaa tac tgg gcc aac ttt gcc cgc aca gga aac ccc aat gat ggg       1699
Met Lys Tyr Trp Ala Asn Phe Ala Arg Thr Gly Asn Pro Asn Asp Gly
        520                 525                 530 aat ctg ccc tgc tgg cca cgc tac aac aag gat gaa aag tac ctg cag       1747
Asn Leu Pro Cys Trp Pro Arg Tyr Asn Lys Asp Glu Lys Tyr Leu Gln
535                 540                 545                 550 ctg gat ttt acc aca aga gtg ggc atg aag ctc aag gag aag aag atg       1795
```

-continued

```
Leu Asp Phe Thr Thr Arg Val Gly Met Lys Leu Lys Glu Lys Lys Met
                555                 560                 565
gct ttt tgg atg agt ctg tac cag tct caa aga cct gag aag cag agg      1843
Ala Phe Trp Met Ser Leu Tyr Gln Ser Gln Arg Pro Glu Lys Gln Arg
            570                 575                 580 caa ttc taagggtggc tatgcaggaa ggagccaaag aggggtttgc ccccaccatc       1899
Gln Phe caggccctgg ggagactagc catggacata cctggggaca agagttctac ccaagggcga   1959
attcgtttaa acctgcagga ctag                                          1983

<210> SEQ ID NO 2
<211> LENGTH: 584
<212> TYPE: PRT
<213> ORGANISM: Homo sapiens

<400> SEQUENCE: 2

Met Pro Ser Thr Val Leu Pro Ser Thr Val Leu Pro Ser Leu Leu Pro
 1               5                  10                  15

Thr Ala Gly Ala Gly Trp Ser Met Arg Trp Ile Leu Cys Trp Ser Leu
            20                  25                  30

Thr Leu Cys Leu Met Ala Gln Thr Ala Leu Gly Ala Leu His Thr Lys
        35                  40                  45

Arg Pro Gln Val Val Thr Lys Tyr Gly Thr Leu Gln Gly Lys Gln Met
    50                  55                  60

His Val Gly Lys Thr Pro Ile Gln Val Phe Leu Gly Val Pro Phe Ser
65                  70                  75                  80

Arg Pro Pro Leu Gly Ile Leu Arg Phe Ala Pro Pro Glu Pro Pro Glu
                85                  90                  95

Pro Trp Lys Gly Ile Arg Asp Ala Thr Thr Tyr Pro Pro Gly Cys Leu
            100                 105                 110

Gln Glu Ser Trp Gly Gln Leu Ala Ser Met Tyr Val Ser Thr Arg Glu
        115                 120                 125

Arg Tyr Lys Trp Leu Arg Phe Ser Glu Asp Cys Leu Tyr Leu Asn Val
    130                 135                 140

Tyr Ala Pro Ala Arg Ala Pro Gly Asp Pro Gln Leu Pro Val Met Val
145                 150                 155                 160

Trp Phe Pro Gly Gly Ala Phe Ile Val Gly Ala Ser Ser Tyr Glu
                165                 170                 175

Gly Ser Asp Leu Ala Ala Arg Glu Lys Val Val Leu Val Phe Leu Gln
            180                 185                 190

His Arg Leu Gly Ile Phe Gly Phe Leu Ser Thr Asp Asp Ser His Ala
        195                 200                 205

Arg Gly Asn Trp Gly Leu Leu Asp Gln Met Ala Ala Leu Arg Trp Val
    210                 215                 220

Gln Glu Asn Ile Ala Ala Phe Gly Gly Asp Pro Gly Asn Val Thr Leu
225                 230                 235                 240

Phe Gly Gln Ser Ala Gly Ala Met Ser Ile Ser Gly Leu Met Met Ser
                245                 250                 255

Pro Leu Ala Ser Gly Leu Phe His Arg Ala Ile Ser Gln Ser Gly Thr
            260                 265                 270

Ala Leu Phe Arg Leu Phe Ile Thr Ser Asn Pro Leu Lys Val Ala Lys
        275                 280                 285

Lys Val Ala His Leu Ala Gly Cys Asn His Asn Ser Thr Gln Ile Leu
    290                 295                 300
```

-continued

| | | | | | | | | | | | | |
|---|---|---|---|---|---|---|---|---|---|---|---|---|
|Val|Asn|Cys|Leu|Arg|Ala|Leu|Ser|Gly|Thr|Lys|Val|Met Arg Val Ser|
|305| | | |310| | | |315| | | |320|

Asn Lys Met Arg Phe Leu Gln Leu Asn Phe Gln Arg Asp Pro Glu Glu
            325                 330                 335

Ile Ile Trp Ser Met Ser Pro Val Val Asp Gly Val Val Ile Pro Asp
            340                 345                 350

Asp Pro Leu Val Leu Leu Thr Gln Gly Lys Val Ser Ser Val Pro Tyr
        355                 360                 365

Leu Leu Gly Val Asn Asn Leu Glu Phe Asn Trp Leu Leu Pro Tyr Ile
    370                 375                 380

Met Lys Phe Pro Leu Asn Arg Gln Ala Met Arg Lys Glu Thr Ile Thr
385                 390                 395                 400

Lys Met Leu Trp Ser Thr Arg Thr Leu Leu Asn Ile Thr Lys Glu Gln
                405                 410                 415

Val Pro Leu Val Val Glu Glu Tyr Leu Asp Asn Val Asn Glu His Asp
            420                 425                 430

Trp Lys Met Leu Arg Asn Arg Met Met Asp Ile Val Gln Asp Ala Thr
        435                 440                 445

Phe Val Tyr Ala Thr Leu Gln Thr Ala His Tyr His Arg Asp Ala Gly
    450                 455                 460

Leu Pro Val Tyr Leu Tyr Glu Phe Glu His His Ala Arg Gly Ile Ile
465                 470                 475                 480

Val Lys Pro Arg Thr Asp Gly Ala Asp His Gly Asp Glu Met Tyr Phe
                485                 490                 495

Leu Phe Gly Gly Pro Phe Ala Thr Gly Leu Ser Met Gly Lys Glu Lys
            500                 505                 510

Ala Leu Ser Leu Gln Met Met Lys Tyr Trp Ala Asn Phe Ala Arg Thr
        515                 520                 525

Gly Asn Pro Asn Asp Gly Asn Leu Pro Cys Trp Pro Arg Tyr Asn Lys
    530                 535                 540

Asp Glu Lys Tyr Leu Gln Leu Asp Phe Thr Thr Arg Val Gly Met Lys
545                 550                 555                 560

Leu Lys Glu Lys Lys Met Ala Phe Trp Met Ser Leu Tyr Gln Ser Gln
                565                 570                 575

Arg Pro Glu Lys Gln Arg Gln Phe
            580

<210> SEQ ID NO 3
<211> LENGTH: 1752
<212> TYPE: DNA
<213> ORGANISM: Homo sapiens
<220> FEATURE:
<221> NAME/KEY: CDS
<222> LOCATION: (1)...(1752)

<400> SEQUENCE: 3 atg cca tcc aca gtg ttg cca tcc aca gtg ttg cca tca ctc ctg ccc      48
Met Pro Ser Thr Val Leu Pro Ser Thr Val Leu Pro Ser Leu Leu Pro
 1               5                  10                  15 aca gca gga gct ggc tgg agc atg agg tgg att ctg tgc tgg agc ctc      96
Thr Ala Gly Ala Gly Trp Ser Met Arg Trp Ile Leu Cys Trp Ser Leu
            20                  25                  30 acc ctc tgc ctg atg gcg cag acg gcc ttg ggt gcc ttg cac acc aag     144
Thr Leu Cys Leu Met Ala Gln Thr Ala Leu Gly Ala Leu His Thr Lys
        35                  40                  45 agg cct caa gtg gtc acc aaa tat gga acc ctg caa gga aaa cag atg     192
Arg Pro Gln Val Val Thr Lys Tyr Gly Thr Leu Gln Gly Lys Gln Met
    50

```
          50                   55                   60
cat gtg ggg aag aca ccc atc caa gtc ttt tta gga gtc ccc ttc tcc     240
His Val Gly Lys Thr Pro Ile Gln Val Phe Leu Gly Val Pro Phe Ser
 65                  70                  75                  80 aga cct cct cta ggt atc ctc agg ttt gca cct cca gaa ccc ccg gag     288
Arg Pro Pro Leu Gly Ile Leu Arg Phe Ala Pro Pro Glu Pro Pro Glu
                     85                  90                  95 ccc tgg aaa gga atc aga gat gct acc acc tac ccg cct ggg tgc ctg     336
Pro Trp Lys Gly Ile Arg Asp Ala Thr Thr Tyr Pro Pro Gly Cys Leu
            100                 105                 110 cag gag tcc tgg ggc cag ctg gcc tcg atg tac gtc agc acg cgg gaa     384
Gln Glu Ser Trp Gly Gln Leu Ala Ser Met Tyr Val Ser Thr Arg Glu
        115                 120                 125 cgg tac aag tgg ctg cgc ttc agc gag gac tgt ctg tac ctg aac gtg     432
Arg Tyr Lys Trp Leu Arg Phe Ser Glu Asp Cys Leu Tyr Leu Asn Val
    130                 135                 140 tac gcg ccg gcg cgc gcg ccc ggg gat ccc cag ctg cca gtg atg gtc     480
Tyr Ala Pro Ala Arg Ala Pro Gly Asp Pro Gln Leu Pro Val Met Val
145                 150                 155                 160 tgg ttc ccg gga ggc gcc ttc atc gtg ggc gct gct tct tcg tac gag     528
Trp Phe Pro Gly Gly Ala Phe Ile Val Gly Ala Ala Ser Ser Tyr Glu
                165                 170                 175 ggc tct gac ttg gcc gcc cgc gag aaa gtg gtg ctg gtg ttt ctg cag     576
Gly Ser Asp Leu Ala Ala Arg Glu Lys Val Val Leu Val Phe Leu Gln
            180                 185                 190 cac agg ctc ggc atc ttc ggc ttc ctg agc acg gac gac agc cac gcg     624
His Arg Leu Gly Ile Phe Gly Phe Leu Ser Thr Asp Asp Ser His Ala
        195                 200                 205 cgc ggg aac tgg ggg ctg ctg gac cag atg gcg gct ctg cgc tgg gtg     672
Arg Gly Asn Trp Gly Leu Leu Asp Gln Met Ala Ala Leu Arg Trp Val
    210                 215                 220 cag gag aac atc gca gcc ttc ggg gga gac cca gga aat gtg acc ctg     720
Gln Glu Asn Ile Ala Ala Phe Gly Gly Asp Pro Gly Asn Val Thr Leu
225                 230                 235                 240 ttc ggc cag tcg gcg ggg gcc atg agc atc tca gga ctg atg atg tca     768
Phe Gly Gln Ser Ala Gly Ala Met Ser Ile Ser Gly Leu Met Met Ser
                245                 250                 255 ccc cta gcc tcg ggt ctc ttc cat cgg gcc att tcc cag agt ggc acc     816
Pro Leu Ala Ser Gly Leu Phe His Arg Ala Ile Ser Gln Ser Gly Thr
            260                 265                 270 gcg tta ttc aga ctt ttc atc act agt aac cca ctg aaa gtg gcc aag     864
Ala Leu Phe Arg Leu Phe Ile Thr Ser Asn Pro Leu Lys Val Ala Lys
        275                 280                 285 aag gtt gcc cac ctg gct gga tgc aac cac aac agc aca cag atc ctg     912
Lys Val Ala His Leu Ala Gly Cys Asn His Asn Ser Thr Gln Ile Leu
    290                 295                 300 gta aac tgc ctg agg gca cta tca ggg acc aag gtg atg cgt gtg tcc     960
Val Asn Cys Leu Arg Ala Leu Ser Gly Thr Lys Val Met Arg Val Ser
305                 310                 315                 320 aac aag atg aga ttc ctc caa ctg aac ttc cag aga gac ccg gaa gag    1008
Asn Lys Met Arg Phe Leu Gln Leu Asn Phe Gln Arg Asp Pro Glu Glu
                325                 330                 335 att atc tgg tcc atg agc cct gtg gtg gat ggt gtg gtg atc cca gat    1056
Ile Ile Trp Ser Met Ser Pro Val Val Asp Gly Val Val Ile Pro Asp
            340                 345                 350 gac cct ttg gtg ctc ctg acc cag ggg aag gtt tca tct gtg ccc tac    1104
Asp Pro Leu Val Leu Leu Thr Gln Gly Lys Val Ser Ser Val Pro Tyr
        355                 360                 365 ctt cta ggt gtc aac aac ctg gaa ttc aat tgg ctc ttg cct tat atc    1152
```

```
                    Leu Leu Gly Val Asn Asn Leu Glu Phe Asn Trp Leu Leu Pro Tyr Ile
                        370                 375                 380 atg aag ttc ccg cta aac cgg cag gcg atg aga aag gaa acc atc act              1200
Met Lys Phe Pro Leu Asn Arg Gln Ala Met Arg Lys Glu Thr Ile Thr
385                 390                 395                 400 aag atg ctc tgg agt acc cgc acc ctg ttg aat atc acc aag gag cag              1248
Lys Met Leu Trp Ser Thr Arg Thr Leu Leu Asn Ile Thr Lys Glu Gln
                405                 410                 415 gta cca ctt gtg gtg gag gag tac ctg gac aat gtc aat gag cat gac              1296
Val Pro Leu Val Val Glu Glu Tyr Leu Asp Asn Val Asn Glu His Asp
            420                 425                 430 tgg aag atg cta cga aac cgt atg atg gac ata gtt caa gat gcc act              1344
Trp Lys Met Leu Arg Asn Arg Met Met Asp Ile Val Gln Asp Ala Thr
        435                 440                 445 ttc gtg tat gcc aca ctg cag act gct cac tac cac cga gat gcc ggc              1392
Phe Val Tyr Ala Thr Leu Gln Thr Ala His Tyr His Arg Asp Ala Gly
    450                 455                 460 ctc cct gtc tac ctg tat gaa ttt gag cac cac gct cgt gga ata atc              1440
Leu Pro Val Tyr Leu Tyr Glu Phe Glu His His Ala Arg Gly Ile Ile
465                 470                 475                 480 gtc aaa ccc cgc act gat ggg gca gac cat ggg gat gag atg tac ttc              1488
Val Lys Pro Arg Thr Asp Gly Ala Asp His Gly Asp Glu Met Tyr Phe
                485                 490                 495 ctc ttt ggg ggc ccc ttc gcc aca ggc ctt tcc atg ggt aag gag aag              1536
Leu Phe Gly Gly Pro Phe Ala Thr Gly Leu Ser Met Gly Lys Glu Lys
            500                 505                 510 gca ctt agc ctc cag atg atg aaa tac tgg gcc aac ttt gcc cgc aca              1584
Ala Leu Ser Leu Gln Met Met Lys Tyr Trp Ala Asn Phe Ala Arg Thr
        515                 520                 525 gga aac ccc aat gat ggg aat ctg ccc tgc tgg cca cgc tac aac aag              1632
Gly Asn Pro Asn Asp Gly Asn Leu Pro Cys Trp Pro Arg Tyr Asn Lys
    530                 535                 540 gat gaa aag tac ctg cag ctg gat ttt acc aca aga gtg ggc atg aag              1680
Asp Glu Lys Tyr Leu Gln Leu Asp Phe Thr Thr Arg Val Gly Met Lys
545                 550                 555                 560 ctc aag gag aag aag atg gct ttt tgg atg agt ctg tac cag tct caa              1728
Leu Lys Glu Lys Lys Met Ala Phe Trp Met Ser Leu Tyr Gln Ser Gln
                565                 570                 575 aga cct gag aag cag agg caa ttc                                              1752
Arg Pro Glu Lys Gln Arg Gln Phe
            580

<210> SEQ ID NO 4
<211> LENGTH: 16
<212> TYPE: PRT
<213> ORGANISM: Artificial Sequence
<220> FEATURE:
<223> OTHER INFORMATION: Motif
<221> NAME/KEY: VARIANT
<222> LOCATION: 1
<223> OTHER INFORMATION: Xaa may be Gly or Arg
<221> NAME/KEY: VARIANT
<222> LOCATION: 4,5,6,7,9,11,13
<223> OTHER INFORMATION: Xaa may be any amino acid
<221> NAME/KEY: VARIANT
<222> LOCATION: 8
<223> OTHER INFORMATION: Xaa may be Leu, Ile, Met or Val
<221> NAME/KEY: VARIANT
<222> LOCATION: 10
<223> OTHER INFORMATION: Xaa may be Leu, Ile or Val
<221> NAME/KEY: VARIANT
<222> LOCATION: 15
<223> OTHER INFORMATION: Xaa may be Ser, Thr, Ala, or Gly

<400> SEQUENCE: 4
```

```
Phe Xaa Gly Xaa Xaa Xaa Xaa Xaa Xaa Xaa Gly Xaa Ser Xaa Gly
  1               5                   10                  15
```

<210> SEQ ID NO 5
<211> LENGTH: 11
<212> TYPE: PRT
<213> ORGANISM: Artificial Sequence
<220> FEATURE:
<223> OTHER INFORMATION: Motif
<221> NAME/KEY: VARIANT
<222> LOCATION: 1
<223> OTHER INFORMATION: Xaa may be Glu or Asp
<221> NAME/KEY: VARIANT
<222> LOCATION: 5
<223> OTHER INFORMATION: Xaa may be Tyr or Thr
<221> NAME/KEY: VARIANT
<222> LOCATION: 6,8
<223> OTHER INFORMATION: Xaa may be Leu, Ile or Val
<221> NAME/KEY: VARIANT
<222> LOCATION: 7
<223> OTHER INFORMATION: Asp, Asn, or Ser
<221> NAME/KEY: VARIANT
<222> LOCATION: 9
<223> OTHER INFORMATION: Xaa may be Leu, Ile, Phe, Tyr, Trp or Val
<221> NAME/KEY: VARIANT
<222> LOCATION: (10)...(10)
<223> OTHER INFORMATION: Xaa may be any amino acid
<221> NAME/KEY: VARIANT
<222> LOCATION: (11)...(11)
<223> OTHER INFORMATION: Xaa may be Pro, Gln or Arg

<400> SEQUENCE: 5

```
Xaa Asp Cys Leu Xaa Xaa Xaa Xaa Xaa Xaa Xaa
  1               5                   10
```

<210> SEQ ID NO 6
<211> LENGTH: 2456
<212> TYPE: DNA
<213> ORGANISM: Homo sapiens
<220> FEATURE:
<223> OTHER INFORMATION:

<400> SEQUENCE: 6

| | |
|---|---|
| cgccgccgtt ggggctggaa gttcccgcca ggtccgtgcc gggcgagaga gatgctgccc | 60 |
| ggcccgcctc ggcttttgagg cgagagaagt gtcccagacc catttcgcct tgctgacggc | 120 |
| gtcgagcccct ggccagacat gtccacaggg ttctccttcg ggtccgggac tctgggctcc | 180 |
| accaccgtgg ccgccggcgg gaccagcaca ggcggcgttt ctccttcgg aacgggaacg | 240 |
| tctagcaacc cttctgtggg gctcaatttt ggaaatcttg gaagtacttc aactccagca | 300 |
| actacatctg ctccttcaag tggttttgga accgggctct ttggatctaa acctgccact | 360 |
| gggttcactc taggaggaac aaatacaggt gccttgcaca ccaagaggcc tcaagtggtc | 420 |
| accaaatatg gaaccctgca aggaaaacag atgcatgtgg ggaagacacc catccaagtc | 480 |
| tttttaggag tccccttctc cagacctcct ctaggtatcc tcaggtttgc acctccagaa | 540 |
| cccccggagc cctggaaagg aatcagagat gctaccacct acccgcctgg atggagtctc | 600 |
| gctctgtcgc caggctggag tgcagtggca cgatctcggc tcactgcaac ctccgcctcc | 660 |
| cgggttcaag cgagtctcct gcctcagcct ctgagtgtct ggggctacag gtgcctgcag | 720 |
| gagtcctggg gccagctggc ctcgatgtac gtcagcacgc gggaacggta caagtggctg | 780 |
| cgcttcagcg aggactgtct gtacctgaac gtgtacgcgc cggcgcgcgc gcccggggat | 840 |
| ccccagctgc cagtgatggt ctggttcccg ggaggcgcct tcatcgtggg cgctgcttct | 900 |
| tcgtacgagg gctctgactt ggccgcccgc gagaaagtgg tgctggtgtt tctgcagcac | 960 |

-continued

```
aggctcggca tcttcggctt cctgagcacg gacgacagcc acgcgcgcgg gaactggggg   1020
ctgctggacc agatggcggc tctgcgctgg gtgcaggaga acatcgcagc cttcggggga   1080
gacccaggaa atgtgaccct gttcggccag tcggcggggg ccatgagcat ctcaggactg   1140
atgatgtcac ccctagcctc gggtctcttc catcgggcca tttcccagag tggcaccgcg   1200
ttattcagac ttttcatcac tagtaaccca ctgaaagtgg ccaagaaggt tgcccacctg   1260
gctggatgca accacaacag cacacagatc ctggtaaact gcctgagggc actatcaggg   1320
accaaggtga tgcgtgtgtc caacaagatg agattcctcc aactgaactt ccagagagac   1380
ccggaagaga ttatctggtc catgagccct gtggtggatg tgtggtgat cccagatgac    1440 cctttggtgc tcctgaccca ggggaaggtt tcatctgtgc cctaccttct aggtgtcaac   1500
aacctggaat tcaattggct cttgccttat aatatcacca aggagcaggt accacttgtg   1560
gtggaggagt acctggacaa tgtcaatgag catgactgga agatgctacg aaaccgtatg   1620
atggacatag ttcaagatgc cactttcgtg tatgccacac tgcagactgc tcactaccac   1680
cgagaaaccc caatgatggg aatctgccct gctggccacg ctacaacaag gatgaaaagt   1740
acctgcagct ggattttacc acaagagtgg gcatgaagct caaggagaag aagatggctt   1800
tttggatgag tctgtaccag tctcaaagac ctgagaagca gaggcaattc taagggtggc   1860
tatgcaggaa ggagccaaag aggggtttgc ccccaccatc caggccctgg ggagactagc   1920
catggacata cctggggaca agagttctac ccaccccagt ttagaactgc aggagctccc   1980
tgctgcctcc aggccaaagc tagagctttt gcctgttgtg tgggacctgc actgcccttt   2040
ccagcctgac atcccatgat gcccctctac ttcactgttg acatccagtt aggccaggcc   2100
ctgtcaacac cacactgtgc tcagctctcc agcctcagga caacctcttt ttttcccttc   2160
ttcaaatcct cccaccccttc aatgtctcct tgtgactcct tcttatggga ggtcgaccca   2220
gactgccact gccccctgtca ctgcacccag cttggcattt accatccatc ctgctcaacc   2280
ttgttcctgt ctgttcacat tggcctggag gcctagggca ggttgtgaca tggagcaaac   2340
ttttggtagt ttgggatctt ctctcccacc cacacttatc tcccccaggg ccactccaaa   2400
gtctatacac aggggtggtc tcttcaataa agaagtgttg attagaaaaa aaaaaa      2456
```

<210> SEQ ID NO 7
<211> LENGTH: 545
<212> TYPE: PRT
<213> ORGANISM: Homo sapiens
<220> FEATURE:
<223> OTHER INFORMATION:

<400> SEQUENCE: 7

```
Met Ser Thr Gly Phe Ser Phe Gly Ser Gly Thr Leu Gly Ser Thr Thr
 1               5                  10                  15

Val Ala Gly Gly Thr Ser Thr Gly Gly Val Phe Ser Phe Gly Thr
            20                  25                  30

Gly Thr Ser Ser Asn Pro Ser Val Gly Leu Asn Phe Gly Asn Leu Gly
        35                  40                  45

Ser Thr Ser Thr Pro Ala Thr Thr Ser Ala Pro Ser Ser Gly Phe Gly
    50                  55                  60

Thr Gly Leu Phe Gly Ser Lys Pro Ala Thr Gly Phe Thr Leu Gly Gly
65                  70                  75                  80

Thr Asn Thr Gly Ala Leu His Thr Lys Arg Pro Gln Val Val Thr Lys
                85                  90                  95
```

```
Tyr Gly Thr Leu Gln Gly Lys Gln Met His Val Gly Lys Thr Pro Ile
            100                 105                 110

Gln Val Phe Leu Gly Val Pro Phe Ser Arg Pro Pro Leu Gly Ile Leu
        115                 120                 125

Arg Phe Ala Pro Pro Glu Pro Glu Pro Trp Lys Gly Ile Arg Asp
    130                 135                 140

Ala Thr Thr Tyr Pro Pro Gly Trp Ser Leu Ala Leu Ser Pro Gly Trp
145                 150                 155                 160

Ser Ala Val Ala Arg Ser Arg Leu Thr Ala Thr Ser Ala Ser Arg Val
                165                 170                 175

Gln Ala Ser Leu Leu Pro Gln Pro Leu Ser Val Trp Gly Tyr Arg Cys
            180                 185                 190

Leu Gln Glu Ser Trp Gly Gln Leu Ala Ser Met Tyr Val Ser Thr Arg
        195                 200                 205

Glu Arg Tyr Lys Trp Leu Arg Phe Ser Glu Asp Cys Leu Tyr Leu Asn
    210                 215                 220

Val Tyr Ala Pro Ala Arg Ala Pro Gly Asp Pro Gln Leu Pro Val Met
225                 230                 235                 240

Val Trp Phe Pro Gly Gly Ala Phe Ile Val Gly Ala Ala Ser Ser Tyr
                245                 250                 255

Glu Gly Ser Asp Leu Ala Ala Arg Glu Lys Val Val Leu Val Phe Leu
            260                 265                 270

Gln His Arg Leu Gly Ile Phe Gly Phe Leu Ser Thr Asp Asp Ser His
        275                 280                 285

Ala Arg Gly Asn Trp Gly Leu Leu Asp Gln Met Ala Ala Leu Arg Trp
    290                 295                 300

Val Gln Glu Asn Ile Ala Ala Phe Gly Gly Asp Pro Gly Asn Val Thr
305                 310                 315                 320

Leu Phe Gly Gln Ser Ala Gly Ala Met Ser Ile Ser Gly Leu Met Met
                325                 330                 335

Ser Pro Leu Ala Ser Gly Leu Phe His Arg Ala Ile Ser Gln Ser Gly
            340                 345                 350

Thr Ala Leu Phe Arg Leu Phe Ile Thr Ser Asn Pro Leu Lys Val Ala
        355                 360                 365

Lys Lys Val Ala His Leu Ala Gly Cys Asn His Asn Ser Thr Gln Ile
    370                 375                 380

Leu Val Asn Cys Leu Arg Ala Leu Ser Gly Thr Lys Val Met Arg Val
385                 390                 395                 400

Ser Asn Lys Met Arg Phe Leu Gln Leu Asn Phe Gln Arg Asp Pro Glu
                405                 410                 415

Glu Ile Ile Trp Ser Met Ser Pro Val Val Asp Gly Val Val Ile Pro
            420                 425                 430

Asp Asp Pro Leu Val Leu Thr Gln Gly Lys Val Ser Ser Val Pro
        435                 440                 445

Tyr Leu Leu Gly Val Asn Asn Leu Glu Phe Asn Trp Leu Leu Pro Tyr
    450                 455                 460

Asn Ile Thr Lys Glu Gln Val Pro Leu Val Val Glu Glu Tyr Leu Asp
465                 470                 475                 480

Asn Val Asn Glu His Asp Trp Lys Met Leu Arg Asn Arg Met Met Asp
                485                 490                 495

Ile Val Gln Asp Ala Thr Phe Val Tyr Ala Thr Leu Gln Thr Ala His
            500                 505                 510

Tyr His Arg Glu Thr Pro Met Met Gly Ile Cys Pro Ala Gly His Ala
```

```
                    515                 520                 525
Thr Thr Arg Met Lys Ser Thr Cys Ser Trp Ile Leu Pro Gln Glu Trp
    530                 535                 540
Ala
545
```

METHODS FOR SCREENING COMPOUNDS THAT BIND HUMAN COE-2

RELATED APPLICATIONS

The present application claims priority to U.S. provisional application Ser. No. 60/250,929, filed on Nov. 30, 2000, entitled "METHODS OF USING 18903 TO TREAT PAIN AND PAIN-RELATED DISORDERS," the entire contents of which are incorporated herein by reference.

BACKGROUND OF THE INVENTION

The metabolism of lipids plays a central role in many higher eukaryotic cellular processes. In addition to their importance in energy production and storage, lipid compounds have been found to be key components in several signaling pathways which regulate pain and inflammation. An early event in the inflammatory response and attendant pain stimuli is the cellular release of lipid-derived mediators which alter the function and biochemistry of surrounding cells and tissues. The ensuing biological responses, as well as much of the pathogenesis which is attributed to inflammation and pain, are thought to be dependent upon the effects of these newly-formed mediators on adjacent cells within the affected region. The synthesis of many lipid mediators is initiated by the cleavage of complex phospholipid precursor molecules to release long-chain fatty acids, such as arachidonate. The availability of free arachidonic acid, a $C_{20}$ "eicosanoid" fatty acid having four double bonds, represents the rate-limiting step in the formation of a host of bioactive eicosanoid derivatives (e.g., leukotrienes, prostaglandins and thromboxanes) which mediate the inflammatory response and the production of pain and fever (Goodman and Gilman *The Pharmacological Basis of Therapeutics* (A. Goodman Gilman et al., eds.), Pergamon Press, New York (1990), pp. 600–611; Stryer, *Biochemistry* (2nd edition), W. H. Freeman and Co., New York (1981), pp. 853–854; Voet and Voet, *Biochemistry*, John Wiley & Sons, New York (1990) pp. 658–665).

The eicosanoids have a broad spectrum of biological activities related to inflammation and pain, including local vasodialation, activation of neutrophils and platelets, inhibition of platelet aggregation, as well as central nervous system and afferent nerve function. Indeed, one of the earliest analgesics to be identified, aspirin, is known to function by suppressing the synthesis of prostaglandins from arachidonic acid by prostaglandin endoperoxide synthase.

Concomitant with arachidonate release, lysophospholipids are formed. Originally regarded as merely intermediates in lipid biosynthesis (Kent (1995) *Anal. Rev. Biochem.* 64:315–343), phosphatidic acid (PA), lysophosphatidic acid (LPA), and 1-alkyl-2-acetyl-glycero-3-phosphocholine (Platelet Activating Factor, PAF) have also been identified as phospholipid signaling molecules that affect a wide range of biological responses which include inflammation and pain (McPhail et al., (1995) *Proc. Natl. Acad. Sci. USA* 92:7931–7935; Williger et al., (1995) *J. Biol. Chem.* 270: 29656–29659, Moolenaar (1995) *Curr. Opin. Cell Biol.* 7:203–210, and Moolenaar (1995) *J. Biol. Chem.* 270: 12949–12952).

Lipid metabolism is known to also yield components of other pain-related pathways which directly affect nerve termini. The lipid-derived endocannabinoids are endogenous cannabinoid compounds which mediate a number of cellular responses related to pain and inflammation through the cannabinoid (CB) receptors. Closely related to arachidonic compounds, endocannabinoids such as arachidonic acid ethanolamide (anandamide) and 2-arachidoloylglycerol (2-AG) are able to modulate the synthesis, release, and activity of neurotransmitters such as dopamine, GABA, acetylcholine, noradrenaline, and glutamate (Breivogel and Childers (1998) *Neurobiol. Dis.* 5:417–431, and Martin et al. (1999) *Life Sciences* 65:573–595, Di Marzo (1999) *Life Sciences* 65:645–655, Burstein et al. (1994) *Biochemical Pharmacology* 48:1253–1264, and Pop (1999) *Curr. Opinion Chem. Biol.* 3:418–425).

It appears that each of the cell types involved in inflammatory and pain response produce and secrete a unique subset of lipid mediators. The quantities and nature of the metabolites depend on which enzymes and precursor phospholipid pools are available to inflammatory cells. Elucidation and molecular characterization of additional molecules that participate in the rich network of biochemical pathways which govern these responses will provide novel therapeutic approaches for pain and inflammatory disorders.

SUMMARY OF THE INVENTION

The present invention is based, at least in part, on the discovery of novel carboxylesterase family members, referred to herein as "Carboxylesterase-2" or "COE-2" nucleic acid and protein molecules. The COE-2 nucleic acid and protein molecules of the present invention are useful as modulating agents in regulating a variety of cellular processes, including the metabolism of various lipid and fatty acid compounds which are involved in pain and/or inflammation signaling, e.g., arachidonic acid and related eicosanoids, diacyl glycerol, lysophosphatidic acid, lysophosphatidylcholine, and endocannabinoids, e.g., anandamide and 2-AG. The COE-2 nucleic acid and protein molecules of the present invention may also have utility for a number of related functions including, general intra- or inter-cellular signaling; gene expression; and cellular growth or differentiation, as well as hydrolysis of endogenous and exogenous compounds; detoxification or activation of drugs, pro-drugs, toxins, or carcinogens. Accordingly, in one aspect, this invention provides isolated nucleic acid molecules encoding COE-2 proteins or biologically active portions thereof, as well as nucleic acid fragments suitable as primers or hybridization probes for the detection of COE-2-encoding nucleic acids.

In one embodiment, the invention features an isolated nucleic acid molecule that includes the nucleotide sequence set forth in SEQ ID NO:1 or SEQ ID NO:3. In another embodiment, the invention features an isolated nucleic acid molecule that encodes a polypeptide including the amino acid sequence set forth in SEQ ID NO:2.

In still other embodiments, the invention features isolated nucleic acid molecules including nucleotide sequences that are substantially identical (e.g., 93% identical) to the entire nucleotide sequence set forth as SEQ ID NO:1 or SEQ ID NO:3. The invention further features isolated nucleic acid molecules including at least 829 contiguous nucleotides of the nucleotide sequence set forth as SEQ ID NO:1 or SEQ ID NO:3. In another embodiment, the invention features isolated nucleic acid molecules which encode a polypeptide including an amino acid sequence that is substantially identical (e.g., 63% identical) to the entire amino acid sequence set forth as SEQ ID NO:2. Also featured are nucleic acid molecules which encode allelic variants of the polypeptide having the amino acid sequence set forth as SEQ ID NO:2. In addition to isolated nucleic acid molecules encoding full-length polypeptides, the present invention also features nucleic acid molecules which encode fragments, for example, biologically active or antigenic fragments, of the full-length polypeptides of the present invention (e.g., fragments including at least 273 contiguous amino acid residues of the amino acid sequence of SEQ ID NO:2). In still other embodiments, the invention features nucleic acid molecules that are complementary to, antisense to, or hybridize under stringent conditions to the isolated nucleic acid molecules described herein.

In a related aspect, the invention provides vectors including the isolated nucleic acid molecules described herein (e.g., COE-2-encoding nucleic acid molecules). Such vectors can optionally include nucleotide sequences encoding heterologous polypeptides. Also featured are host cells including such vectors (e.g., host cells including vectors suitable for producing COE-2 nucleic acid molecules and polypeptides).

In another aspect, the invention features isolated COE-2 polypeptides and/or biologically active or antigenic fragments thereof. Exemplary embodiments feature a polypeptide including the amino acid sequence set forth as SEQ ID NO:2, a polypeptide including an amino acid sequence at least 63% identical to the entire amino acid sequence set forth as SEQ ID NO:2, a polypeptide encoded by a nucleic acid molecule including a nucleotide sequence at least 93% identical to the entire nucleotide sequence set forth as SEQ ID NO:1 or SEQ ID NO:3. Also featured are fragments of the full-length polypeptides described herein (e.g., fragments including at least 273 contiguous amino acid residues of the sequence set forth as SEQ ID NO:2) as well as allelic variants of the polypeptide having the amino acid sequence set forth as SEQ ID NO:2.

The COE-2 polypeptides and/or biologically active or antigenic fragments thereof, are useful, for example, as reagents or targets in assays applicable to treatment and/or diagnosis of COE-2 mediated or related disorders. In one embodiment, a COE-2 polypeptide or fragment thereof has a COE-2 activity. In another embodiment, a COE-2 polypeptide or fragment thereof has a carboxylesterase domain and optionally, has a COE-2 activity. In a related aspect, the invention features antibodies (e.g., antibodies which specifically bind to any one of the polypeptides, as described herein) as well as fusion polypeptides including all or a fragment of a polypeptide described herein.

The present invention further features methods for detecting COE-2 polypeptides and/or COE-2 nucleic acid molecules, such methods featuring, for example, a probe, primer or antibody described herein. Also featured are kits for the detection of COE-2 polypeptides and/or COE-2 nucleic acid molecules. In a related aspect, the invention features methods for identifying compounds which bind to and/or modulate the activity of a COE-2 polypeptide or COE-2 nucleic acid molecule described herein. Also featured are methods for modulating a COE-2 activity.

In other embodiments, the present invention includes a method of identifying a nucleic acid molecule associated with an inflammatory or pain disorder which comprises contacting a sample comprising nucleic acid molecules with a hybridization probe comprising at least 25 contiguous nucleotides of SEQ ID NO:1, followed by detecting the presence of a nucleic acid molecule in said sample that hybridizes to said probe, thereby identifying a nucleic acid molecule associated with an inflammatory or pain disorder.

In a related embodiment, the hybridization probe is detectably labeled. In a further related embodiment, the sample comprising nucleic acid molecules is subjected to agarose gel electrophoresis and southern blotting and/or northern blotting prior to contacting with said hybridization probe. In yet another embodiment detection is accomplished by in situ hybridization.

In other embodiments, the present invention includes a method of identifying a nucleic acid molecule associated with an inflammatory or pain disorder. The method includes contacting a sample of nucleic acid molecules with a first and a second amplification primer, the first primer comprising at least 25 contiguous nucleotides of SEQ ID NO:1 or a complement thereof, the said second primer comprising at least 25 contiguous nucleotides from the complement of SEQ ID NO:1 or a complement thereof, then incubating the sample under conditions that allow nucleic acid amplification and finally detecting the presence of a nucleic acid molecule in the sample that is amplified, thereby identifying a nucleic acid molecule associated with an inflammatory or pain disorder. In one embodiment, the sample comprises nucleic acid molecules and is subjected to agarose gel electrophoresis after the incubation step. In other embodiment, the method used to detect mRNA and/or genomic DNA in a sample.

In another aspect, the invention provides a method of identifying a polypeptide associated with an inflammatory or pain disorder. The method includes contacting a sample containing polypeptides with a binding substance which specifically binds to COE-2, then detecting the presence of a polypeptide in the sample which binds to the COE-2 binding substance, thereby identifying a polypeptide associated with an inflammatory or pain disorder. In one embodiment, the binding substance is an antibody which may or may not be detectably labeled.

In yet another aspect the invention features a method of identifying a subject having an inflammatory or pain disorder, or at risk for developing an inflammatory or pain disorder. The method includes contacting a sample obtained from the subject which contains nucleic acid molecules with a hybridization probe comprising at least 25 contiguous nucleotides of SEQ ID NO:1, and detecting the presence of a nucleic acid molecule in the sample that hybridizes to the probe, thereby identifying a subject having an inflammatory or pain disorder, or at risk for developing an inflammatory or pain disorder. In one embodiment, the hybridization probe is detectably labeled. In one embodiment, the sample comprising nucleic acid molecules is subjected to agarose gel electrophoresis and southern an/or northern blotting prior to contacting with the hybridization probe. In another embodiment, detection is accomplished by in situ hybridization.

In a further aspect, the invention provides a method of identifying a subject having an inflammatory or pain disorder, or at risk for developing an inflammatory or pain disorder. The method includes contacting a sample obtained from the subject comprising nucleic acid molecules with a first and a second amplification primer, the first primer comprising at least 25 contiguous nucleotides of SEQ ID NO:1 and the second primer comprising at least 25 contiguous nucleotides from the complement of SEQ ID NO:1; incubating the sample under conditions that allow nucleic acid amplification; and detecting the presence of a nucleic acid molecule in the sample that is amplified, thus identifying a subject having an inflammatory or pain disorder, or at risk for developing an inflammatory or pain disorder. In one embodiment, the sample containing nucleic acid molecules is subjected to agarose gel electrophoresis after the incubation step. In another embodiment, the method is used to detect mRNA and/or genomic DNA in the sample.

In another aspect, the invention provides a method of identifying a subject having an inflammatory or pain disorder, or at risk for developing an inflammatory or pain disorder which involves obtaining a sample from the subject which contains polypeptides, contacting the sample with a COE-2 binding substance, and subsequently detecting the presence of a polypeptide in the sample that binds to the COE-2 binding substance, thereby identifying a subject having an inflammatory or pain disorder, or at risk for developing an inflammatory or pain disorder. In one embodiment, the binding substance is an antibody which may or may not be detectably labeled.

The invention also provides methods for identifying compounds capable of treating an inflammatory or pain disorder which is characterized by aberrant COE-2 nucleic acid expression or COE-2 polypeptide activity. Such methods include assaying the ability of a compound to modulate COE-2 nucleic acid expression or COE-2 polypeptide activity, thereby identifying a compound capable of treating an inflammatory or pain disorder which is characterized by aberrant COE-2 nucleic acid expression or COE-2 polypeptide activity. In one embodiment, the pain disorder is chronic pain and/or is a neuropathic pain. In yet another related embodiment, the ability of the compound to modulate the activity of the COE-2 polypeptide is determined by detecting the induction of an intracellular second messenger.

In another aspect the invention provides methods for treating a subject having an inflammatory or pain disorder which is characterized by aberrant COE-2 polypeptide activity or aberrant COE-2 nucleic acid expression, e.g. chronic pain and/or a neuropathic pain. Such methods involve administering to the subject a COE-2 modulator, thereby treating said subject having an inflammatory or pain disorder. The COE-2 modulator may be administered in a pharmaceutically acceptable formulation and/or may be administered using a gene therapy vector. In one embodiment, the COE-2 modulator is capable of modulating COE-2 polypeptide activity. For example, the COE-2 modulator may be a small molecule; an anti-COE-2 antibody; a COE-2 polypeptide which comprises the amino acid sequence of SEQ ID NO:2, or a fragment thereof; a COE-2 polypeptide comprising an amino acid sequence which is at least 63 percent identical to the amino acid sequence of SEQ ID NO:2; or an isolated naturally occurring allelic variant of a polypeptide consisting of the amino acid sequence of SEQ ID NO:2.

In a further embodiment, the COE-2 modulator is capable of modulating COE-2 nucleic acid expression. For example, the COE-2 modulator may be a small molecule; an antisense COE-2 nucleic acid molecule; a ribozyme; a nucleic acid molecule comprising the nucleotide sequence of SEQ ID NO:1, or a fragment thereof; a nucleic acid molecule encoding a polypeptide comprising an amino acid sequence which is at least 90 percent identical to the amino acid sequence of SEQ ID NO:2; or a nucleic acid molecule encoding a naturally occurring allelic variant of a polypeptide comprising the amino acid sequence of SEQ ID NO:2.

In another aspect the invention provides a method for identifying a compound capable of modulating a pain response associated activity in a cell. The method includes contacting the cell with a test compound, and subsequently assaying the ability of the test compound to modulate the expression of a COE-2 nucleic acid or the activity of a COE-2 polypeptide; thus identifying a compound capable of modulating a pain response associated activity in a cell. In one embodiment, the pain response associated activity is release of a lipid mediator, and/or release of a neurotransmitter.

Other features and advantages of the invention will be apparent from the following detailed description and claims.

BRIEF DESCRIPTION OF THE DRAWINGS

FIGS. 2A–2C depict the results of a search in the HMM database, using the amino acid sequence of human COE-2. This search resulted in the identification of a carboxylesterase domain (COesterase) in the human COE-2 protein.

FIGS. 3A–3D depict a global alignment of the cDNA nucleotide sequence of human COE-2 with that of human PRO873 (Accession No. Z34105 in the Patent Nucleotide database) (SEQ ID NO:6).

FIGS. 4A–4C depict a global alignment of the amino acid sequence of human COE-2 with that of human PRO873 (SEQ ID NO:7).

FIGS. 7A-1 through 7B depict the expression of COE-2 in various normal and tumor tissues as determined with TAQman assays. High expression is evident in brain.

DETAILED DESCRIPTION OF THE INVENTION

Figure 5A:
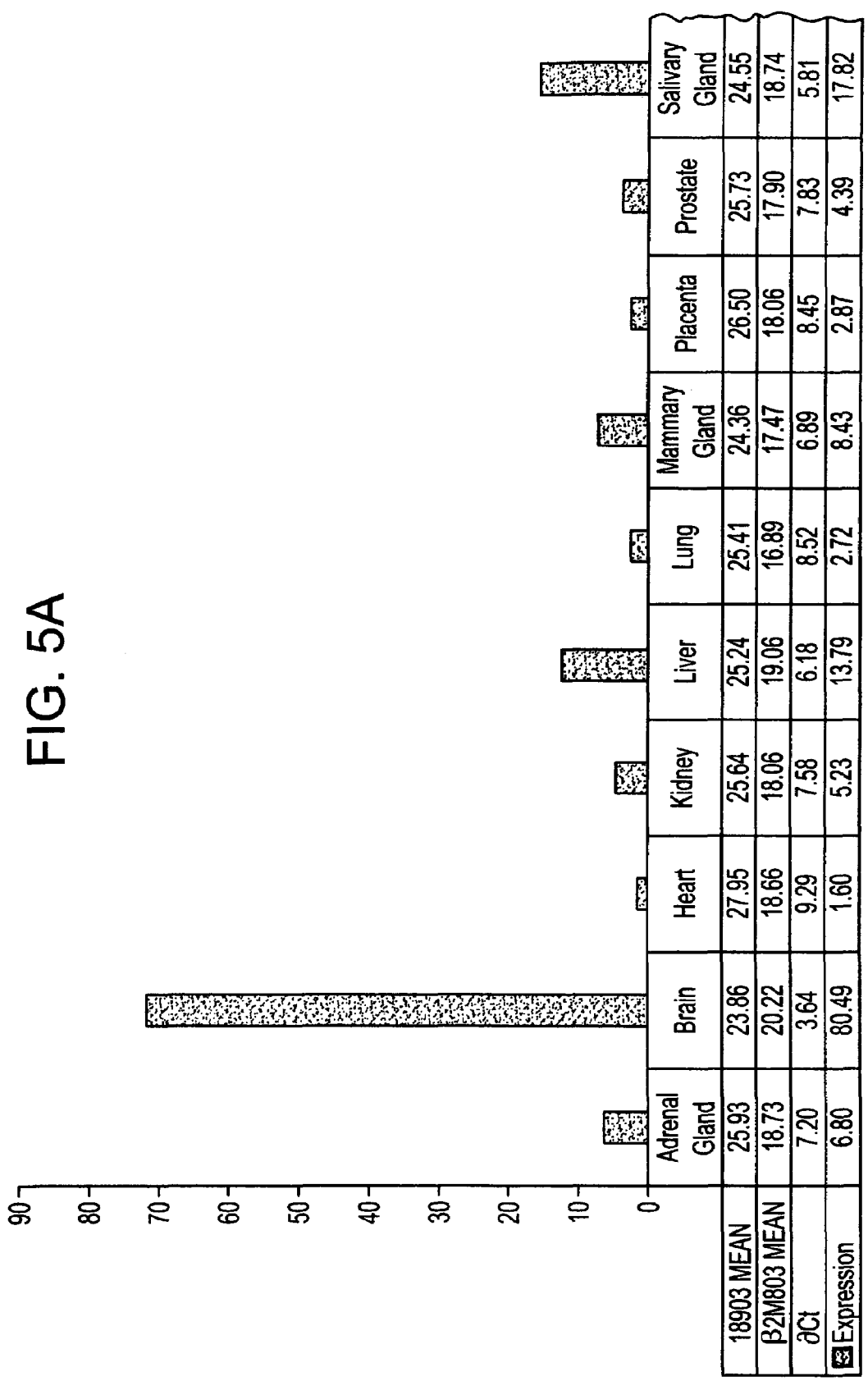
FIGS. 5A–5B the expression of COE-2 in various tissues as determined with TAQman assays. Relatively high expression in brain and spinal cord is evident.
Figure 5B:
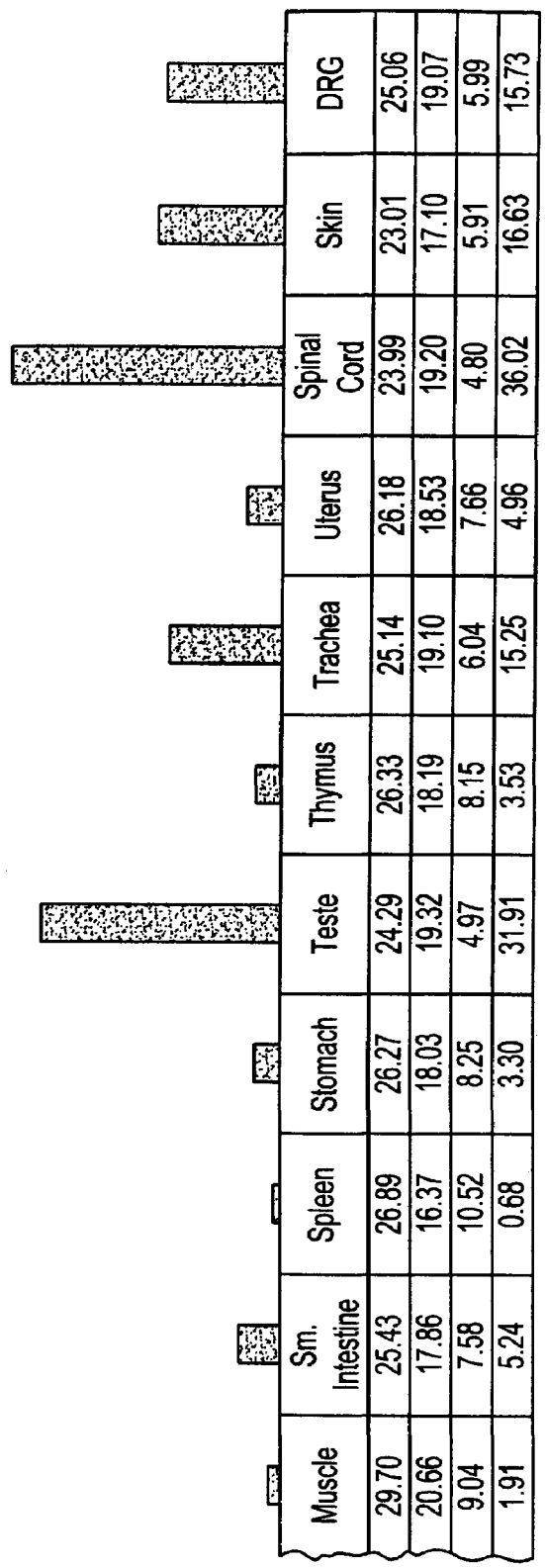
Figure 6A:
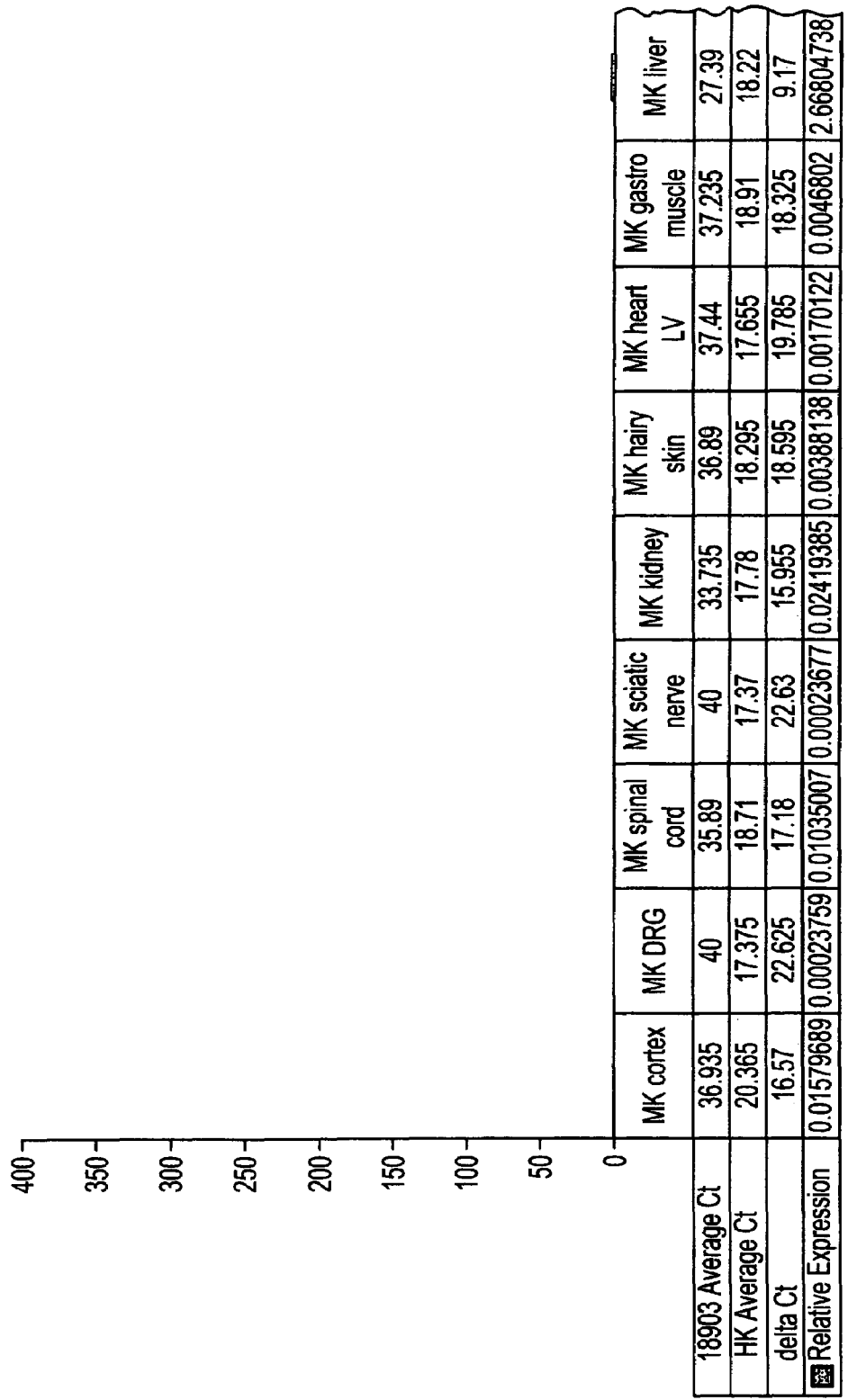
FIGS. 6A–6B the expression of COE-2 in tissues from various organisms as determined with TAQman assays. High expression is evident in brain and spinal cord.
Figure 6B:
Figures 1, 7A:
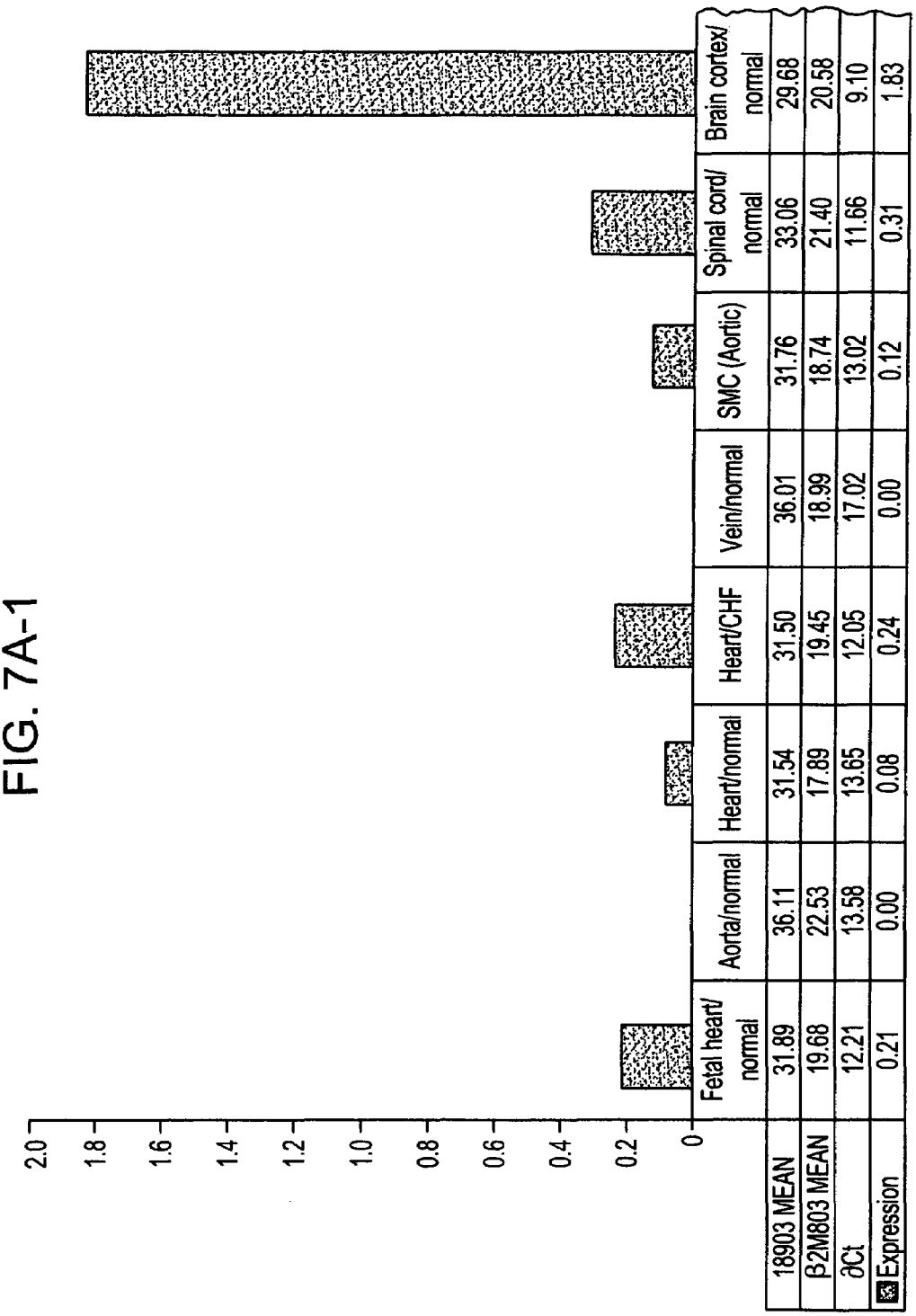
Figures 2, 7A:
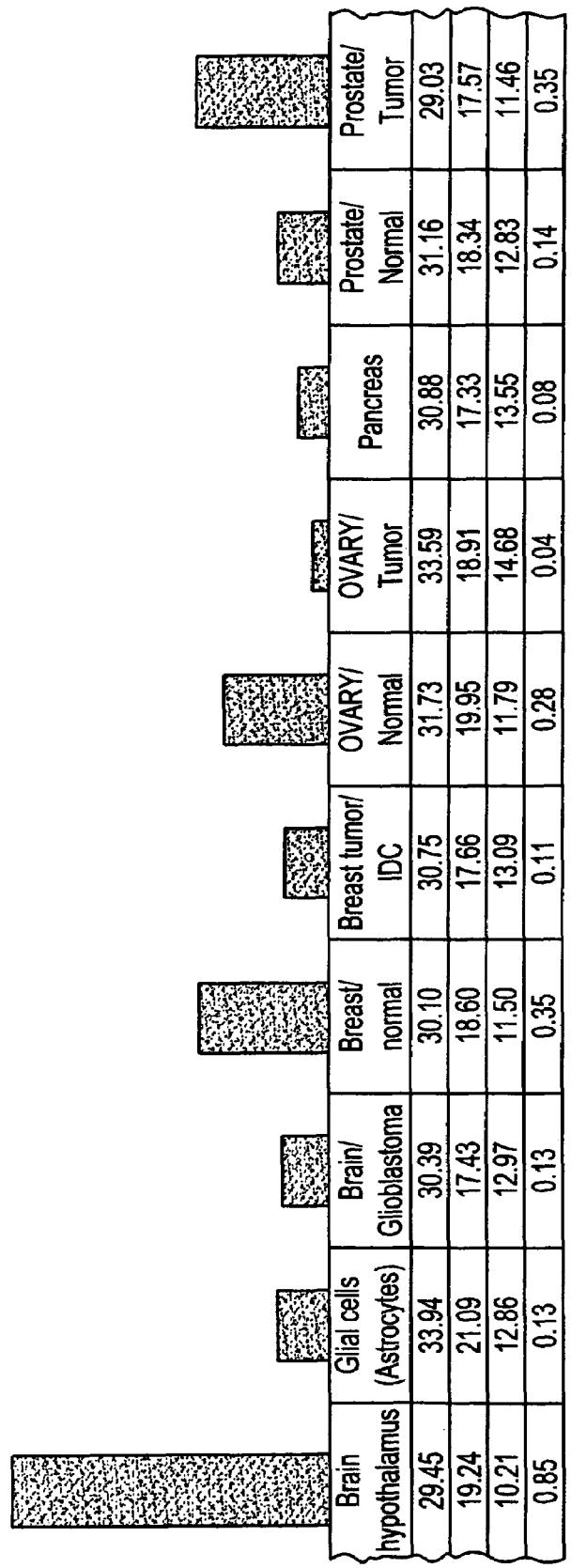
Figures 3, 7A:
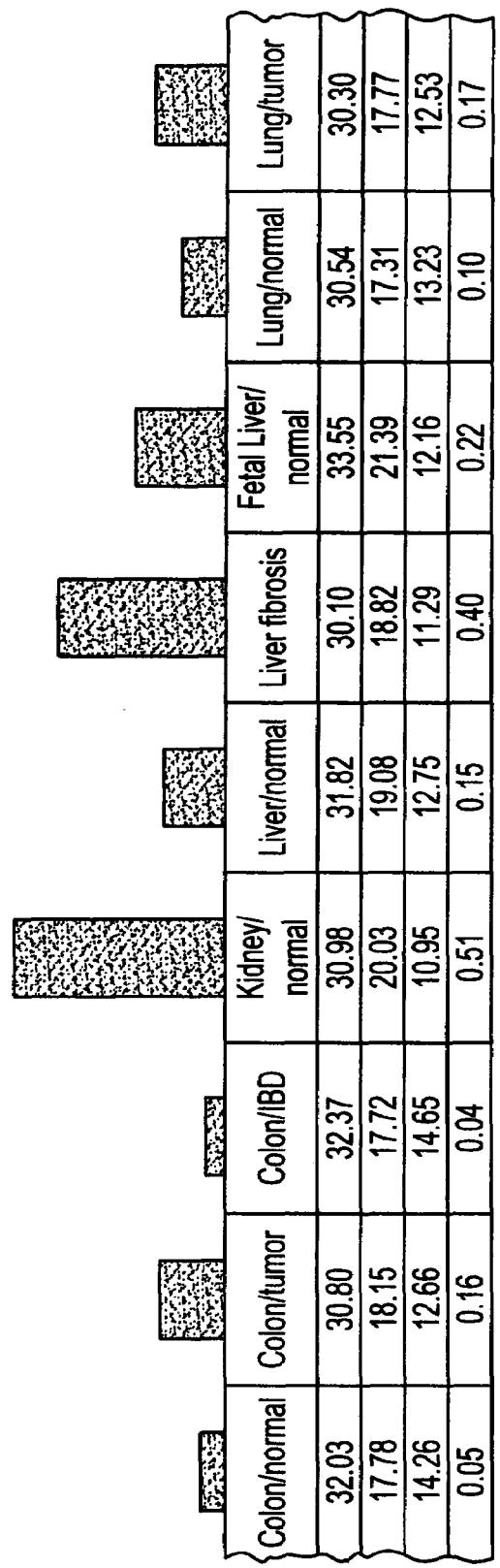

The present invention is based, at least in part, on the discovery of novel carboxylesterase family members, referred to herein as "Carboxylesterase-2" or "COE-2" nucleic acid and protein molecules. These novel molecules are capable of participating in the metabolism of various lipid and fatty acid compounds which are involved in pain and/or inflammation signaling, e.g., arachidonic acid and related eicosanoids, diacyl glycerol, lysophosphatidic acid, lysophosphatidylcholine, and endocannabinoids, e.g., anandamide and 2-AG. The present invention is also based, at least in part, on the discovery that these molecules are highly expressed in tissues which contain afferent neurons, particularly brain and spinal cord tissue (FIGS. 5–7). In mammals, the initial detection of noxious chemical, mechanical, or thermal stimuli, a process referred to as "nociception", occurs predominantly at the peripheral terminals of specialized, small diameter primary afferent neurons, called polymodal nociceptors. These afferent neurons transmit the information to the central nervous system, evoking a perception of pain or discomfort and initiating appropriate protective reflexes. Thus, the COE-2 molecules of the present invention may participate in pain-signaling mechanisms and, as such, may modulate pain elicitation and provide novel diagnostic targets and therapeutic agents for inflammatory or pain disorders.

As used herein, the term "carboxylesterase-associated disorder" includes disorders, diseases or conditions which are caused or characterized by a misregulation (e.g., downregulation or upregulation) of carboxylesterase activity. As further used herein, a carboxylesterase-associated disorder includes a disease or condition which is not necessarily caused by a misregulation (e.g., downregulation or upregulation) of carboxylesterase activity, but which can be treated, at least in part, by altering or augmenting the activity of a carboxylesterase activity in the subject or by fortifying the subject with a carboxylesterase or with metabolites related to normal carboxylesterase activity. Carboxylesterase-associated disorders can detrimentally affect normal lipid metabolism and, hence, the many signaling processes which depend upon lipid-derived metabolites such as arachidonic acid and related eicosanoids, diacyl glycerol, lysophosphatidic acid, lysophosphatidylcholine, and endocannabinoids, e.g., anandamide and 2-AG. Hence, the COE-2 molecules provide novel diagnostic targets and therapeutic agents to control carboxylase-associated disorders such as pain disorders, e.g., the exaggerated pain response elicited during various forms of tissue injury, e.g., inflammation, infection, and ischemia, usually referred to as hyperalgesia (described in, for example, Fields, H. L. (1987) *Pain*, New York: McGraw-Hill). Moreover, the COE-2 molecules provide novel diagnostic targets and therapeutic agents to control pain associated with musculoskeletal disorders, e.g., joint pain; tooth pain; headaches; or pain associated with surgery, rheumatoid arthritis, viral infection, allergic reaction, asthma, chronic pain, chronic pancreatitis, somatoform disorders, fibromyalgia syndrome, and the like.

Other carboxylesterase-associated disorders include those which stem from, or present themselves through aberrant levels of lysophosphatidic acid (LPA) and related metabolites. Examples of such carboxylesterase-associated disorders include a variety of tumors and cancers (e.g., ovarian cancer, see e.g., Fang et al. (2000) *Ann NY Acad Sci* 905:188–208), as well as apoptosis, cytoskeletal abberancies, and the like. Further examples of carboxylesterase-associated disorders include those which can be attributed to abberant levels of a particular lipid metabolite, such as the eicosanoids and prostaglandins. Such disorders include abberant blood pressure, aberrant blood clotting, misregulation of various reproductive functions, e.g., induction of labor, and misregulation of the sleep/wake cycle.

Still further examples of carboxylesterase-associated disorders include those which are related to aberrant expression of endocannabinoids, such as anandamide and 2-AG. Such disorders include those relating to pain, vasodialation, and hypotension, as well as those which are behavioral, e.g., alcohol dependence (see, e.g., Hungund and Basavarajappa, (2000) *Alcohol and Alchoholism* 35:126–133) or those in which detrimental effect(s) are the result of separate disorders or injuries, e.g., multiple sclerosis or spinal cord injury. COE-2-associated or related disorders also include disorders affecting tissues in which COE-2 protein is expressed.

Carboxylesterase-associated disorders also include inflammatory disorders, examples of which include, but are not limited to viral infection, inflammatory bowel disease, ulcerative colitis, Crohn's disease, leukocyte adhesion deficiency II syndrome, peritonitis, chronic obstructive pulmonary disease, lung inflammation, asthma, acute appendicitis, septic shock, nephritis, amyloidosis, rheumatoid arthritis, chronic bronchitis, sarcoidosis, scleroderma, lupus, polymyositis, Reiter's syndrome, psoriasis, pelvic inflammatory disease, inflammatory breast disease, and orbital inflammatory disease.

The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin or alternatively, can contain homologues of non-human origin, e.g., rat or mouse proteins. Members of a family can also have common functional characteristics.

In one embodiment, the COE-2 proteins of the present invention contain at least one transmembrane domain. As used herein, the term "transmembrane domain" includes an amino acid sequence having at least about 10, preferably about 13, preferably about 16, more preferably about 19, 21, 23, 25, 30, 35 or 40 amino acid residues, of which at least about 50–60%, 60–70%, preferably about 70–80% more preferably about 80–90%, or about 90 of the amino acid residues contain non-polar side chains, for example, alanine, valine, leucine, isoleucine, proline, phenylalanine, tryptophan, and methionine. A transmembrane domain is lipophilic in nature. Transmembrane domains are described in, for example, Zagotta et al., (1996) *Annual Rev. Neurosci.* 19:235–63, the contents of which are incorporated herein by reference. In a preferred embodiment, a COE-2 protein of the present invention has more than one transmembrane domain, preferably 2 transmembrane domains. Transmembrane domains were identified at about amino acids 26–45 and 245–263 of SEQ ID NO:2 (see FIG. 1).

Members of the COE-2 family of proteins may also be identified by the presence of at least one "carboxylesterase domain" in the protein or corresponding nucleic acid molecule. As used herein, the term "carboxylesterase domain" includes a protein domain having at least about 440–600 amino acid residues and a bit score of at least 440 when compared against a carboxylesterase Hidden Markov Model (HMM), e.g., PFAM Accession Number PF00135. Preferably, a carboxylesterase domain includes a protein having an amino acid sequence of about 505–585, 525–565, 535–555, or more preferably about 545 amino acid residues, and a bit score of at least 250, 350, 450, 500, or more preferably, 558.6. To identify the presence of a carboxylesterase domain in a COE-2 protein, and make the determination that a protein of interest has a particular profile, the amino acid sequence of the protein is searched against a database of known protein domains (e.g., the HMM database). The carboxylesterase domain (HMM) has been assigned the PFAM Accession number PF00135 (see the Pfam website) and the InterPro Accession number IPR002018 (see the InterPro website). A search was performed against the HMM database resulting in the identification of a carboxylesterase domain in the amino acid sequence of human COE-2 at about residues 25–569 of SEQ ID NO:2. The results of the search are set forth in FIG. 2.

A description of the Pfam database can be found in Sonhammer et al. (1997) *Proteins* 28:405–420, and a detailed description of HMMs can be found, for example, in Gribskov et al. (1990) *Meth. Enzymol.* 183:146–159; Gribskov et al. (1987) *Proc. Natl. Acad. Sci. USA* 84:4355–4358; Krogh et al.(1994) J. Mol. Biol. 235:1501–1531; and Stultz et al. (1993) Protein Sci. 2:305–314, the contents of which are incorporated herein by reference.

In another embodiment, a COE-2 family member of the present invention is identified based on the presence of one or more "carboxylesterase type B1 signature motif" sequences in the protein or corresponding nucleic acid molecule. As used herein, a "carboxylesterase type B1 signature motif" includes a motif having the consensus sequence F-[GR]-G-X(4)-[LIVM]-X-[LIV]-X-G-X-S-[STAG]-G (SEQ ID NO:4). In another embodiment, a COE-2 family member of the present invention is identified based on the presence of one or more "carboxylesterase type B2 signature motif" sequences in the protein or corresponding nucleic acid molecule. As used herein, a "carboxylesterase type B2 signature motif" includes a motif having the consensus sequence [ED]-D-C-L-[YT]-[LIV]-[DNS]-[LIV]-[LIVFYW]-X-[PQR] (SEQ ID NO:5). Carboxylesterase type B1 signature motifs and carboxylesterase type B2 signature motifs are described under Prosite entry number PDOC00112 (see the Prosite website). A carboxylesterase type B1 signature motif was identified within the human COE-2 protein (SEQ ID NO:2) at about residues 231–246. A carboxylesterase type B2 signature motif was identified within the human COE-2 protein (SEQ ID NO:2) at about residues 137–147. The consensus sequences described herein are described according to standard Prosite Signature designation (e.g., all amino acids are indicated according to their universal single letter designation; X designates any amino acid; X(n) designates any n amino acids, e.g., X(2) designates any 2 amino acids; [LIVM] indicates any one of the amino acids appearing within the brackets, e.g., any one of L, I, V, or M, in the alternative, any one of Leu, Ile, Val, or Met.).

Isolated proteins of the present invention, preferably COE-2 proteins, have an amino acid sequence sufficiently identical to the amino acid sequence of SEQ ID NO:2, or are encoded by a nucleotide sequence sufficiently identical to SEQ ID NO:1 or 3. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains having at least 50%, 55%, 60%, 65%, 70%, 75%, 80%, 85%, 85%, 90%, 93%, 95%, 96%, 97%, 98%, 99% or more homology or identity across the amino acid sequences of the domains and contain at least one and preferably two structural domains or motifs, are defined herein as sufficiently identical. Furthermore, amino acid or nucleotide sequences which share at least 50%, 55%, 60%, 65%, 70%, 75%, 80%, 85%, 85%, 90%, 93%, 94%, 95%, 96%, 97%, 98%, 99% or more homology or identity and share a common functional activity are defined herein as sufficiently identical.

In a preferred embodiment, a COE-2 protein includes at least one or more of the following four features: a carboxylesterase domain, a transmembrane domain, a carboxylesterase B1 signature motif, a carboxylesterase B2 signature motif, and has an amino acid sequence at least about 50%, 55%, 60%, 63%, 65%, 70%, 75%, 80%, 85%, 85%, 90%, 93%, 94%, 95%, 96%, 97%, 98%, 99% or more homologous or identical to the amino acid sequence of SEQ ID NO:2. In yet another preferred embodiment, a COE-2 protein includes at least one or more of the following four features: a carboxylesterase domain, a transmembrane domain, a carboxylesterase B1 signature motif, a carboxylesterase B2 signature motif, and is encoded by a nucleic acid molecule having a nucleotide sequence which hybridizes under stringent hybridization conditions to a complement of a nucleic acid molecule comprising the nucleotide sequence of SEQ ID NO:1 or 3. In another preferred embodiment, a COE-2 protein includes at least one or more of the following four features: a carboxylesterase domain, a transmembrane domain, a carboxylesterase B1 signature motif, a carboxylesterase B2 signature motif, and is at least 273 amino acids in length. In another preferred embodiment, a COE-2 protein includes at least one or more of the following four features: a carboxylesterase domain, a transmembrane domain, a carboxylesterase B1 signature motif, a carboxylesterase B2 signature motif, and has a COE-2 activity.

As used interchangeably herein, a "COE-2 activity", "biological activity of COE-2" or "functional activity of COE-2", includes an activity exerted or mediated by a COE-2 protein, polypeptide or nucleic acid molecule on a COE-2 responsive cell (e.g., a nerve terminus, an immune cell), or on a COE-2 substrate, as determined in vivo or in vitro, according to standard techniques. In one embodiment, a COE-2 activity is a direct activity, such as an association with a COE-2 target molecule. A COE-2 activity can also be an indirect activity, such as a cellular signaling activity mediated by interaction of the COE-2 protein with a COE-2 substrate or ligand. As used herein, a "target molecule" or "binding partner" is a molecule with which a COE-2 protein binds or interacts in nature, such that COE-2-mediated function is achieved. A COE-2 target molecule can be a non-COE-2 molecule or a COE-2 protein or polypeptide of the present invention. In an exemplary embodiment, a COE-2 target molecule is a COE-2 substrate or ligand. Examples of COE-2 substrates include diacyl glycerol compounds, phospholipids, lysophosphatidylcholine, eicosanoid compounds (e.g. arachidonic acid), and cannabinoids (e.g., anandamide, 2-AG).

In a preferred embodiment, a COE-2 activity is at least one of the following activities: (i) interaction with a COE-2 substrate or target molecule; (ii) conversion of a COE-2 substrate or target molecule to a product (e.g., hydrolysis of an ester linkage and/or liberation of the free acid form of the substrate, for example, diacyl glycerol compounds, phospholipids, lysophosphatidylcholine, eicosanoid compounds (e.g. arachidonic acid), and cannabinoids (e.g., anandamide, 2-AG); (iii) interaction with and/or hydrolysis of a non-COE-2 protein; (iv) activation/deactivation of a COE-2 substrate or target molecule (e.g., cannabinoids (e.g., anandamide, 2-AG)); (v) the modulation of a pain response; (vi) the modulation of a fever response; (vii) the modulation of an inflammatory response; (viii) metabolism and/or detoxification of drugs or xenobiotics; (ix) modulation of cellular signaling and/or gene transcription (e.g., either directly or indirectly); and (x) modulation of cellular proliferation and/or differentiation.

The nucleotide sequence of the isolated human COE-2 cDNA and the predicted amino acid sequence encoded by the COE-2 cDNA are shown in SEQ ID NO:1 and 2, respectively.

The human COE-2 gene, which is approximately 1983 nucleotides in length, encodes a protein having a molecular weight of approximately 64.2 kD and which is approximately 584 amino acid residues in length.

Various aspects of the invention are described in further detail in the following subsections:

I. Isolated Nucleic Acid Molecules

One aspect of the invention pertains to isolated nucleic acid molecules that encode COE-2 proteins or biologically active portions thereof, as well as nucleic acid fragments sufficient for use as hybridization probes to identify COE-2-encoding nucleic acid molecules (e.g., COE-2 mRNA) and fragments for use as PCR primers for the amplification or mutation of COE-2 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated COE-2 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1 or 3, or a complement thereof, or a portion thereof, can be isolated using standard molecular biology techniques and the sequence information provided herein. Using all or a portion of the nucleic acid sequence of SEQ ID NO:1 or 3, or a complement thereof, as hybridization probes, COE-2 nucleic acid molecules can be isolated using standard hybridization and cloning techniques (e.g., as described in Sambrook, J., Fritsh, E. F., and Maniatis, T. *Molecular Cloning: A Laboratory Manual.* 2nd, ed., *Cold Spring Harbor Laboratory,* Cold Spring Harbor Laboratory Press, Cold Spring Harbor, N.Y., 1989).

Moreover, a nucleic acid molecule encompassing all or a portion of SEQ ID NO:1 or 3, or a complement thereof can be isolated by the polymerase chain reaction (PCR) using synthetic oligonucleotide primers designed based upon the sequence of SEQ ID NO:1 or 3.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to COE-2 nucleotide sequences can be prepared by standard synthetic techniques, e.g., using an automated DNA synthesizer.

In one embodiment, an isolated nucleic acid molecule of the invention comprises the nucleotide sequence shown in SEQ ID NO:1 or 3, or a complement thereof. This cDNA may comprise sequences encoding the human COE-2 protein (e.g., the "coding region", from nucleotides 98–1852), as well as 5' untranslated sequence (nucleotides 1–97) and 3' untranslated sequences (nucleotides 1853–1983) of SEQ ID NO:1, or a complement thereof. Alternatively, the nucleic acid molecule can comprise only the coding region of SEQ ID NO:1 (e.g., nucleotides 98–1852, corresponding to SEQ ID NO:3), or a complement thereof. Accordingly, in another embodiment, an isolated nucleic acid molecule of the invention comprises SEQ ID NO:3 and nucleotides 1–97 of SEQ ID NO:1 or a complement thereof. In yet another embodiment, the isolated nucleic acid molecule comprises SEQ ID NO:3 and nucleotides 1853–1983 of SEQ ID NO:1, or a complement thereof. In yet another embodiment, the nucleic acid molecule consists of the nucleotide sequence set forth as SEQ ID NO:1 or SEQ ID NO:3, or a complement thereof.

In still another embodiment, an isolated nucleic acid molecule of the invention comprises a nucleic acid molecule which is a complement of the nucleotide sequence shown in SEQ ID NO:1 or 3, or a portion of any of these nucleotide sequences. A nucleic acid molecule which is complementary to the nucleotide sequence shown in SEQ ID NO:1 or 3, is one which is sufficiently complementary to the nucleotide sequence shown in SEQ ID NO:1 or 3, such that it can hybridize to the nucleotide sequence shown in SEQ ID NO:1 or 3, thereby forming a stable duplex.

In still another embodiment, an isolated nucleic acid molecule of the present invention comprises a nucleotide sequence which is at least about 50%, 55%, 60%, 65%, 70%, 75%, 80%, 85%, 90%, 93%, 94%, 95%, 96%, 97%, 98%, 99% or more identical to the nucleotide sequence shown in SEQ ID NO:1 or 3 (e.g., to the entire length of the nucleotide sequence), or a portion or complement of any of these nucleotide sequences. In one embodiment, a nucleic acid molecule of the present invention comprises a nucleotide sequence which is at least (or no greater than) 50, 100, 250, 300, 400, 600, 800, 828, 900, 1000, 1100, 1200, 1300, 1400, 1500, 1600, 1700, 1800, 1900, 1950, or more nucleotides in length and hybridizes under stringent hybridization conditions to a complement of a nucleic acid molecule of SEQ ID NO: 1 or 3.

Moreover, the nucleic acid molecule of the invention can comprise only a portion of the nucleic acid sequence of SEQ ID NO:1 or 3, for example, a fragment which can be used as a probe or primer or a fragment encoding a portion of a COE-2 protein, e.g., a biologically active portion of a COE-2 protein. The nucleotide sequence determined from the cloning of the COE-2 gene allows for the generation of probes and primers designed for use in identifying and/or cloning other COE-2 family members, as well as COE-2 homologues from other species. The probe/primer (e.g., oligonucleotide) typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sequence of SEQ ID NO: 1 or 3, or of a naturally occurring allelic variant or mutant of SEQ ID NO:1 or 3, or to complements of any of the aforementioned.

Exemplary probes or primers are at least (or no greater than) 12 or 15, 20 or 25, 30, 35, 40, 45, 50, 55, 60, 65, 70, 75 or more nucleotides in length and/or comprise consecutive nucleotides of an isolated nucleic acid molecule described herein. Also included within the scope of the present invention are probes or primers comprising contiguous or consecutive nucleotides of an isolated nucleic acid molecule described herein, but for the difference of 1, 2, 3, 4, 5, 6, 7, 8, 9 or 10 bases within the probe or primer sequence. Probes based on the COE-2 nucleotide sequences can be used to detect (e.g., specifically detect) transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. In another embodiment a set of primers is provided, e.g., primers suitable for use in a PCR, which can be used to amplify a selected region of a COE-2 sequence, e.g., a domain, region, site or other sequence described herein. The primers should be at least 5, 10, or 50 base pairs in length and less than 100, or less than 200, base pairs in length. The primers should be identical, or differ by no greater than 1, 2, 3, 4, 5, 6, 7, 8, 9 or 10 bases when compared to a sequence disclosed herein or to the sequence of a naturally occurring variant. Such probes can be used as a part of a diagnostic test kit for identifying cells or tissue which misexpress a COE-2 protein, such as by measuring a level of a COE-2-encoding nucleic acid in a sample of cells from a subject, e.g., detecting COE-2 mRNA levels or determining whether a genomic COE-2 gene has been mutated or deleted.

A nucleic acid fragment encoding a "biologically active portion of a COE-2 protein" can be prepared by isolating a portion of the nucleotide sequence of SEQ ID NO:1 or 3, which encodes a polypeptide having a COE-2 biological activity (the biological activities of the COE-2 proteins are described herein), expressing the encoded portion of the COE-2 protein (e.g., by recombinant expression in vitro) and assessing the activity of the encoded portion of the COE-2 protein. In an exemplary embodiment, the nucleic acid molecule is at least 50–100, 100–250, 250–500, 500–750, 750–1000, 1000–1250, 1250–1500, 1500–1750, 1750–1950 or more nucleotides in length and encodes a protein having a COE-2 activity (as described herein).

The invention further encompasses nucleic acid molecules that differ from the nucleotide sequence shown in SEQ ID NO: 1 or 3, due to degeneracy of the genetic code and thus encode the same COE-2 proteins as those encoded by the nucleotide sequence shown in SEQ ID NO:1 or 3, In another embodiment, an isolated nucleic acid molecule of the invention has a nucleotide sequence encoding a protein having an amino acid sequence which differs by at least 1, but no greater than 5, 10, 20, 50 or 100 amino acid residues from the amino acid sequence shown in SEQ ID NO:2. In yet another embodiment, the nucleic acid molecule encodes the amino acid sequence of human COE-2. If an alignment is needed for this comparison, the sequences should be aligned for maximum homology.

Nucleic acid variants can be naturally occurring, such as allelic variants (same locus), homologues (different locus), and orthologues (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

Allelic variants result, for example, from DNA sequence polymorphisms within a population (e.g., the human population) that lead to changes in the amino acid sequences of the COE-2 proteins. Such genetic polymorphism in the COE-2 genes may exist among individuals within a population due to natural allelic variation. As used herein, the terms "gene" and "recombinant gene" refer to nucleic acid molecules which include an open reading frame encoding a COE-2 protein, preferably a mammalian COE-2 protein, and can further include non-coding regulatory sequences, and introns.

Accordingly, in one embodiment, the invention features isolated nucleic acid molecules which encode a naturally occurring allelic variant of a polypeptide comprising the amino acid sequence of SEQ ID NO:2, wherein the nucleic acid molecule hybridizes to a complement of a nucleic acid molecule comprising SEQ ID NO:1 or 3, for example, under stringent hybridization conditions.

Non-functional allelic variants are naturally occurring amino acid sequence variants of the COE-2 protein, e.g., human COE-2, that do not have the ability to either bind a COE-2 substrate or ligand, hydrolyze a COE-2 substrate, or modulate cellular signaling. Non-functional allelic variants will typically contain a non-conservative substitution, a deletion, or insertion, or premature truncation of the amino acid sequence of SEQ ID NO:2, or a substitution, insertion, or deletion in critical residues or critical regions of the protein.

The present invention further provides non-human orthologues (e.g., non-human orthologues of the human COE-2 protein). Orthologues of the human COE-2 protein are proteins that are isolated from non-human organisms and possess the same COE-2 substrate or ligand binding mechanisms, carboxylesterase activity, and/or modulation of inflammation, pain, and fever mechanisms of the human COE-2 protein. Orthologues of the human COE-2 protein can readily be identified as comprising an amino acid sequence that is substantially homologous to SEQ ID NO:2.

Moreover, nucleic acid molecules encoding other COE-2 family members and, thus, which have a nucleotide sequence which differs from the COE-2 sequences of SEQ ID NO:1 or 3 are intended to be within the scope of the invention. For example, another COE-2 cDNA can be identified based on the nucleotide sequence of human COE-2. Moreover, nucleic acid molecules encoding COE-2 proteins from different species, and which, thus, have a nucleotide sequence which differs from the COE-2 sequences of SEQ ID NO:1 or 3 are intended to be within the scope of the invention. For example, a mouse or monkey COE-2 cDNA can be identified based on the nucleotide sequence of a human COE-2.

Nucleic acid molecules corresponding to natural allelic variants and homologues of the COE-2 cDNAs of the invention can be isolated based on their homology to the COE-2 nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the COE-2 cDNAs of the invention can further be isolated by mapping to the same chromosome or locus as the COE-2 gene.

Orthologues, homologues and allelic variants can be identified using methods known in the art (e.g., by hybridization to an isolated nucleic acid molecule of the present invention, for example, under stringent hybridization conditions). In one embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1 or 3. In other embodiments, the nucleic acid is at least 50, 100, 250, 300, 400, 600, 800, 828, 900, 1000, 1100, 1200, 1300, 1400, 1500, 1600, 1700, 1800, 1900, 1950 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4, and 6. Additional stringent conditions can be found in *Molecular Cloning: A Laboratory Manual*, Sambrook et al., Cold Spring Harbor Press, Cold Spring Harbor, N.Y. (1989), chapters 7, 9, and 11. A preferred, non-limiting example of stringent hybridization conditions includes hybridization in 4× sodium chloride/sodium citrate (SSC), at about 65–70° C. (or alternatively hybridization in 4×SSC plus 50% formamide at about 42–50° C.) followed by one or more washes in 1×SSC, at about 65–70° C. A preferred, non-limiting example of highly stringent hybridization conditions includes hybridization in 1×SSC, at about 65–70° C. (or alternatively hybridization in 1×SSC plus 50% formamide at about 42–50° C.) followed by one or more washes in 0.3×SSC, at about 65–70° C. A preferred, non-limiting example of reduced stringency hybridization conditions includes hybridization in 4×SSC, at about 50–60° C. (or alternatively hybridization in 6×SSC plus 50% formamide at about 40–45° C.) followed by one or more washes in 2×SSC, at about 50–60° C.. Ranges intermediate to the above-recited values, e.g., at 65–70° C. or at 42–50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.1 5M NaCl and 15 mM sodium citrate) in the hybridization and wash buffers; washes are performed for 15 minutes each after hybridization is complete. The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m(°C.)=2(\# \text{ of } A+T \text{ bases})+4(\# \text{ of } G+C \text{ bases})$. For hybrids between 18 and 49 base pairs in length, $T_m(°C.)=81.5+16.6(\log_{10}[Na^+])+0.41(\% G+C)-(600/N)$, where N is the number of bases in the hybrid, and $[Na^+]$ is the concentration of sodium ions in the hybridization buffer ($[Na^+]$ for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5M $NaH_2PO_4$, 7% SDS at about 65° C., followed by one or more washes at 0.02M $NaH_2PO_4$, 1% SDS at 65° C. (see e.g., Church and Gilbert (1984) Proc. Natl. Acad. Sci. USA 81:1991–1995), or alternatively 0.2×SSC, 1% SDS.

Preferably, an isolated nucleic acid molecule of the invention that hybridizes under stringent conditions to the sequence of SEQ ID NO:1 or 3 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the COE-2 sequences that may exist in the population, the skilled artisan will further appreciate that changes can be introduced by mutation into the nucleotide sequences of SEQ ID NO:1 or 3, thereby leading to changes in the amino acid sequence of the encoded COE-2 proteins, without altering the functional ability of the COE-2 proteins. For example, nucleotide substitutions leading to amino acid substitutions at "non-essential" amino acid residues can be made in the sequence of SEQ ID NO:1 or 3. A "non-essential" amino acid residue is a residue that can be altered from the wild-type sequence of COE-2 (e.g., the sequence of SEQ ID NO:2) without altering the biological activity, whereas an "essential" amino acid residue is required for biological activity. For example, amino acid residues that are conserved among the COE-2 proteins of the present invention, e.g., those present in carboxylesterase domain, are predicted to be particularly unamenable to alteration. Furthermore, additional amino acid residues that are conserved between the COE-2 proteins of the present invention and other members of the carboxylesterase family are not likely to be amenable to alteration.

Accordingly, another aspect of the invention pertains to nucleic acid molecules encoding COE-2 proteins that contain changes in amino acid residues that are not essential for activity. Such COE-2 proteins differ in amino acid sequence from SEQ ID NO:2, yet retain biological activity. In one embodiment, the isolated nucleic acid molecule comprises a nucleotide sequence encoding a protein, wherein the protein comprises an amino acid sequence at least about 50%, 55%, 60%, 65%, 70%, 75%, 80%, 85%, 90%, 95%, 96%, 97%, 98% 99% or more identical to SEQ ID NO:2, e.g., to the entire length of SEQ ID NO:2.

An isolated nucleic acid molecule encoding a COE-2 protein homologous to the protein of SEQ ID NO:2 can be created by introducing one or more nucleotide substitutions, additions or deletions into the nucleotide sequence of SEQ ID NO:1 or 3, such that one or more amino acid substitutions, additions or deletions are introduced into the encoded protein. Mutations can be introduced into SEQ ID NO:1 or 3 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a COE-2 protein is preferably replaced with another amino acid residue from the same side chain family. Alternatively, in another embodiment, mutations can be introduced randomly along all or part of a COE-2 coding sequence, such as by saturation mutagenesis, and the resultant mutants can be screened for COE-2 biological activity to identify mutants that retain activity. Following mutagenesis of SEQ ID NO:1 or 3, the encoded protein can be expressed recombinantly and the activity of the protein can be determined.

In a preferred embodiment, a mutant COE-2 protein can be assayed for the ability to (i) interact with a COE-2 substrate or target molecule; (ii) convert one or more COE-2 substrates or target molecules into a product (e.g., hydrolysis of an ester linkage and/or liberation of the free acid form of the substrate, for example diacyl glycerol compounds, phospholipids, lysophosphatidylcholine, eicosanoid compounds (e.g. arachidonic acid), and cannabinoids (e.g., anandamide, 2-AG); (iii) interact with and/or hydrolyze a non-COE-2 protein; (iv) activate/deactivate a COE-2 substrate or target molecule (e.g., cannabinoids (e.g., anandamide, 2-AG); (v) modulate an inflammatory response; (vi) modulate a fever response; (vii) modulate a pain response; (viii) metabolize and/or detoxify drugs or xenobiotics; (ix) modulate cellular signaling and/or gene transcription (e.g., either directly or indirectly); and (x) modulate cellular proliferation and/or differentiation.

In addition to the nucleic acid molecules encoding COE-2 proteins described above, another aspect of the invention pertains to isolated nucleic acid molecules which are antisense thereto. In an exemplary embodiment, the invention provides an isolated nucleic acid molecule which is antisense to a COE-2 nucleic acid molecule (e.g., is antisense to the coding strand of a COE-2 nucleic acid molecule). An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire COE-2 coding strand, or to only a portion thereof. In one embodiment, an antisense nucleic acid molecule is antisense to "coding region sequences" of the coding strand of a nucleotide sequence encoding COE-2. The term "coding region sequences" refers to the region of the nucleotide sequence comprising codons which are translated into amino acid residues (e.g., the coding region sequences of human COE-2 corresponding to SEQ ID NO:3). In another embodiment, the antisense nucleic acid molecule is antisense to a "noncoding region" of the coding strand of a nucleotide sequence encoding COE-2. The term "noncoding region" refers to 5' and/or 3' sequences which flank the coding region sequences that are not translated into amino acids (also referred to as 5' and 3' untranslated regions).

Given the coding strand sequences encoding COE-2 disclosed herein (e.g., SEQ ID NO:3), antisense nucleic acids of the invention can be designed according to the rules of Watson and Crick base pairing. The antisense nucleic acid molecule can be complementary to coding region sequences of COE-2 mRNA, but more preferably is an oligonucleotide which is antisense to only a portion of the COE-2 mRNA. An antisense oligonucleotide can be, for example, about 5, 10, 15, 20, 25, 30, 35, 40, 45, 50, 55, 60, 65, 70, 75, 80, or more nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a COE-2 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–59 1)) can be used to catalytically cleave COE-2 mRNA transcripts to thereby inhibit translation of COE-2 mRNA. A ribozyme having specificity for a COE-2-encoding nucleic acid can be designed based upon the nucleotide sequence of a COE-2 cDNA disclosed herein (i.e., SEQ ID NO:1 or 3. For example, a derivative of a Tetrahymena L-19 IVS RNA can be constructed in which the nucleotide sequence of the active site is complementary to the nucleotide sequence to be cleaved in a COE-2-encoding mRNA. See, e.g., Cech et al. U.S. Patent No. 4,987,071; and Cech et al. U.S. Pat. No. 5,116,742. Alternatively, COE-2 mRNA can be used to select a catalytic RNA having a specific ribonuclease activity from a pool of RNA molecules. See, e.g., Bartel, D. and Szostak, J. W. (1993) Science 261:1411–1418.

Alternatively, COE-2 gene expression can be inhibited by targeting nucleotide sequences complementary to the regulatory region of the COE-2 (e.g., the COE-2 promoter and/or enhancers; e.g., nucleotides 1–221 of SEQ ID NO:1) to form triple helical structures that prevent transcription of the COE-2 gene in target cells. See generally, Helene, C. (1991) *Anticancer Drug Des.* 6(6):569–84; Helene, C. et al. (1992) *Ann. N.Y Acad. Sci.* 660:27–36; and Maher, L. J. (1992) *Bioassays* 14(12):807–15.

In yet another embodiment, the COE-2 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup, B. et al. (1996) *Bioorganic & Medicinal Chemistry* 4(1):5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup, B. et al. (1996) supra; Perry-O'Keefe et al. (1996) *Proc. Natl. Acad. Sci. USA* 93:14670–675.

PNAs of COE-2 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of COE-2 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup, B. et al. (1996) supra)); or as probes or primers for DNA sequencing or hybridization (Hyrup, B. et al. (1996) supra; Perry-O'Keefe (1996) supra).

In another embodiment, PNAs of COE-2 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of COE-2 nucleic acid molecules can be generated which may combine the advantageous properties of PNA and DNA. Such chimeras allow DNA recognition enzymes (e.g., RNase H and DNA polymerases) to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, B. et al (1996) supra). The synthesis of PNA-DNA chimeras can be performed as described in Hyrup, B. et al. (1996) supra and Finn, P. J. et al. (1996) *Nucleic Acids Res.* 24 (17):3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17:5973–88). PNA monomers are then coupled in a stepwise manner to produce a chimeric molecule with a 5' PNA segment and a 3' DNA segment (Finn, P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad Sci. USA* 84:648–652; PCT Publication No. W088/09810) or the blood-brain barrier (see, e.g., PCT Publication No. W089/10134). In addition, oligonucleotides can be modified with hybridization-triggered cleavage agents (See, e.g., Krol et al. (1988) *Bio-Techniques* 6:958–976) or intercalating agents (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

II. Isolated COE-2 Proteins and Anti-COE-2 Antibodies

One aspect of the invention pertains to isolated or recombinant COE-2 proteins and polypeptides, and biologically active portions thereof, as well as polypeptide fragments suitable for use as immunogens to raise anti-COE-2 antibodies. In one embodiment, native COE-2 proteins can be isolated from cells or tissue sources by an appropriate purification scheme using standard protein purification techniques. In another embodiment, COE-2 proteins are produced by recombinant DNA techniques. Alternative to recombinant expression, a COE-2 protein or polypeptide can be synthesized chemically using standard peptide synthesis techniques.

An "isolated" or "purified" protein or biologically active portion thereof is substantially free of cellular material or other contaminating proteins from the cell or tissue source from which the COE-2 protein is derived, or substantially free from chemical precursors or other chemicals when chemically synthesized. The language "substantially free of cellular material" includes preparations of COE-2 protein in which the protein is separated from cellular components of the cells from which it is isolated or recombinantly produced. In one embodiment, the language "substantially free of cellular material" includes preparations of COE-2 protein having less than about 30% (by dry weight) of non-COE-2 protein (also referred to herein as a "contaminating protein"), more preferably less than about 20% of non-COE-2 protein, still more preferably less than about 10% of non-COE-2 protein, and most preferably less than about 5% non-COE-2 protein. When the COE-2 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of COE-2 protein in which the protein is separated from chemical precursors or other chemicals which are involved in the synthesis of the protein. In one embodiment, the language "substantially free of chemical precursors or other chemicals" includes preparations of COE-2 protein having less than about 30% (by dry weight) of chemical precursors or non-COE-2 chemicals, more preferably less than about 20% chemical precursors or non-COE-2 chemicals, still more preferably less than about 10% chemical precursors or non-COE-2 chemicals, and most preferably less than about 5% chemical precursors or non-COE-2 chemicals.

As used herein, a "biologically active portion" of a COE-2 protein includes a fragment of a COE-2 protein which participates in an interaction between a COE-2 molecule and a non-COE-2 molecule (e.g., a COE-2 substrate). Biologically active portions of a COE-2 protein include peptides comprising amino acid sequences sufficiently homologous to or derived from the COE-2 amino acid sequences, e.g., the amino acid sequences shown in SEQ ID NO:2, which include sufficient amino acid residues to exhibit at least one activity of a COE-2 protein. Typically, biologically active portions comprise a domain or motif with at least one activity of the COE-2 protein, e.g., carboxylesterase activity, modulating intra- or inter-cellular signaling, modulating gene expression, and/or modulating cell growth and differentiation mechanisms. A biologically active portion of a COE-2 protein can be a polypeptide which is, for example, 10, 25, 50, 75, 100, 125, 150, 175, 200, 250, 300, 350, 400, 450, 500 or more amino acids in length. Biologically active portions of a COE-2 protein can be used as targets for developing agents which modulate a COE-2 mediated activity, e.g., intra- or inter-cellular signaling, cellular gene expression, or a cell growth or differentiation mechanism.

In one embodiment, a biologically active portion of a COE-2 protein comprises at least one carboxylesterase domain. Moreover, other biologically active portions, in which other regions of the protein are deleted, can be prepared by recombinant techniques and evaluated for one or more of the functional activities of a native COE-2 protein.

Another aspect of the invention features fragments of the protein having the amino acid sequence of SEQ ID NO:2, for example, for use as immunogens. In one embodiment, a fragment comprises at least 5 amino acids (e.g., contiguous or consecutive amino acids) of the amino acid sequence of SEQ ID NO:2. In another embodiment, a fragment comprises at least 10, 15, 20, 25, 30, 35, 40, 45, 50 or more amino acids (e.g., contiguous or consecutive amino acids) of the amino acid sequence of SEQ ID NO:2.

In a preferred embodiment, a COE-2 protein has an amino acid sequence shown in SEQ ID NO:2. In other embodiments, the COE-2 protein is substantially identical to SEQ ID NO:2, and retains the functional activity of the protein of SEQ ID NO:2, yet differs in amino acid sequence due to natural allelic variation or mutagenesis, as described in detail in subsection I above. In another embodiment, the COE-2 protein is a protein which comprises an amino acid sequence at least about 50%, 55%, 60%, 65%, 70%, 75%, 80%, 85%, 90%, 95%, 96%, 97%, 98%, 99% or more identical to SEQ ID NO:2.

In another embodiment, the invention features a COE-2 protein which is encoded by a nucleic acid molecule consisting of a nucleotide sequence at least about 50%, 55%, 60%, 63%, 65%, 70%, 75%, 80%, 85%, 90%, 93%, 94%, 95%, 96%, 97%, 98%, 99% or more identical to a nucleotide sequence of SEQ ID NO:1 or 3, or a complement thereof. This invention further features a COE-2 protein which is encoded by a nucleic acid molecule consisting of a nucleotide sequence which hybridizes under stringent hybridization conditions to a complement of a nucleic acid molecule comprising the nucleotide sequence of SEQ ID NO:1 or 3, or a complement thereof.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the COE-2 amino acid sequence of SEQ ID NO:2 having 584 amino acid residues, at least 175, preferably at least 233, more preferably at least 292, even more preferably at least 350, and even more preferably at least 408, 467 or 525 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available online through the Genetics Computer Group), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online through the Genetics Computer Group), using a NWSgapdna.CMP matrix and a gap weight of 40, 50, 60, 70, or 80 and a length weight of 1, 2, 3, 4, 5, or 6. A preferred, non-limiting example of parameters to be used in conjunction with the GAP program include a Blosum 62 scoring matrix with a gap penalty of 12, a gap extend penalty of 4, and a frameshift gap penalty of 5.

In another embodiment, the percent identity between two amino acid or nucleotide sequences is determined using the algorithm of Meyers and Miller (*Comput. Appl. Biosci.,* 4:11–17 (1988)) which has been incorporated into the ALIGN program (version 2.0 or version 2.0U), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403–10. BLAST nucleotide searches can be performed with the NBLAST program, score=100, wordlength=12 to obtain nucleotide sequences homologous to COE-2 nucleic acid molecules of the invention. BLAST protein searches can be performed with the XBLAST program, score=50, wordlength=3 to obtain amino acid sequences homologous to COE-2 protein molecules of the invention. To obtain gapped alignments for comparison purposes, Gapped BLAST can be utilized as described in Altschul et al. (1997) *Nucleic Acids Res.* 25(17):3389–3402. When utilizing BLAST and Gapped BLAST programs, the default parameters of the respective programs (e.g., XBLAST and NBLAST) can be used. See the National Center for Biotechnology Information website.

The invention also provides COE-2 chimeric or fusion proteins. As used herein, a COE-2 "chimeric protein" or "fusion protein" comprises a COE-2 polypeptide operatively linked to a non-COE-2 polypeptide. A "COE-2 polypeptide" refers to a polypeptide having an amino acid sequence corresponding to COE-2, whereas a "non-COE-2 polypeptide" refers to a polypeptide having an amino acid sequence corresponding to a protein which is not substantially homologous to the COE-2 protein, e.g., a protein which is different from the COE-2 protein and which is derived from the same or a different organism. Within a COE-2 fusion protein the COE-2 polypeptide can correspond to all or a portion of a COE-2 protein. In a preferred embodiment, a COE-2 fusion protein comprises at least one biologically active portion of a COE-2 protein. In another preferred embodiment, a COE-2 fusion protein comprises at least two biologically active portions of a COE-2 protein. Within the fusion protein, the term "operatively linked" is intended to indicate that the COE-2 polypeptide and the non-COE-2 polypeptide are fused in-frame to each other. The non-COE-2 polypeptide can be fused to the N-terminus or C-terminus of the COE-2 polypeptide.

For example, in one embodiment, the fusion protein is a GST-COE-2 fusion protein in which the COE-2 sequences are fused to the C-terminus of the GST sequences. Such fusion proteins can facilitate the purification of recombinant COE-2. In another embodiment, the fusion protein is a COE-2 protein containing a heterologous signal sequence at its N-terminus. In certain host cells (e.g., mammalian host cells), expression and/or secretion of COE-2 can be increased through use of a heterologous signal sequence.

The COE-2 fusion proteins of the invention can be incorporated into pharmaceutical compositions and administered to a subject in vivo. The COE-2 fusion proteins can be used to affect the bioavailability of a COE-2 substrate. Use of COE-2 fusion proteins may be useful therapeutically for the treatment of disorders caused by, for example, (i) aberrant modification or mutation of a gene encoding a COE-2 protein; (ii) mis-regulation of the COE-2 gene; and (iii) aberrant post-translational modification of a COE-2 protein.

Moreover, the COE-2-fusion proteins of the invention can be used as immunogens to produce anti-COE-2 antibodies in a subject, to purify COE-2 ligands, and in screening assays to identify molecules which inhibit the interaction of COE-2 with a COE-2 substrate.

Preferably, a COE-2 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A COE-2-encoding nucleic acid can be cloned into such an expression vector such that the fusion moiety is linked in-frame to the COE-2 protein.

The present invention also pertains to variants of the COE-2 proteins which function as either COE-2 agonists (mimetics) or as COE-2 antagonists. Variants of the COE-2 proteins can be generated by mutagenesis, e.g., discrete point mutation or truncation of a COE-2 protein. An agonist of the COE-2 proteins can retain substantially the same, or a subset, of the biological activities of the naturally occurring form of a COE-2 protein. An antagonist of a COE-2 protein can inhibit one or more of the activities of the naturally occurring form of the COE-2 protein by, for example, competitively modulating a COE-2-mediated activity of a COE-2 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the COE-2 protein.

In one embodiment, variants of a COE-2 protein which function as either COE-2 agonists (mimetics) or as COE-2 antagonists can be identified by screening combinatorial libraries of mutants, e.g., truncation mutants, of a COE-2 protein for COE-2 protein agonist or antagonist activity. In one embodiment, a variegated library of COE-2 variants is generated by combinatorial mutagenesis at the nucleic acid level and is encoded by a variegated gene library. A variegated library of COE-2 variants can be produced by, for example, enzymatically ligating a mixture of synthetic oligonucleotides into gene sequences such that a degenerate set of potential COE-2 sequences is expressible as individual polypeptides, or alternatively, as a set of larger fusion proteins (e.g., for phage display) containing the set of COE-2 sequences therein. There are a variety of methods which can be used to produce libraries of potential COE-2 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential COE-2 sequences. Methods for synthesizing degenerate oligonucleotides are known in the art (see, e.g., Narang, S. A. (1983) *Tetrahedron* 39:3; Itakura et al (1984) *Annu. Rev. Biochem.* 53:323; Itakura et al. (1984) *Science* 198:1056; Ike et al. (1983) *Nucleic Acid Res.* 11:477.

In addition, libraries of fragments of a COE-2 protein coding sequence can be used to generate a variegated population of COE-2 fragments for screening and subsequent selection of variants of a COE-2 protein. In one embodiment, a library of coding sequence fragments can be generated by treating a double stranded PCR fragment of a COE-2 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the COE-2 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of COE-2 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify COE-2 variants (Arkin and Yourvan (1992) *Proc. Natl. Acad. Sci. USA* 89:7811–7815; Delgrave et al. (1993) *Protein Engineering* 6(3):327–331).

In one embodiment, cell based assays can be exploited to analyze a variegated COE-2 library. For example, a library of expression vectors can be transfected into a cell line, e.g., a liver cell line, which ordinarily responds to COE-2 in a particular COE-2 substrate-dependent manner. The transfected cells are then contacted with COE-2 and the effect of the expression of the mutant on signaling by the COE-2 substrate can be detected, e.g., by measuring levels of hydrolyzed substrate, gene transcription, and/or cell growth and differentiation. Plasmid DNA can then be recovered from the cells which score for inhibition, or alternatively, potentiation of signaling by the COE-2 substrate, and the individual clones further characterized.

An isolated COE-2 protein, or a portion or fragment thereof, can be used as an immunogen to generate antibodies that bind COE-2 using standard techniques for polyclonal and monoclonal antibody preparation. A full-length COE-2 protein can be used or, alternatively, the invention provides antigenic peptide fragments of COE-2 for use as immunogens. The antigenic peptide of COE-2 comprises at least 8 amino acid residues of the amino acid sequence shown in SEQ ID NO:2 and encompasses an epitope of COE-2 such that an antibody raised against the peptide forms a specific immune complex with COE-2. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of COE-2 that are located on the surface of the protein, e.g., hydrophilic regions, as well as regions with high antigenicity (see, for example, FIG. 1).

A COE-2 immunogen typically is used to prepare antibodies by immunizing a suitable subject (e.g., rabbit, goat, mouse, or other mammal) with the immunogen. An appropriate immunogenic preparation can contain, for example, recombinantly expressed COE-2 protein or a chemically-synthesized COE-2 polypeptide. The preparation can further include an adjuvant, such as Freund's complete or incomplete adjuvant, or similar immunostimulatory agent. Immunization of a suitable subject with an immunogenic COE-2 preparation induces a polyclonal anti-COE-2 antibody response.

Accordingly, another aspect of the invention pertains to anti-COE-2 antibodies. The term "antibody" as used herein refers to immunoglobulin molecules and immunologically active portions of immunoglobulin molecules, i.e., molecules that contain an antigen binding site which specifically binds (immunoreacts with) an antigen, such as COE-2. Examples of immunologically active portions of immunoglobulin molecules include F(ab) and $F(ab')_2$ fragments which can be generated by treating the antibody with an enzyme such as pepsin. The invention provides polyclonal and monoclonal antibodies that bind COE-2. The term "monoclonal antibody" or "monoclonal antibody composition", as used herein, refers to a population of antibody molecules that contain only one species of an antigen binding site capable of immunoreacting with a particular epitope of COE-2. A monoclonal antibody composition thus typically displays a single binding affinity for a particular COE-2 protein with which it immunoreacts.

Polyclonal anti-COE-2 antibodies can be prepared as described above by immunizing a suitable subject with a COE-2 immunogen. The anti-COE-2 antibody titer in the immunized subject can be monitored over time by standard techniques, such as with an enzyme linked immunosorbent assay (ELISA) using immobilized COE-2. If desired, the antibody molecules directed against COE-2 can be isolated from the mammal (e.g., from the blood) and further purified by well known techniques, such as protein A chromatography to obtain the IgG fraction. At an appropriate time after immunization, e.g., when the anti-COE-2 antibody titers are highest, antibody-producing cells can be obtained from the subject and used to prepare monoclonal antibodies by standard techniques, such as the hybridoma technique originally described by Kohler and Milstein (1975) *Nature* 256:495–497 (see also Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Leener, E. A. (1981) *Yale J. Biol. Med.,* 54:387–402; Gefter, M. L. et al. (1977) *Somatic Cell Genet.* 3:231–36). Briefly, an immortal cell line (typically a myeloma) is fused to lymphocytes (typically splenocytes) from a mammal immunized with a COE-2 immunogen as described above, and the culture supernatants of the resulting hybridoma cells are screened to identify a hybridoma producing a monoclonal antibody that binds COE-2.

Any of the many well known protocols used for fusing lymphocytes and immortalized cell lines can be applied for the purpose of generating an anti-COE-2 monoclonal antibody (see, e.g., Galfre, G. et al. (1977) *Nature* 266:55052; Gefter et al. *Somatic Cell Genet*., supra; Lerner (1981) supra; Kenneth, *Monoclonal Antibodies*, supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind COE-2, e.g., using a standard ELISA assay.

Alternative to preparing monoclonal antibody-secreting hybridomas, a monoclonal anti-COE-2 antibody can be identified and isolated by screening a recombinant combinatorial immunoglobulin library (e.g., an antibody phage display library) with COE-2 to thereby isolate immunoglobulin library members that bind COE-2. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. (1990) *Nature* 348:552–554.

Additionally, recombinant anti-COE-2 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225, 539; Jones et al. (1986) *Nature* 321:552–525; Verhoeyan et al. (1988) *Science* 239:1534; and Beidler et al. (1988) *J. Immunol.* 141:4053–4060.

An anti-COE-2 antibody (e.g., monoclonal antibody) can be used to isolate COE-2 by standard techniques, such as affinity chromatography or immunoprecipitation. An anti-COE-2 antibody can facilitate the purification of natural COE-2 from cells and of recombinantly produced COE-2 expressed in host cells. Moreover, an anti-COE-2 antibody can be used to detect COE-2 protein (e.g., in a cellular lysate or cell supernatant) in order to evaluate the abundance and pattern of expression of the COE-2 protein. Anti-COE-2 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^3H$.

III. Recombinant Expression Vectors and Host Cells

Another aspect of the invention pertains to vectors, for example recombinant expression vectors, containing a COE-2 nucleic acid molecule or vectors containing a nucleic acid molecule which encodes a COE-2 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) *Methods Enzymol.* 185:3–7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., COE-2 proteins, mutant forms of COE-2 proteins, fusion proteins, and the like).

Accordingly, an exemplary embodiment provides a method for producing a protein, preferably a COE-2 protein, by culturing in a suitable medium a host cell of the invention (e.g., a mammalian host cell such as a non-human mammalian cell) containing a recombinant expression vector, such that the protein is produced.

The recombinant expression vectors of the invention can be designed for expression of COE-2 proteins in prokaryotic or eukaryotic cells. For example, COE-2 proteins can be expressed in bacterial cells such as *E. coli*, insect cells (using baculovirus expression vectors) yeast cells or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in COE-2 activity assays, (e.g., direct assays or competitive assays described in detail below), or to generate antibodies specific for COE-2 proteins, for example. In a preferred embodiment, a COE-2 fusion protein expressed in a retroviral expression vector of the present invention can be utilized to infect bone marrow cells, which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al. (1990) *Methods Enzymol.* 185:60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S. (1990) *Methods Enzymol.* 185:119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

In another embodiment, the COE-2 expression vector is a yeast expression vector. Examples of vectors for expression in yeast *S. cerivisae* include pYepSec1 (Baldari, et al. (1987) *Embo J.* 6:229–234), pMFa (Kurjan and Herskowitz (1982) *Cell* 30:933–943), pJRY88 (Schultz et al. (1987) *Gene* 54:113–123), pYES2 (Invitrogen Corporation, San Diego, Calif.), and picZ (InVitrogen Corp., San Diego, Calif.).

Alternatively, COE-2 proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al. *Molecular Cloning: A Laboratory Manual. 2nd, ed, Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuronspecific promoters (e.g., the neurofilament promoter; Byrne and Ruddle (1989) *Proc. Natl. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to COE-2 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., "Antisense RNA as a molecular tool for genetic analysis", *Reviews—Trends in Genetics*, Vol. 1(1) 1986.

Another aspect of the invention pertains to host cells into which a COE-2 nucleic acid molecule of the invention is introduced, e.g., a COE-2 nucleic acid molecule within a vector (e.g., a recombinant expression vector) or a COE-2 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a COE-2 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a COE-2 protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a COE-2 protein. Accordingly, the invention further provides methods for producing a COE-2 protein using the host cells of the invention. In one embodiment, the method comprises culturing the host cell of the invention (into which a recombinant expression vector encoding a COE-2 protein has been introduced) in a suitable medium such that a COE-2 protein is produced. In another embodiment, the method further comprises isolating a COE-2 protein from the medium or the host cell.

The host cells of the invention can also be used to produce non-human transgenic animals. For example, in one embodiment, a host cell of the invention is a fertilized oocyte or an embryonic stem cell into which COE-2-coding sequences have been introduced. Such host cells can then be used to create non-human transgenic animals in which exogenous COE-2 sequences have been introduced into their genome or homologous recombinant animals in which endogenous COE-2 sequences have been altered. Such animals are useful for studying the function and/or activity of a COE-2 protein and for identifying and/or evaluating modulators of COE-2 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous COE-2 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a COE-2-encoding nucleic acid into the male pronuclei of a fertilized oocyte, e.g., by microinjection or retroviral infection, and allowing the oocyte to develop in a pseudopregnant female foster animal. The COE-2 cDNA sequence of SEQ ID NO:1 can be introduced as a transgene into the genome of a non-human animal. Alternatively, a non-human homologue of a human COE-2 gene, such as a rat or mouse COE-2 gene, can be used as a transgene. Alternatively, a COE-2 gene homologue, such as another COE-2 family member, can be isolated based on hybridization to the COE-2 cDNA sequences of SEQ ID NO: 1 or 3 (described further in subsection I above) and used as a transgene. Intronic sequences and polyadenylation signals can also be included in the transgene to increase the efficiency of expression of the transgene. A tissue-specific regulatory sequence(s) can be operably linked to a COE-2 transgene to direct expression of a COE-2 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a COE-2 transgene in its genome and/or expression of COE-2 mRNA in tissues or cells of the animals. A transgenic founder animal can then be used to breed additional animals carrying the transgene. Moreover, transgenic animals carrying a transgene encoding a COE-2 protein can further be bred to other transgenic animals carrying other transgenes.

To create a homologous recombinant animal, a vector is prepared which contains at least a portion of a COE-2 gene into which a deletion, addition or substitution has been introduced to thereby alter, e.g., functionally disrupt, the COE-2 gene. The COE-2 gene can be a human gene (e.g., the cDNA of SEQ ID NO:3), but more preferably, is a non-human homologue of a human COE-2 gene (e.g., a cDNA isolated by stringent hybridization with the nucleotide sequence of SEQ ID NO:1), For example, a mouse COE-2 gene can be used to construct a homologous recombination nucleic acid molecule, e.g., a vector, suitable for altering an endogenous COE-2 gene in the mouse genome. In a preferred embodiment, the homologous recombination nucleic acid molecule is designed such that, upon homologous recombination, the endogenous COE-2 gene is functionally disrupted (i.e., no longer encodes a functional protein; also referred to as a "knock out" vector). Alternatively, the homologous recombination nucleic acid molecule can be designed such that, upon homologous recombination, the endogenous COE-2 gene is mutated or otherwise altered but still encodes functional protein (e.g., the upstream regulatory region can be altered to thereby alter the expression of the endogenous COE-2 protein). In the homologous recombination nucleic acid molecule, the altered portion of the COE-2 gene is flanked at its 5' and 3' ends by additional nucleic acid sequence of the COE-2 gene to allow for homologous recombination to occur between the exogenous COE-2 gene carried by the homologous recombination nucleic acid molecule and an endogenous COE-2 gene in a cell, e.g., an embryonic stem cell. The additional flanking COE-2 nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g. an embryonic stem cell line (e.g., by electroporation) and cells in which the introduced COE-2 gene has homologously recombined with the endogenous COE-2 gene are selected (see e.g., Li, E. et al. (1992) *Cell* 69:915). The selected cells can then be injected into a blastocyst of an animal (e.g., a mouse) to form aggregation chimeras (see e.g., Bradley, A. in *Teratocarcinomas and Embryonic Stem Cells: A Practical Approach*, Robertson, E. J. ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The COE-2 nucleic acid molecules, of COE-2 proteins, fragments thereof, anti-COE-2 antibodies, and COE-2 modulators (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a COE-2 protein or an anti-COE-2 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a COE-2 protein of the invention has one or more of the following activities: (i) interaction with a COE-2 substrate or target molecule (e.g., diacyl glycerol compounds, phospholipids, lysophosphatidylcholine, eicosanoid compounds (e.g. arachidonic acid), and cannabinoids (e.g., anandamide, 2-AG); (ii) conversion of a COE-2 substrate or target molecule to a product (e.g., hydrolysis of an ester linkage and/or liberation of the free acid form of the substrate, for example diacyl glycerol compounds, phospholipids, lysophosphatidylcholine, eicosanoid compounds (e.g. arachidonic acid), and cannabinoids (e.g., anandamide, 2-AG); (iii) interaction with and/or hydrolysis of a non-COE-2 protein; (iv) activation/deactivation of a COE-2 substrate or target molecule (e.g., cannabinoids (e.g., anandamide, 2-AG)); (v) the modulation of inflammatory response; (vi) the modulation of the fever response; (vii) the modulation of the pain response; (viii) metabolism and/or detoxification of drugs or xenobiotics; (ix) modulation of cellular signaling and/or gene transcription (e.g., either directly or indirectly); and (x) modulation of cellular proliferation and/or differentiation.

The isolated nucleic acid molecules of the invention can be used, for example, to express COE-2 protein (e.g., via a recombinant expression vector in a host cell in gene therapy applications), to detect COE-2 mRNA (e.g., in a biological sample) or a genetic alteration in a COE-2 gene, and to modulate COE-2 activity, as described further below. The COE-2 proteins can be used to treat disorders characterized by insufficient or excessive production of a COE-2 substrate or production of COE-2 inhibitors. In addition, the COE-2 proteins can be used to screen for naturally occurring COE-2 substrates, to screen for drugs or compounds which modulate COE-2 activity, as well as to treat disorders characterized by insufficient or excessive production of COE-2 protein or production of COE-2 protein forms which have decreased, aberrant or unwanted activity compared to COE-2 wild type protein (e.g., a COE-2-associated disorder).

In addition to the properties and disorders set forth above, carboxylesterase-associated disorders can also detrimentally affect cellular functions such as lipid metabolism and, hence, many of the signaling processes which depend upon lipid-derived metabolites such as arachidonic acid and related eicosanoids, diacyl glycerol, lysophosphatidic acid, lysophosphatidylcholine, and endocannabinoids, e.g., anandamide and 2-AG. In addition, carboxylesterase-associated disorders include the exaggerated pain response elicited during various forms of tissue injury, e.g., inflammation, infection, and ischemia (usually referred to as hyperalgesia). Moreover, carboxylesterase-associated disorders include musculoskeletal disorders, e.g., joint pain; tooth pain; headaches; or pain associated with surgery, rheumatoid arthritis, viral infection, allergic reaction, asthma, chronic pain, chronic pancreatitis, somatoform disorders, fibromyalgia syndrome, and the like. Other carboxylesterase-associated disorders include those which stem from, or present themselves through aberrant levels of lysophatidic acid (LPA) and related metabolites. Examples of such carboxylesterase-associated disorders include a variety of tumors and cancers, as well as apoptosis, cytoskeletal abberancies, and the like. Further examples of carboxylesterase-associated disorders include those which can be attributed to aberrant levels of a particular lipid metabolite, such as the eicosanoids and prostaglandins. Such disorders include aberrant blood pressure, aberrant blood clotting, misregulation of various reproductive functions, e.g., induction of labor, skin psoriasis, and misregulation of the sleep/wake cycle. Still further examples of carboxylesterase-associated disorders include those which are related to aberrant expression of endocannabinoids, such as anandamide and 2-AG. Such disorders include those relating to pain, vasodialation, and hypotension, as well as those which are behavioral, e.g., alcohol dependence (see, e.g., Hungund and Basavarajappa, (2000) *Alcohol and Alchoholism* 35:126–133) or those in which detrimental effect(s) are the result of separate disorders or injuries, e.g., multiple sclerosis or spinal cord injury.

Moreover, the anti-COE-2 antibodies of the invention can be used to detect and isolate COE-2 proteins, regulate the bioavailability of COE-2 proteins, and modulate COE-2 activity.

A. Screening Assays:

The invention provides a method (also referred to herein as a "screening assay") for identifying modulators, i.e., candidate or test compounds or agents (e.g., peptides, peptidomimetics, small molecules or other drugs) which bind to COE-2 proteins, have a stimulatory or inhibitory effect on, for example, COE-2 expression or COE-2 activity, or have a stimulatory or inhibitory effect on, for example, the expression or activity of a COE-2 substrate.

In one embodiment, the invention provides assays for screening candidate or test compounds which are substrates of a COE-2 protein or polypeptide or biologically active portion thereof. In another embodiment, the invention provides assays for screening candidate or test compounds which bind to or modulate the activity of a COE-2 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:45).

Examples of methods for the synthesis of molecular libraries can be found in the art, for example, in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad Sci. USA* 87:6378–6382); (Felici (1991) *J. Mol. Biol.* 222:301–310); (Ladner supra.).

In one embodiment, an assay is a cell-based assay in which a cell which expresses a COE-2 protein or biologically active portion thereof is contacted with a test compound and the ability of the test compound to modulate COE-2 activity is determined. Determining the ability of the test compound to modulate COE-2 activity can be accomplished by monitoring, for example, COE-2 interaction with a substrate or target molecule, hydrolysis of a substrate and/or conversion of a substrate to a product, activation and/or deactivation of a substrate or target molecule, metabolism and/or detoxification of drugs, modulation of cellular signaling and/or gene transcription, modulation of pain and/or inflammation, and/or modulation of cellular proliferation and/or differentiation. The cell, for example, can be of a mammalian origin.

The ability of the test compound to modulate COE-2 binding to a substrate or to bind to COE-2 can also be determined. Determining the ability of the test compound to modulate COE-2 binding to a substrate can be accomplished, for example, by coupling the COE-2 substrate with a radioisotope or enzymatic label such that binding of the COE-2 substrate to COE-2 can be determined by detecting the labeled COE-2 substrate in a complex. Alternatively, COE-2 could be coupled with a radioisotope or enzymatic label to monitor the ability of a test compound to modulate COE-2 binding to a COE-2 substrate in a complex. Determining the ability of the test compound to bind COE-2 can be accomplished, for example, by coupling the compound with a radioisotope or enzymatic label such that binding of the compound to COE-2 can be determined by detecting the labeled COE-2 compound in a complex. For example, compounds (e.g., COE-2 substrates, for example, diacyl glycerol compounds, phospholipids, lysophosphatidylcholine, eicosanoid compounds (e.g. arachidonic acid), and cannabinoids (e.g., anandamide, 2-AG)) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., a COE-2 substrate such as diacyl glycerol compounds, phospholipids, lysophosphatidylcholine, eicosanoid compounds (e.g. arachidonic acid), and cannabinoids (e.g., anandamide, 2-AG)) to interact with COE-2 without the labeling of any of the interactants. For example, a microphysiometer can be used to detect the interaction of a compound with COE-2 without the labeling of either the compound or the COE-2. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and COE-2.

In another embodiment, an assay is a cell-based assay comprising contacting a cell expressing a COE-2 target molecule (e.g., a COE-2 substrate, for example diacyl glycerol compounds, phospholipids, lysophosphatidylcholine, eicosanoid compounds (e.g. arachidonic acid), and cannabinoids (e.g., anandamide, 2-AG)) with a test compound and determining the ability of the test compound to modulate (e.g. stimulate or inhibit) the activity of the COE-2 target molecule. Determining the ability of the test compound to modulate the activity of a COE-2 target molecule can be accomplished, for example, by determining the ability of the COE-2 protein to bind to or interact with the COE-2 target molecule.

Determining the ability of the COE-2 protein or a biologically active fragment thereof, to bind to or interact with a COE-2 target molecule can be accomplished by one of the methods described above for determining direct binding. In a preferred embodiment, determining the ability of the COE-2 protein to bind to or interact with a COE-2 target molecule can be accomplished by determining the activity of the target molecule. For example, the activity of the target molecule can be determined by detecting induction of a hydrolytic product of the target molecule (e.g., intracellular alcohols, carboxylic anions, arachidonic acid, fatty acids, lysophosphatidic acid, and inactivated cannabinoids), detecting catalytic/enzymatic activity of the target molecule upon an appropriate substrate, detecting the induction of a reporter gene (comprising a target-responsive regulatory element operatively linked to a nucleic acid encoding a detectable marker, e.g., luciferase), or detecting a target-regulated cellular response (i.e., cell growth or differentiation).

Assays that may be used to identify compounds that modulate COE-2 activity also include assays that test for the ability of a compound to modulate pain and/or inflammation. The ability of a test compound to modulate pain and/or inflammation can be measured by its ability to modulate inflammation of the tissues surrounding the site of injury.

In yet another embodiment, an assay of the present invention is a cell-free assay in which a COE-2 protein or biologically active portion thereof is contacted with a test compound and the ability of the test compound to bind to the COE-2 protein or biologically active portion thereof is determined. Preferred biologically active portions of the COE-2 proteins to be used in assays of the present invention include fragments which participate in interactions with non-COE-2 molecules, e.g., fragments with high surface probability scores. Binding of the test compound to the COE-2 protein can be determined either directly or indirectly as described above. In a preferred embodiment, the assay includes contacting the COE-2 protein or biologically active portion thereof with a known compound which binds COE-2 to form an assay mixture, contacting the assay mixture with a test compound, and determining the ability of the test compound to interact with a COE-2 protein, wherein determining the ability of the test compound to interact with a COE-2 protein comprises determining the ability of the test compound to preferentially bind to COE-2 or biologically active portion thereof as compared to the known compound.

In another embodiment, the assay is a cell-free assay in which a COE-2 protein or biologically active portion thereof is contacted with a test compound and the ability of the test compound to modulate (e.g., stimulate or inhibit) the activity of the COE-2 protein or biologically active portion thereof is determined. Determining the ability of the test compound to modulate the activity of a COE-2 protein can be accomplished, for example, by determining the ability of the COE-2 protein to bind to a COE-2 target molecule by one of the methods described above for determining direct binding. Determining the ability of the COE-2 protein to bind to a COE-2 target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a COE-2 protein can be accomplished by determining the ability of the COE-2 protein to further modulate the activity of a downstream effector of a COE-2 target molecule. For example, the activity of the effector molecule on an appropriate target can be determined or the binding of the effector to an appropriate target can be determined as previously described.

In yet another embodiment, the cell-free assay involves contacting a COE-2 protein or biologically active portion thereof with a known compound which binds the COE-2 protein to form an assay mixture, contacting the assay mixture with a test compound, and determining the ability of the test compound to interact with the COE-2 protein, wherein determining the ability of the test compound to interact with the COE-2 protein comprises determining the ability of the COE-2 protein to preferentially bind to or modulate the activity of a COE-2 target molecule.

The cell-free assays of the present invention are amenable to use of both soluble and/or membrane-bound forms of isolated proteins (e.g., COE-2 proteins or biologically active portions thereof ). In the case of cell-free assays in which a membrane-bound form of an isolated protein is used it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycolether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either COE-2 or its target molecule to facilitate separation of complexed from uncomplexed forms of one or both of the proteins, as well as to accommodate automation of the assay. Binding of a test compound to a COE-2 protein, or interaction of a COE-2 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/COE-2 fusion proteins or glutathione-S-transferase/target fusion proteins can be adsorbed onto glutathione sepharose beads (Sigma Chemical, St. Louis, Mo.) or glutathione derivatized micrometer plates, which are then combined with the test compound or the test compound and either the non-adsorbed target protein or COE-2 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of COE-2 binding or activity determined using standard techniques.

Other techniques for immobilizing proteins on matrices can also be used in the screening assays of the invention. For example, either a COE-2 protein or a COE-2 target molecule can be immobilized utilizing conjugation of biotin and streptavidin. Biotinylated COE-2 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with COE-2 protein or target molecules but which do not interfere with binding of the COE-2 protein to its target molecule can be derivatized to the wells of the plate, and unbound target or COE-2 protein trapped in the wells by antibody conjugation. Methods for detecting such complexes, in addition to those described above for the GST-immobilized complexes, include immunodetection of complexes using antibodies reactive with the COE-2 protein or target molecule, as well as enzyme-linked assays which rely on detecting an enzymatic activity associated with the COE-2 protein or target molecule.

In another embodiment, modulators of COE-2 expression are identified in a method wherein a cell is contacted with a candidate compound and the expression of COE-2 mRNA or protein in the cell is determined. The level of expression of COE-2 mRNA or protein in the presence of the candidate compound is compared to the level of expression of COE-2 mRNA or protein in the absence of the candidate compound. The candidate compound can then be identified as a modulator of COE-2 expression based on this comparison. For example, when expression of COE-2 mRNA or protein is greater (statistically significantly greater) in the presence of the candidate compound than in its absence, the candidate compound is identified as a stimulator of COE-2 mRNA or protein expression. Alternatively, when expression of COE-2 mRNA or protein is less (statistically significantly less) in the presence of the candidate compound than in its absence, the candidate compound is identified as an inhibitor of COE-2 mRNA or protein expression. The level of COE-2 mRNA or protein expression in the cells can be determined by methods described herein for detecting COE-2 mRNA or protein.

In yet another aspect of the invention, the COE-2 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with COE-2 ("COE-2-binding proteins" or "COE-2-bp") and are involved in COE-2 activity. Such COE-2-binding proteins are also likely to be involved in the propagation of signals by the COE-2 proteins or COE-2 targets as, for example, downstream elements of a COE-2-mediated signaling pathway. Alternatively, such COE-2-binding proteins may be COE-2 inhibitors.

The two-hybrid system is based on the modular nature of most transcription factors, which consist of separable DNA-binding and activation domains. Briefly, the assay utilizes two different DNA constructs. In one construct, the gene that codes for a COE-2 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a COE-2-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the COE-2 protein.

In another aspect, the invention pertains to a combination of two or more of the assays described herein. For example, a modulating agent can be identified using a cell-based or a cell free assay, and the ability of the agent to modulate the activity of a COE-2 protein can be confirmed in vivo, e.g., in an animal such as an animal model for pain, e.g., chronic pain and/or neuropathic pain, an animal model for an inflammatory disorder, or an animal model for drug sensitivity, for cellular transformation and/or tumorigenesis.

The ability of a given modulating agent to modulate pain can be quantitated by using any one of the following tests: tight ligation of L6 and L7, as a model of neuropathic pain; complete Freund's adjuvant into knee joint or hind paw as a model of Long term inflammatory pain (Palecek, J. (1992) *Neurophysiol* 68:1951–66); nerve ligation (CCI); thermal hyperalgesia, tactile allodynia and cold allodynia (Carlton, S. M. et al. (1994) *Pain* 56:155–66); thermal paw withdrawal latency (Hargreaves test); von Frey mechanical withdrawal threshold; the hot-plate latency test; the tail flick test (Stone, L. S., et al. (1997) *NeruroReport* 8:3131–3135); the warm-water immersion tail flick assay (Stone, L. S., et al. (1997) *NeruroReport* 8:3131–3135); the crush injury to the sciatic nerve test (De Konig, et al. (1986) *J. Neurol. Sci.* 74:237–246); the cold water allodynia test (Hunter, et al. (1997) *Pain* 69:317–322; the paw pressure latency assay (Hakki-Onen, S., et al. (2001) *Brain Research* 900(2): 261–7; or the radiant heat test (Yoshimura, M., (2001) *Pharm. Research* 44(2):105–11.

Briefly, the tail flick latency test involves projecting a beam of light to the tail of an animal. The time is measured from the onset of the tail heating and stops at the moment of the tail flick. Typically, five tail flick latency (TFL) measurements are made per rat per session with 5–10 minutes between trials.

The thermal paw withdrawal latency test, also known as the Hargreaves test, consists of directing a light beam onto the ventral surface of the rats' left hindpaw from below and measuring the time until the paw is reflexively moved away from the light.

The von Frey mechanical withdrawal threshold involves placing the rat on a screen surface and attaching a von Frey filament to a force transducer. The filament is pressed upward against the ventral right hindpaw of the animal to measure the force at the instant of paw withdrawal.

The hot-plate latency test involves placing a rat onto a heated surface and measuring the time it takes the animal to jump or to lick a hindpaw.

Animal models for pain or inflammation may also be produced by the following methods: subcutaneous injection of formalin, lambda-carrageenan, Mustard oil, or complete Freund's adjuvant (CFA) into the right hind paw or knee of an animal, which causes inflammatory pain; chronic constriction of the sciatic nerve of an animal, which induces neuropathic pain; dibutylin dichloride injection in an animal, which causes chronic pancreatic inflammation; axotomy of the sciatic nerve or the tibial nerve of an animal; or chronic constriction of the spinal nerves of an animal which induces neuropathic pain.

This invention further pertains to novel agents identified by the above-described screening assays. Accordingly, it is within the scope of this invention to further use an agent identified as described herein in an appropriate animal model. For example, an agent identified as described herein (e.g., a COE-2 modulating agent, an antisense COE-2 nucleic acid molecule, a COE-2-specific antibody, or a COE-2 binding partner or ligand) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the COE-2 nucleotide sequences, described herein, can be used to map the location of the COE-2 genes on a chromosome. The mapping of the COE-2 sequences to chromosomes is an important first step in correlating these sequences with genes associated with disease.

Briefly, COE-2 genes can be mapped to chromosomes by preparing PCR primers (preferably 15–25 bp in length) from the COE-2 nucleotide sequences. Computer analysis of the COE-2 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the COE-2 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220: 919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the COE-2 nucleotide sequences to design oligonucleotide primers, sublocalization can be achieved with panels of fragments from specific chromosomes. Other mapping strategies which can similarly be used to map a COE-2 sequence to its chromosome include in situ hybridization (described in Fan, Y. et al. (1990) *Proc. Natl. Acad. Sci. USA,* 87:6223–27), pre-screening with labeled flow-sorted chromosomes, and pre-selection by hybridization to chromosome-specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in McKusick, V., Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature,* 325:783–787.

Moreover, differences in the DNA sequences between individuals affected and unaffected with a disease associated with the COE-2 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The COE-2 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the COE-2 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The COE-2 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can comfortably provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from COE-2 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial COE-2 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the COE-2 nucleotide sequences or portions thereof, e.g., fragments derived from the noncoding regions of SEQ ID NO:1 having a length of at least 20 bases, preferably at least 30 bases.

The COE-2 nucleotide sequences described herein can further be used to provide polynucleotide reagents, e.g., labeled or labelable probes which can be used in, for example, an in situ hybridization technique, to identify a specific tissue, e.g., a tissue containing endothelial cells. This can be very useful in cases where a forensic pathologist is presented with a tissue of unknown origin. Panels of such COE-2 probes can be used to identify tissue by species and/or by organ type.

In a similar fashion, these reagents, e.g., COE-2 primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining COE-2 protein and/or nucleic acid expression as well as COE-2 activity, in the context of a biological sample (e.g., blood, serum, cells, or tissue) to thereby determine whether an individual is afflicted with a disease or disorder, or is at risk of developing a disorder, associated with aberrant or unwanted COE-2 expression or activity. The invention also provides for prognostic (or predictive) assays for determining whether an individual is at risk of developing a disorder associated with COE-2 protein, nucleic acid expression or activity. For example, mutations in a COE-2 gene can be assayed in a biological sample. Such assays can be used for prognostic or predictive purpose to thereby prophylactically treat an individual prior to the onset of a disorder characterized by or associated with COE-2 protein, nucleic acid expression or activity.

Another aspect of the invention pertains to monitoring the influence of agents (e.g., drugs, compounds) on the expression or activity of COE-2 in clinical trials.

These and other agents are described in further detail in the following sections.

1. Diagnostic Assays

An exemplary method for detecting the presence or absence of COE-2 protein, polypeptide or nucleic acid in a biological sample involves obtaining a biological sample from a test subject and contacting the biological sample with a compound or an agent capable of detecting COE-2 protein, polypeptide or nucleic acid (e.g., mRNA, genomic DNA) that encodes COE-2 protein such that the presence of COE-2 protein or nucleic acid is detected in the biological sample. In another aspect, the present invention provides a method for detecting the presence of COE-2 activity in a biological sample by contacting the biological sample with an agent capable of detecting an indicator of COE-2activity such that the presence of COE-2 activity is detected in the biological sample. A preferred agent for detecting COE-2 mRNA or genomic DNA is a labeled nucleic acid probe capable of hybridizing to COE-2 mRNA or genomic DNA. The nucleic acid probe can be, for example, a full-length COE-2 nucleic acid, such as the nucleic acid of SEQ ID NO: 1 or 3, or a portion thereof, such as an oligonucleotide of at least 15, 30, 50, 100, 250 or 500 nucleotides in length and sufficient to specifically hybridize under stringent conditions to COE-2 mRNA or genomic DNA. Other suitable probes for use in the diagnostic assays of the invention are described herein.

A preferred agent for detecting COE-2 protein is an antibody capable of binding to COE-2 protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect COE-2 mRNA, protein, or genomic DNA in a biological sample in vitro as well as in vivo. For example, in vitro techniques for detection of COE-2 mRNA include Northern hybridizations and in situ hybridizations. In vitro techniques for detection of COE-2 protein include enzyme linked immunosorbent assays (ELISAs), Western blots, immunoprecipitations and immunofluorescence. In vitro techniques for detection of COE-2 genomic DNA include Southern hybridizations. Furthermore, in vivo techniques for detection of a COE-2 protein include introducing into a subject a labeled anti-COE-2 antibody. For example, the antibody can be labeled with a radioactive marker whose presence and location in a subject can be detected by standard imaging techniques.

The present invention also provides diagnostic assays for identifying the presence or absence of a genetic alteration characterized by at least one of (i) aberrant modification or mutation of a gene encoding a COE-2 protein; (ii) aberrant expression of a gene encoding a COE-2 protein; (iii) misregulation of the gene; and (iii) aberrant post-translational modification of a COE-2 protein, wherein a wild-type form of the gene encodes a protein with a COE-2 activity. "Misexpression or aberrant expression", as used herein, refers to a non-wild type pattern of gene expression, at the RNA or protein level. It includes, but is not limited to, expression at non-wild type levels (e.g., over- or under-expression); a pattern of expression that differs from wild type in terms of the time or stage at which the gene is expressed (e.g., increased or decreased expression (as compared with wild type) at a predetermined developmental period or stage); a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene (e.g., a pattern of increased or decreased expression (as compared with wild type) in the presence of an increase or decrease in the strength of the stimulus).

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting COE-2 protein, mRNA, or genomic DNA, such that the presence of COE-2 protein, mRNA or genomic DNA is detected in the biological sample, and comparing the presence of COE-2 protein, mRNA or genomic DNA in the control sample with the presence of COE-2 protein, mRNA or genomic DNA in the test sample.

The invention also encompasses kits for detecting the presence of COE-2 in a biological sample. For example, the kit can comprise a labeled compound or agent capable of detecting COE-2 protein or mRNA in a biological sample; means for determining the amount of COE-2 in the sample; and means for comparing the amount of COE-2 in the sample with a standard. The compound or agent can be packaged in a suitable container. The kit can further comprise instructions for using the kit to detect COE-2 protein or nucleic acid.

2. Prognostic Assays

The diagnostic methods described herein can furthermore be utilized to identify subjects having or at risk of developing a disease or disorder associated with aberrant or unwanted COE-2 expression or activity. As used herein, the term "aberrant" includes a COE-2 expression or activity which deviates from the wild type COE-2 expression or activity. Aberrant expression or activity includes increased or decreased expression or activity, as well as expression or activity which does not follow the wild type developmental pattern of expression or the subcellular pattern of expression. For example, aberrant COE-2 expression or activity is intended to include the cases in which a mutation in the COE-2 gene causes the COE-2 gene to be under-expressed or over-expressed and situations in which such mutations result in a non-functional COE-2 protein or a protein which does not function in a wild-type fashion, e.g., a protein which does not interact with a COE-2 substrate, or one which interacts with a non-COE-2 substrate. As used herein, the term "unwanted" includes an unwanted phenomenon involved in a biological response such as pain or deregulated cell proliferation. For example, the term unwanted includes a COE-2 expression or activity which is undesirable in a subject.

The assays described herein, such as the preceding diagnostic assays or the following assays, can be utilized to identify a subject having or at risk of developing a disorder associated with a misregulation in COE-2 protein activity or nucleic acid expression, such as a cell proliferation and/or differentiation disorder. Alternatively, the prognostic assays can be utilized to identify a subject having or at risk for developing a disorder associated with a misregulation in COE-2 protein activity or nucleic acid expression, such as a drug or toxin sensitivity disorder or a cell proliferation and/or differentiation disorder. Thus, the present invention provides a method for identifying a disease or disorder associated with aberrant or unwanted COE-2 expression or activity in which a test sample is obtained from a subject and COE-2 protein or nucleic acid (e.g., mRNA or genomic DNA) is detected, wherein the presence of COE-2 protein or nucleic acid is diagnostic for a subject having or at risk of developing a disease or disorder associated with aberrant or unwanted COE-2 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted COE-2 expression or activity. For example, such methods can be used to determine whether a subject can be effectively treated with an agent for a drug or toxin sensitivity disorder or a cell proliferation and/or differentiation disorder. Thus, the present invention provides methods for determining whether a subject can be effectively treated with an agent for a disorder associated with aberrant or unwanted COE-2 expression or activity in which a test sample is obtained and COE-2 protein or nucleic acid expression or activity is detected (e.g., wherein the abundance of COE-2 protein or nucleic acid expression or activity is diagnostic for a subject that can be administered the agent to treat a disorder associated with aberrant or unwanted COE-2 expression or activity).

The methods of the invention can also be used to detect genetic alterations in a COE-2 gene, thereby determining if a subject with the altered gene is at risk for a disorder characterized by misregulation in COE-2 protein activity or nucleic acid expression, such as a drug or toxin sensitivity disorder or a cell proliferation and/or differentiation disorder. In preferred embodiments, the methods include detecting, in a sample of cells from the subject, the presence or absence of a genetic alteration characterized by at least one of an alteration affecting the integrity of a gene encoding a COE-2-protein, or the mis-expression of the COE-2 gene. For example, such genetic alterations can be detected by ascertaining the existence of at least one of 1) a deletion of one or more nucleotides from a COE-2 gene; 2) an addition of one or more nucleotides to a COE-2 gene; 3) a substitution of one or more nucleotides of a COE-2 gene, 4) a chromosomal rearrangement of a COE-2 gene; 5) an alteration in the level of a messenger RNA transcript of a COE-2 gene, 6) aberrant modification of a COE-2 gene, such as of the methylation pattern of the genomic DNA, 7) the presence of a non-wild type splicing pattern of a messenger RNA transcript of a COE-2 gene, 8) a non-wild type level of a COE-2-protein, 9) allelic loss of a COE-2 gene, and 10) inappropriate post-translational modification of a COE-2-protein. As described herein, there are a large number of assays known in the art which can be used for detecting alterations in a COE-2 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the COE-2-gene (see Abravaya et al. (1995) *Nucleic Acids Res.* 23:675–682). This method can include the steps of collecting a sample of cells from a subject, isolating nucleic acid (e.g., genomic, mRNA or both) from the cells of the sample, contacting the nucleic acid sample with one or more primers which specifically hybridize to a COE-2 gene under conditions such that hybridization and amplification of the COE-2-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) *Proc. Natl. Acad. Sci. USA* 87:1874–1878), transcriptional amplification system (Kwoh, D. Y. et al. (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a COE-2 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in COE-2 can be identified by hybridizing a sample and control nucleic acids, e.g., DNA or RNA, to high density arrays containing hundreds or thousands of oligonucleotides probes (Cronin, M. T. et al. (1996) *Human Mutation* 7:244–255; Kozal, M. J. et al. (1996) *Nature Medicine* 2:753–759). For example, genetic mutations in COE-2 can be identified in two dimensional arrays containing light-generated DNA probes as described in Cronin, M. T. et al. (1996) supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the COE-2 gene and detect mutations by comparing the sequence of the sample COE-2 with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays (Naeve, C. W. (1995) *Biotechniques* 19:448), including sequencing by mass spectrometry (see, e.g., PCT International Publication No. WO 94/16101; Cohen et al. (1 996) *Adv. Chromatogr.* 36:127–162; and Griffin et al. (1993) *Appl.. Biochem. Biotechnol.* 38:147–159).

Other methods for detecting mutations in the COE-2 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type COE-2 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in COE-2 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a COE-2 sequence, e.g., a wild-type COE-2 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in COE-2 genes. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125–144; and Hayashi (1992) *Genet. Anal. Tech. Appl.* 9:73–79). Single-stranded DNA fragments of sample and control COE-2 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 1 1:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a COE-2 gene.

Furthermore, any cell type or tissue in which COE-2 is expressed may be utilized in the prognostic assays described herein.

3. Monitoring of Effects During Clinical Trials

Monitoring the influence of agents (e.g., drugs) on the expression or activity of a COE-2 protein (e.g., the modulation of gene expression, and or cell growth and differentiation mechanisms) can be applied not only in basic drug screening, but also in clinical trials. For example, the effectiveness of an agent determined by a screening assay as described herein to increase COE-2 gene expression, protein levels, or upregulate COE-2 activity, can be monitored in clinical trials of subjects exhibiting decreased COE-2 gene expression, protein levels, or downregulated COE-2 activity. Alternatively, the effectiveness of an agent determined by a screening assay to decrease COE-2 gene expression, protein levels, or downregulate COE-2 activity, can be monitored in clinical trials of subjects exhibiting increased COE-2 gene expression, protein levels, or upregulated COE-2 activity. In such clinical trials, the expression or activity of a COE-2 gene, and preferably, other genes that have been implicated in, for example, a COE-2-associated disorder can be used as a "read out" or markers of the phenotype of a particular cell.

For example, and not by way of limitation, genes, including COE-2, that are modulated in cells by treatment with an agent (e.g., compound, drug or small molecule) which modulates COE-2 activity (e.g., identified in a screening assay as described herein) can be identified. Thus, to study the effect of agents on COE-2-associated disorders (e.g., disorders characterized by deregulated gene expression, and/or cell growth and differentiation mechanisms), for example, in a clinical trial, cells can be isolated and RNA prepared and analyzed for the levels of expression of COE-2 and other genes implicated in the COE-2-associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of COE-2 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a COE-2 protein, mRNA, or genomic DNA in the preadministration sample; (iii) obtaining one or more post-administration samples from the subject; (iv) detecting the level of expression or activity of the COE-2 protein, mRNA, or genomic DNA in the post-administration samples; (v) comparing the level of expression or activity of the COE-2 protein, mRNA, or genomic DNA in the pre-administration sample with the COE-2 protein, mRNA, or genomic DNA in the post administration sample or samples; and (vi) altering the administration of the agent to the subject accordingly. For example, increased administration of the agent may be desirable to increase the expression or activity of COE-2 to higher levels than detected, i.e., to increase the effectiveness of the agent. Alternatively, decreased administration of the agent may be desirable to decrease expression or activity of COE-2 to lower levels than detected, i.e. to decrease the effectiveness of the agent. According to such an embodiment, COE-2 expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having a COE-2-associated disorder, e.g., a disorder associated with aberrant or unwanted COE-2 expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the COE-2 molecules of the present invention or COE-2 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted COE-2 expression or activity, by administering to the subject a COE-2 or an agent which modulates COE-2 expression or at least one COE-2 activity.

Subjects at risk for a disease which is caused or contributed to by aberrant or unwanted COE-2 expression or activity can be identified by, for example, any or a combination of diagnostic or prognostic assays as described herein. Administration of a prophylactic agent can occur prior to the manifestation of symptoms characteristic of the COE-2 aberrancy, such that a disease or disorder is prevented or, alternatively, delayed in its progression. Depending on the type of COE-2 aberrancy, for example, a COE-2, COE-2 agonist or COE-2 antagonist agent can be used for treating the subject. The appropriate agent can be determined based on screening assays described herein.

2. Therapeutic Methods

Another aspect of the invention pertains to methods of modulating COE-2 expression or activity for therapeutic purposes. Accordingly, in an exemplary embodiment, the modulatory method of the invention involves contacting a cell capable of expressing COE-2 with an agent that modulates one or more of the activities of COE-2 protein activity associated with the cell, such that COE-2 activity in the cell is modulated. An agent that modulates COE-2 protein activity can be an agent as described herein, such as a nucleic acid or a protein, a naturally-occurring target molecule of a COE-2 protein (e.g., a COE-2 substrate or ligand), a COE-2 antibody, a COE-2 agonist or antagonist, a peptidomimetic of a COE-2 agonist or antagonist, or other small molecule. In one embodiment, the agent stimulates one or more COE-2 activities. Examples of such stimulatory agents include active COE-2 protein and a nucleic acid molecule encoding COE-2 that has been introduced into the cell. In another embodiment, the agent inhibits one or more COE-2 activities. Examples of such inhibitory agents include antisense COE-2 nucleic acid molecules, anti-COE-2 antibodies, and COE-2 inhibitors. These modulatory methods can be performed in vitro (e.g., by culturing the cell with the agent) or, alternatively, in vivo (e.g., by administering the agent to a subject). As such, the present invention provides methods of providing treatment to an individual afflicted with a disease or disorder characterized by aberrant or unwanted expression or activity of a COE-2 protein or nucleic acid molecule. As used herein, the term "treatment" includes the application or administration of a therapeutic agent to a patient. Treatment is also meant to include the application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. As used herein, the term "therapeutic agent" includes, but is not limited to, small molecules, peptides, antibodies, ribozymes and antisense oligonucleotides as described herein.

In one embodiment, the method involves administering an agent (e.g., an agent identified by a screening assay described herein), or combination of agents that modulates (e.g., up- or down-regulates) COE-2 expression or activity. In another embodiment, the method involves administering a COE-2 protein or nucleic acid molecule as therapy to compensate for reduced, aberrant, or unwanted COE-2 expression or activity.

Stimulation of COE-2 activity is desirable in situations in which COE-2 is abnormally downregulated and/or in which increased COE-2 activity is likely to have a beneficial effect. For example, stimulation of COE-2 activity is desirable in situations in which a COE-2 is downregulated and/or in which increased COE-2 activity is likely to have a beneficial effect. Likewise, inhibition of COE-2 activity is desirable in situations in which COE-2 is abnormally upregulated and/or in which decreased COE-2 activity is likely to have a beneficial effect.

3. Pharmacogenomics

The COE-2 molecules of the present invention, as well as agents, or modulators which have a stimulatory or inhibitory effect on COE-2 activity (e.g., COE-2 gene expression) as identified by a screening assay described herein can be administered to individuals to treat (prophylactically or therapeutically) COE-2-associated disorders (e.g., disorders characterized by aberrant gene expression, or cell proliferation and/or differentiation disorders) associated with aberrant or unwanted COE-2 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a COE-2 molecule or COE-2 modulator as well as tailoring the dosage and/or therapeutic regimen of treatment with a COE-2 molecule or COE-2 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11):983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate carboxylesterase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach" can be utilized to identify genes that predict drug response. According to this method, if a gene that encodes a drug's target is known (e.g., a COE-2 protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-carboxylesterase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a COE-2 molecule or COE-2 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a COE-2 molecule or COE-2 modulator, such as a modulator identified by one of the exemplary screening assays described herein.

4. Use of COE-2 Molecules as Surrogate Markers

The COE-2 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the COE-2 molecules of the invention may be detected, and may be correlated with one or more biological states in vivo. For example, the COE-2 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35:258–264; and James (1994) *AIDS Treatment News Archive* 209.

The COE-2 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a COE-2 marker) transcription or expression, the amplified marker may be in a quantity which is more readily detectable than the drug itself. Also, the marker may be more easily detected due to the nature of the marker itself; for example, using the methods described herein, anti-COE-2 antibodies may be employed in an immune-based detection system for a COE-2 protein marker, or COE-2-specific radiolabeled probes may be used to detect a COE-2 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90:229–238; Schentag (1999) *Am. J. Health-Syst. Pharm.* 56 Suppl. 3:S21–S24; and Nicolau (1999) *Am. J. Health-Syst. Pharm.* 56 Suppl. 3:S16–S20.

The COE-2 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35(12):1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., COE-2 protein or RNA) for specific tumor markers in a subject, a drug or course of treatment may be selected that is optimized for the treatment of the specific tumor likely to be present in the subject. Similarly, the presence or absence of a specific sequence mutation in COE-2 DNA may correlate COE-2 drug response. The use of pharmacogenomic markers therefore permits the application of the most appropriate treatment for each subject without having to administer the therapy.

E. Electronic Apparatus Readable Media and Arrays

Electronic apparatus readable media comprising COE-2 sequence information is also provided. As used herein, "COE-2 sequence information" refers to any nucleotide and/or amino acid sequence information particular to the COE-2 molecules of the present invention, including but not limited to full-length nucleotide and/or amino acid sequences, partial nucleotide and/or amino acid sequences, polymorphic sequences including single nucleotide polymorphisms (SNPs), epitope sequences, and the like. Moreover, information "related to" said COE-2 sequence information includes detection of the presence or absence of a sequence (e.g., detection of expression of a sequence, fragment, polymorphism, etc.), determination of the level of a sequence (e.g., detection of a level of expression, for example, a quantitative detection), detection of a reactivity to a sequence (e.g., detection of protein expression and/or levels, for example, using a sequence-specific antibody), and the like. As used herein, "electronic apparatus readable media" refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon a sequence of the present invention.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the COE-2 sequence information.

A variety of software programs and formats can be used to store the sequence information on the electronic apparatus readable medium. For example, the sequence information can be represented in a word processing text filer, formatted in commercially-available software such as WordPerfect and MicroSoft Word, or represented in the form of an ASCII file, stored in a database application, such as DB2, Sybase, Oracle, or the like, as well as in other forms. Any number of dataprocessor structuring formats (e.g., text file or database) may be employed in order to obtain or create a medium having recorded thereon the COE-2 sequence information.

By providing COE-2 sequence information in readable form, one can routinely access the sequence information for a variety of purposes. For example, one skilled in the art can use the sequence information in readable form to compare a target sequence or target structural motif with the sequence information stored within the data storage means. Search means are used to identify fragments or regions of the sequences of the invention which match a particular target sequence or target motif.

The present invention therefore provides a medium for holding instructions for performing a method for determining whether a subject has a COE-2-associated disease or disorder (e.g., an inflammatory or pain disorder) or a pre-disposition to a COE-2-associated disease or disorder, wherein the method comprises the steps of determining COE-2 sequence information associated with the subject and based on the COE-2 sequence information, determining whether the subject has a COE-2-associated disease or disorder (e.g., an inflammatory or pain disorder) or a pre-disposition to a COE-2-associated disease or disorder and/or recommending a particular treatment for the disease, disorder or pre-disease condition.

The present invention further provides in an electronic system and/or in a network, a method for determining whether a subject has a COE-2-associated disease or disorder (e.g., an inflammatory or pain disorder) or a pre-disposition to a disease associated with a COE-2 wherein the method comprises the steps of determining COE-2 sequence information associated with the subject, and based on the COE-2 sequence information, determining whether the subject has a COE-2-associated disease or disorder or a pre-disposition to a COE-2-associated disease or disorder, and/or recommending a particular treatment for the disease, disorder or pre-disease condition. The method may further comprise the step of receiving phenotypic information associated with the subject and/or acquiring from a network phenotypic information associated with the subject.

The present invention also provides in a network, a method for determining whether a subject has a COE-2-associated disease or disorder (e.g., an inflammatory or pain disorder) or a pre-disposition to a COE-2-associated disease or disorder associated with COE-2, said method comprising the steps of receiving COE-2 sequence information from the subject and/or information related thereto, receiving phenotypic information associated with the subject, acquiring information from the network corresponding to COE-2-associated disease or disorder, and based on one or more of the phenotypic information, the COE-2 information (e.g., sequence information and/or information related thereto), and the acquired information, determining whether the subject has a COE-2-associated disease or disorder (e.g., an inflammatory or pain disorder) or a pre-disposition to a COE-2-associated disease or disorder. The method may further comprise the step of recommending a particular treatment for the disease, disorder or pre-disease condition.

The present invention also provides a business method for determining whether a subject has a COE-2-associated disease or disorder (e.g., an inflammatory or pain disorder) or a pre-disposition to a COE-2-associated disease or disorder, said method comprising the steps of receiving information related to COE-2 (e.g., sequence information and/or information related thereto), receiving phenotypic information associated with the subject, acquiring information from the network related to COE-2 and/or related to a COE-2-associated disease or disorder, and based on one or more of the phenotypic information, the COE-2 information, and the acquired information, determining whether the subject has a COE-2-associated disease or disorder or a pre-disposition to a COE-2-associated disease or disorder. The method may further comprise the step of recommending a particular treatment for the disease, disorder or pre-disease condition.

The invention also includes an array comprising a COE-2 sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be COE-2. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a COE-2-associated disease or disorder, progression of COE-2-associated disease or disorder, and processes associated with the COE-2-associated disease or disorder.

The array is also useful for ascertaining the effect of the expression of a gene on the expression of other genes in the same cell or in different cells (e.g., ascertaining the effect of COE-2 expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including COE-2) that could serve as a molecular target for diagnosis or therapeutic intervention.

This invention is further illustrated by the following examples which should not be construed as limiting. The contents of all references, patents and published patent applications cited throughout this application, as well as the figures and the Sequence Listing, are incorporated herein by reference.

EXAMPLES

Example 1

Identification and Characterization of Human COE-2 cDNA

In this example, the identification and characterization of the gene encoding human COE-2 (clone Fbh18903) is described.

Isolation of the Human COE-2 cDNA

The invention is based, at least in part, on the discovery of genes encoding novel members of the carboxylesterase family. The entire sequence of human clone Fbh18903 was determined and found to contain an open reading frame termed human "COE-2."

The nucleotide sequence encoding the human COE-2 is set forth as SEQ ID NO:1. The protein encoded by this nucleic acid comprises about 584 amino acids and has the amino acid sequence set forth as SEQ ID NO:2. The coding region (open reading frame) of SEQ ID NO:1 is set forth as SEQ ID NO:3.

Analysis of the Human COE-2 Molecules

A BLASTN 2.0 search against the dbEST, and PATENT_2 nucleotide databases, using a score of 100 and a word length of 12 (Altschul et al. (1990) *J. Mol. Biol.* 215:403) of the nucleotide sequence of human COE-2 revealed a number of nucleotides with some similarity to that of the invention, including a rabbit liver carboxylesterase (Accession Number Z09683 of the Patent Nucleotide database) with a 58% identity over nucleotides 446–1242 of SEQ ID NO:1, a 62% identity to nucleotides 1562–1805 of SEQ ID NO:1, and a 65% identity to nucleotides 314–438 of SEQ ID NO:1. The searches also identified a human PRO873 nucleotide sequence (Accession Number Z34105 of the Patent Nucleotide database) with a 99% identity over nucleotides 426–1253 of SEQ ID NO:1, a 100% identity over nucleotides 1683–1952 of SEQ ID NO:1, a 99% identity over nucleotides 224–429 of SEQ ID NO:1, and a 98% identity over nucleotides 1328–1486 of SEQ ID NO:1.

A BLASTX 2.0 search against the NRP/protot and PATENT_2/gsprot protein databases, using a wordlength of 3, a score of 100, and a BLOSUM62 matrix, using the amino acid sequence of human COE-2 as a query sequence, identified a number of proteins with some similarity to human COE-2 protein. For example, a rat liver carboxylesterase precursor (GenBank Accession Number P16303) is 44% identical to human COE-2 over amino acid residues 117–430 of SEQ ID NO:2 and 44% identical over amino acid residues 481–580 of SEQ ID NO:2. This search also identified a human PRO873 protein sequence which has a 98% identity over amino acid residues 41–462 of SEQ ID NO:2, a 71% identity over amino acid residues 6–110 of SEQ ID NO:2, and a 100% identity over amino acid residues 111–383 of SEQ ID NO:2.

An analysis of the possible cellular localization of the human COE-2 protein (clone 18903) based on its amino acid sequence was performed using the methods and algorithms described in Nakai and Kanehisa (1992) *Genomics* 14:897–911. The results (shown as percent probability) of the analysis predict that human COE-2 (SEQ ID NO:2) is localized in the mitochondria (52.2%), in the cytoplasm (13.0%), in vacuolar bodies (8.7%), in extracellular space and the cell wall (8.7%), in the endoplasmic reticulum (8.7%), in the golgi apparatus (4.3%), and in the peroxisomal bodies (4.3%).

Figure 1:
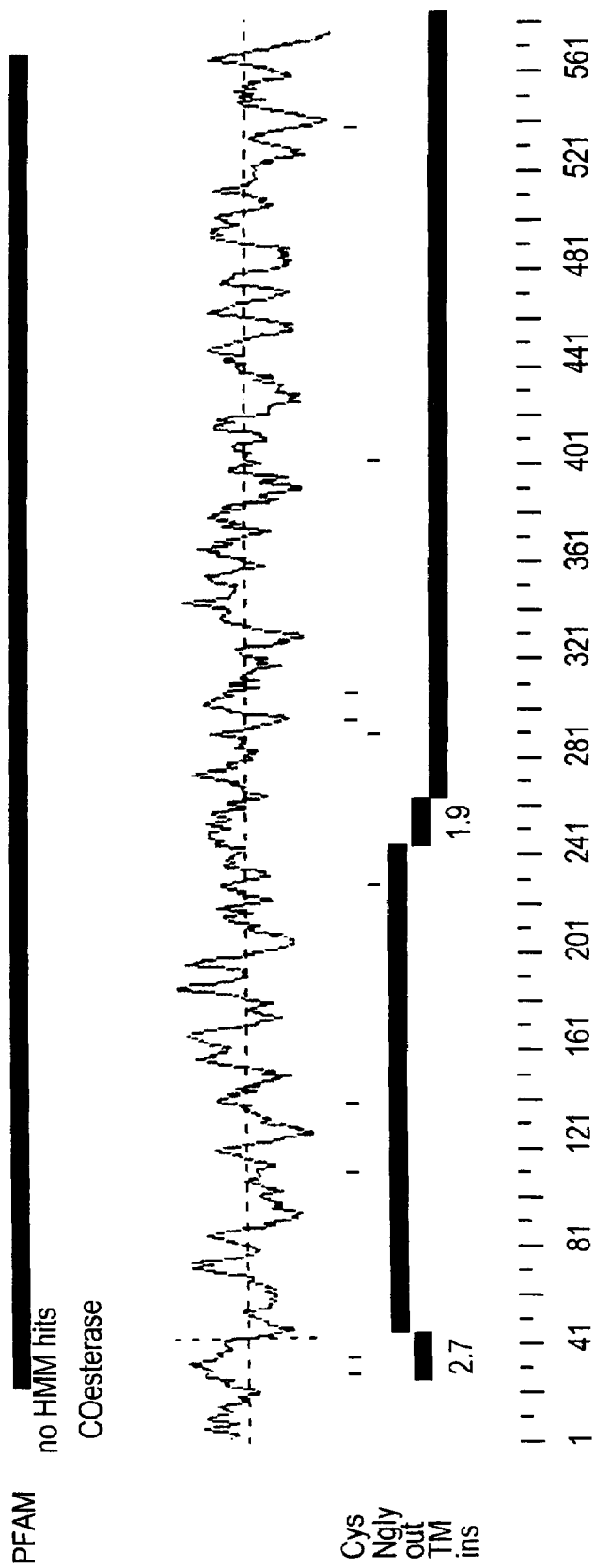
FIG. 1 depicts a structural, hydrophobicity, and antigenicity analysis of the human COE-2 protein.

Searches of the amino acid sequence of human COE-2 were preformed against the HMM database (FIG. 1). These searches resulted in the identification of a "carboxylesterase domain" at about residues 25–569 of SEQ ID NO:2 (score=558.6).

Searches of the amino acid sequence of human COE-2 were further performed against the Prosite database. These searches resulted in the identification in the amino acid sequence of human COE-2 of potential N-glycosylation sites (PS00001) at about residues 237–240, 299–302, and 411–414 of SEQ ID NO:2. In addition, this search identified a potential cAMP/cGMP-dependent protein kinase phosphorylation site (PS00004) at about residues 395–398 of SEQ ID NO:2. This search also identified potential protein kinase C phosphorylation sites (PS00005) at about residues 23–25, 47–49, 125–127, 320–322, 405–407, 554–556, and 575–577 of SEQ ID NO:2. In addition, this search identified potential casein kinase II phosphorylation sites (PS00006) at about residues 125–128, 173–176, and 202–205 of SEQ ID NO:2. Furthermore, this search identified potential tyrosine kinase phosphorylation sites (PS00007) at about residues 99–107, 134–141, and 541–548 of SEQ ID NO:2. A number of N-myristylation sites (PS00008) were also identified at about residues 19–24, 43–48, 57–62, 76–81, 100–105, 117–122, 170–175, 177–182, 232–237, 242–247, 295–300, 487–492, 499–504, 505–510, and 534–539 of SEQ ID NO:2. A "carboxylesterase B1 signature motif" (PS00122) and a "carboxylesterase B2 signature motif" (PS00941) were also identified in this search at about residues 231–246 of SEQ ID NO:2, and at about 137–147 of SEQ ID NO:2, respectively. Specific information regarding these recognition sites can be found using the corresponding Accession Numbers online at the Prosite website.

A search of the amino acid sequence of human COE-2 was also performed against the ProDom database, indicating the presence of a "type-B similar family carboxylesterase/lipase domain" at about residues 44–158 and 249–308 of SEQ ID NO:2, a "carboxylesterase precursor domain" at about residues 52–115 of SEQ ID NO:2, a "hydrolase lipase hormone-sensitive lipid degradation domain" at about residues 144–246 of SEQ ID NO:2, a "glycoprotein serine carboxylesterase acetylcholinesterase cocaine B-esterase domain" at about residues 254–332 of SEQ ID NO:2, a "carboxylesterase family multigene reticulum hydrolase signal domain" at about residues 254–340 of SEQ ID NO:2, an "esterase hydrolase para-nitrobenzyl polyurethane domain" at about residues 360–542 of SEQ ID NO:2, an "esterase carboxylase serine alpha esterase domain" at about residues 364–577 of SEQ ID NO:2, a "carboxylesterase signal serine liver glycoprotein domain" at about residues 366–474 of SEQ ID NO:2, an "acetylcholinesterase domain" at about residues 395–554 of SEQ ID NO:2, an "esterase domain" at about residues 415–573 of SEQ ID NO:2, an "esterase hydrolase domain" at about residues 487–569 of SEQ ID NO:2, and a "carboxylesterase hydrolase precursor domain" at about residues 536–580 of SEQ ID NO:2.

Tissue Distribution of COE-2 mRNA

Endogenous COE-2 gene expression was determined using the Perkin-Elmer/AsI 7700 Sequence Detection System which employs TaqMan technology. Briefly, TaqMan technology relies on standard RT-PCR with the addition of a third gene-specific oligonucleotide (referred to as a probe) which has a fluorescent dye coupled to its 5' end (typically 6-FAM) and a quenching dye at the 3' end (typically TAMRA). When the fluorescently tagged oligonucleotide is intact, the fluorescent signal from the 5' dye is quenched. As PCR proceeds, the 5' to 3' nucleolytic activity of taq polymerase digests the labeled primer, producing a free nucleotide labeled with 6-FAM, which is now detected as a fluorescent signal. The PCR cycle where fluorescence is first released and detected is directly proportional to the starting amount of the gene of interest in the test sample, thus providing a way of quantitating the initial template concentration. Samples can be internally controlled by the addition of a second set of primers/probe specific for a housekeeping gene such as GAPDH which has been labeled with a different fluor on the 5' end (typically JOE). To determine the level of COE-2 in various tissues a primer/probe set was designed using Primer Express software and primary cDNA sequence information. Total RNA was prepared from a series of tissues using an RNeasy kit from Qiagen First strand cDNA was prepared from one µg total RNA using an oligo dT primer and Superscript II reverse transcriptase (GibcoBRL). cDNA obtained from approximately 50 ng total RNA was used per TaqMan reaction. Normal tissues tested include an array of monkey and human tissues. Expression was greatest in brain and spinal cord with notable expression in epithelial and skin cells. These results also indicate that there may be no rodent COE-2 orthologue. The results of these analyses are set forth in FIGS. 5–7.

In addition, in situ hybridization of tissue slices with a labeled nucleic acid human probe corresponding human COE-2 showed highest levels of expression in monkey and human brain as well as monkey skin. Under magnification, it was observed that the majority of neurons in the dorsal root ganglion express also the mRNA for COE-2. Low levels of expression were detected in liver.

Example 2

Expression of Recombinant COE-2 Protein in Bacterial Cells

In this example, human COE-2 is expressed as a recombinant glutathione-S-transferase (GST) fusion polypeptide in E. coli and the fusion polypeptide is isolated and characterized. Specifically, human COE-2 is fused to GST and this fusion polypeptide is expressed in E. coli, e.g., strain PEB199. Expression of the GST-COE-2 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 3

Expression of Recombinant COE-2 Protein in COS Cells

To express the human COE-2 gene in COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire COE-2 protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the COE-2 DNA sequence is amplified by PCR using two primers. The 5' primer contains the restriction site of interest followed by approximately twenty nucleotides of the COE-2 coding sequence starting from the initiation codon; the 3' end sequence contains complementary sequences to the other restriction site of interest, a translation stop codon, the HA tag or FLAG tag and the last 20 nucleotides of the COE-2 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the COE-2 gene is inserted in the correct orientation. The ligation mixture is transformed into E. coli cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the COE-2-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989. The expression of the COE-2 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the COE-2 coding sequence is cloned directly into the polylinker of the pCDNA/Amp vector using the appropriate restriction sites. The resulting plasmid is transfected into COS cells in the manner described above, and the expression of the COE-2 polypeptide is detected by radiolabelling and immunoprecipitation using a COE-2 specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. A method for identifying a candidate compound capable of binding to a polypeptide selected from the group consisting of:
   a) a polypeptide which is at least 95% identical to the amino acid sequence of SEQ ID NO:2, wherein the polypeptide exhibits carboxylesterase activity; and
   b) a polypeptide encoded by a nucleic acid molecule comprising a nucleotide sequence which is at least 95% identical to the nucleotide sequence of SEQ ID NO:1 or SEQ ID NO:3, wherein the polypeptide exhibits carboxylesterase activity;

the method comprising:
   i) combining a compound to be tested with a cell expressing the polypeptide under conditions suitable for binding;
   ii) assessing the ability of the compound to bind to the polypeptide; and
   iii) selecting a compound capable of binding to the polypeptide;

wherein the cell is selected from the group consisting of a brain cell, a cell derived from spinal cord, and a cell derived from dorsal root ganglion;

thereby identifying a candidate compound capable of binding to the polypeptide.

2. The method of claim 1, wherein the compound is selected from the group consisting of a small molecule, a peptide or an antibody.

3. The method of claim 1, wherein the polypeptide further comprises heterologous sequences.

4. The method of claim 1, wherein the binding of the test compound to the polypeptide is determined by a method selected from the group consisting of:
   a) direct detecting of test compound/polypeptide binding;
   b) a competition binding assay; and
   c) an immunoassay.

5. A method for identifying a candidate compound capable of binding to a polypeptide selected from the group consisting of:
   a) a polypeptide comprising the amino acid sequence of SEQ ID NO:2; and
   b) a polypeptide encoded by the nucleotide sequence set forth in SEQ ID NO:1 or SEQ ID NO:3;

the method comprising:
   i) combining a compound to be tested with a cell expressing the polypeptide under conditions suitable for binding;
   ii) assessing the ability of the compound to bind to the polypeptide; and
   iii) selecting a compound capable of binding to the polypeptide;

wherein the cell is selected from the group consisting of a brain cell, a cell derived from spinal cord, and a cell derived from dorsal root ganglion;

thereby identifying a candidate compound capable of binding to the polypeptide.

6. The method of claim 5, wherein the compound is selected from the group consisting of a small molecule, a peptide or an antibody.

7. The method of claim 5, wherein the polypeptide further comprises heterologous sequences.

8. The method of claim 5, wherein the binding of the test compound to the polypeptide is determined by a method selected from the group consisting of:
   a) direct detecting of test compound/polypeptide binding;
   b) a competition binding assay; and
   c) an immunoassay.

* * * * *